United States Patent
Minidis et al.

(10) Patent No.: US 9,650,336 B2
(45) Date of Patent: May 16, 2017

(54) MONO-FLUORO BETA-SECRETASE INHIBITORS

(71) Applicant: ASTRAZENECA AB, Södertälje (SE)

(72) Inventors: Anna Minidis, Södertälje (SE);
Fredrik Rahm, Macclesfield (GB);
Jenny Viklund, Macclesfield (GB)

(73) Assignee: ASTRAZENECA AB, Södertälje (SE)

( * ) Notice: Subject to any disclaimer, the term of this patent is extended or adjusted under 35 U.S.C. 154(b) by 297 days.

(21) Appl. No.: 14/350,729

(22) PCT Filed: Oct. 10, 2012

(86) PCT No.: PCT/GB2012/052510
§ 371 (c)(1),
(2) Date: Apr. 9, 2014

(87) PCT Pub. No.: WO2013/054108
PCT Pub. Date: Apr. 18, 2013

(65) Prior Publication Data
US 2014/0288091 A1   Sep. 25, 2014

Related U.S. Application Data

(60) Provisional application No. 61/545,334, filed on Oct. 10, 2011.

(51) Int. Cl.
| | | |
|---|---|---|
| A61K 31/40 | (2006.01) | |
| A61K 31/44 | (2006.01) | |
| C07D 209/96 | (2006.01) | |
| C07D 209/54 | (2006.01) | |
| C07D 401/10 | (2006.01) | |
| C07D 403/10 | (2006.01) | |
| C07D 491/107 | (2006.01) | |
| C07D 207/34 | (2006.01) | |
| A61K 31/403 | (2006.01) | |
| A61K 31/407 | (2006.01) | |
| A61K 31/4439 | (2006.01) | |
| A61K 31/506 | (2006.01) | |

(Continued)

(52) U.S. Cl.
CPC .......... *C07D 209/54* (2013.01); *A61K 31/403* (2013.01); *A61K 31/407* (2013.01); *A61K 31/4439* (2013.01); *A61K 31/506* (2013.01); *A61K 45/06* (2013.01); *C07D 207/34* (2013.01); *C07D 401/04* (2013.01); *C07D 401/10* (2013.01); *C07D 403/04* (2013.01); *C07D 403/10* (2013.01); *C07D 491/107* (2013.01)

(58) Field of Classification Search
CPC ................ A61K 31/403; A61K 31/407; A61K 31/4439; A61K 31/506; A61K 45/06; C07D 207/34; C07D 209/54; C07D 401/04; C07D 401/10; C07D 403/04; C07D 403/10; C07D 491/107

USPC .................. 514/256, 278, 409; 548/409, 411
See application file for complete search history.

(56) References Cited

U.S. PATENT DOCUMENTS

| 8,415,483 B2 | 4/2013 | Csjernyik et al. |
| 8,865,911 B2 * | 10/2014 | Csjernyik ............ C07D 235/02 546/15 |

(Continued)

FOREIGN PATENT DOCUMENTS

| CN | 102348698 | 2/2012 |
| JP | 2010517963 | 5/2010 |

(Continued)

OTHER PUBLICATIONS

Evin et al., "BACE inhibitors as potential therapeutics for Alzheimer's disease," Recent Patents on CNS Drug Discovery, Bentham Science Publishers Ltd, NL, vol. 2, No. 3, Nov. 1, 2007 (Nov. 1, 2007), pp. 188-199.

(Continued)

*Primary Examiner* — My-Chau T Tran
(74) *Attorney, Agent, or Firm* — Ropes & Gray LLP

(57) ABSTRACT

Beta-secretase inhibitors, of formula (I) as described in the specification, pharmaceutical compositions comprising them and therapeutic methods using them for the treatment and/or prevention of Aβ-related pathologies such as Down's syndrome, β-amyloid angiopathy such as but not limited to cerebral amyloid angiopathy or hereditary cerebral hemorrhage, disorders associated with cognitive impairment such as but not limited to MCI ("mild cognitive impairment"), Alzheimer's Disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration.

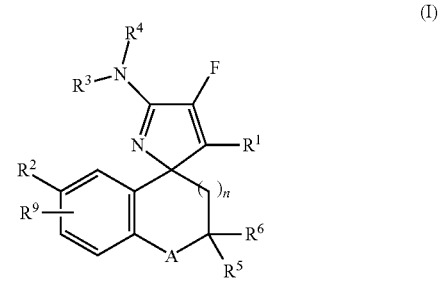

(I)

16 Claims, No Drawings

(51) Int. Cl.
*A61K 45/06* (2006.01)
*C07D 401/04* (2006.01)
*C07D 403/04* (2006.01)

(56) References Cited

U.S. PATENT DOCUMENTS

| | | | |
|---|---|---|---|
| 9,000,182 | B2 | 4/2015 | Karlstrom et al. |
| 9,000,183 | B2 * | 4/2015 | Karlstrom .......... A61K 31/4184 546/15 |
| 9,000,184 | B2 | 4/2015 | Karlstrom et al. |
| 9,000,185 | B2 | 4/2015 | Karlstrom et al. |
| 9,248,129 | B2 | 2/2016 | Csjernyik et al. |
| 2004/0116478 | A1 | 6/2004 | Moon |
| 2011/0144154 | A1 | 6/2011 | Fournet |
| 2013/0317014 | A1 | 11/2013 | Dillard et al. |
| 2014/0031379 | A1 | 1/2014 | Bohlin et al. |
| 2014/0200223 | A1 | 7/2014 | Cacatian et al. |
| 2016/0184303 | A1 | 6/2016 | Csjernyik et al. |

FOREIGN PATENT DOCUMENTS

| | | |
|---|---|---|
| JP | 2010526808 | 8/2010 |
| WO | WO02098462 | 12/2002 |
| WO | WO2005094822 | 10/2005 |
| WO | WO2006138264 | 12/2006 |
| WO | WO2007058601 | 5/2007 |
| WO | WO2007076247 | 7/2007 |
| WO | WO2007100536 | 9/2007 |
| WO | WO2008076043 | 6/2008 |
| WO | WO2009100169 | 8/2009 |
| WO | WO2010013794 | 2/2010 |
| WO | WO2010021680 | 2/2010 |
| WO | WO2010030954 | 3/2010 |
| WO | WO2010105179 | 9/2010 |
| WO | WO2011002407 | 1/2011 |
| WO | WO2011002408 | 1/2011 |
| WO | WO2011106414 | 9/2011 |
| WO | WO2011123674 | 10/2011 |
| WO | WO2011130741 | 10/2011 |
| WO | WO2012019056 | 2/2012 |
| WO | WO2012040641 | 3/2012 |
| WO | WO2012071458 | 5/2012 |
| WO | WO2012087237 | 6/2012 |

OTHER PUBLICATIONS

Hong et al., "Structure of the Protease Domain of Memapsin 2 (β-Secretase) Complexed with Inhibitor," Science 2000, 290, 5489, pp. 150-153.

John et al, "Human β-Secretase (BACE) and BACE Inhibitors," Journal of Medicinal Chemistry, 2003, 46, pp. 4625-4630.

Roberds et al, "BACE knockout mice are healthy despite lacking the primary β-secretase activity in brain: implications for Alzheimer's disease therapeutics," Human Molecular Genetics, 2001, 10, pp. 1317-1324.

Sinha et al, "Purification and cloning of amyloid precursor protein β-secretase from human brain," Nature, 1999, 402, pp. 537-540.

STN, pp. 9-13, obtained Feb. 3, 2015 (RN 1521274-03-2 HCAPLUS).

SciFinder, pp. 2-5, obtained Feb. 3, 2015 (Accession No. 2012:926087, CAN 157:165533, CAPLUS).

SciFinder, pp. 1, obtained Feb. 3, 2015 (CAS Registry No. 1383982-63-5).

Thompson et al., "Protein Conformational Misfolding and Amyloid Formation: Characteristics of a New Class of Disorders that Include Alzheimer's and Prion Diseases," Current Medicinal Chemistry, Oct. 2002, 9(19), pp. 1751-1762.

Berge et al., "Pharmaceutical Salts," Journal of Pharmaceutical Sciences, vol. 66, No. 1, pp. 1-19, Jan. 1977.

Bighley et al, "Salt Forms of Drugs and Absorption," Encyclopaedia of Pharmaceutical Technology, vol. 13. New York: Marcell-Decker, Inc. pp. 453-499, 1996.

Elder et al., "The Utility of Sulfonate Salts in Drug Development," Journal of Pharmaceutical Sciences, vol. 99, No. 7, pp. 2948-2961, Jul. 2010.

Gottfries et al., "Membrane Components Separate Early-Onset Alzheimer's Disease From Senile Dementia of the Alzheimer Type," International Psychogeriatrics, vol. 8, No. 3, pp. 365-372, 1996.

Kumar et al., "Effect of Counterions on Physicochemical Properties of Prazosin Salts," AAPS PharmSciTech, 2013, vol. 14(1), pp. 141-150.

Makary et al., "Principles of salt formation," UK Journal of Pharmaceutical and Biosciences, vol. 2(4), Jan. 4, 2014.

Patel et al., "Pharmaceutical salts: a formulation trick or a clinical conundrum," The British Journal of Cardiology, vol. 16, No. 6, pp. 281-286, Nov./Dec. 2009.

Remenar et al., "Salt Selection and Simultaneous Polymorphism Assessment via High-Throughput Crystallization: The Case of Sertraline," Organic Process Research & Development 2003, 7, 990-996.

Rossor et al., "Neurochemical characteristics of early and late onset types of Alzheimer's disease," British Medical Journal, vol. 288, pp. 961-964, Mar. 31, 1984.

Stahl et al., Handbook of Pharmaceutical Salts Properties, Selection, and Use, Internatkional Union of Pure and Applied Chemistry (IUPAC), Second, Revised Edition, 2011, p. 336.

* cited by examiner

MONO-FLUORO BETA-SECRETASE INHIBITORS

CROSS-REFERENCE TO RELATED APPLICATIONS

This application is a national stage application under 35 U.S.C. §371 of International Patent Application PCT/GB2012/052510, filed on Oct. 10, 2012, which claims the benefit of and priority from U.S. Provisional Patent Application 61/545,334, filed on Oct. 10, 2011. Each of the foregoing applications is incorporated herein by reference in their entirety.

FIELD OF THE INVENTION

The present invention relates to novel compounds and therapeutically acceptable salts thereof, their pharmaceutical compositions, processes for making them and their use as medicaments for treatment and/or prevention of various diseases. In particular the invention relates to compounds, which are inhibitors of β-secretase and hence inhibit the formation of amyloid β (Aβ) peptides and will be used for treatment and/or prevention of Aβ-related pathologies such as Alzheimer's disease, Down's syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer's disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration.

BACKGROUND OF THE INVENTION

The prime neuropathological event distinguishing Alzheimer's disease (AD) is deposition of the 40-42 residue amyloid β-peptide (Aβ) in brain parenchyma and cerebral vessels. A large body of genetic, biochemical and in vivo data support a pivotal role for Aβ in the pathological cascade that eventually leads to AD. Patients usually present early symptoms (commonly memory loss) in their sixth or seventh decades of life. The disease progresses with increasing dementia and elevated deposition of Aβ. In parallel, a hyperphosphorylated form of the microtubule-associated protein tau accumulates within neurons, leading to a plethora of deleterious effects on neuronal function. The prevailing working hypothesis regarding the temporal relationship between Aβ and tau pathologies states that Aβ deposition precedes tau aggregation in humans and animal models of the disease. Within this context, it is worth noting that the exact molecular nature of Aβ, mediating this pathological function is presently an issue under intense study. Most likely, there is a continuum of toxic species ranging from lower order Aβ oligomers to supramolecular assemblies such as Aβ fibrils.

The Aβ peptide is an integral fragment of the Type I protein APP (Aβ amyloid precursor protein), a protein ubiquitously expressed in human tissues. Since soluble Aβ can be found in both plasma and cerebrospinal fluid (CSF), and in the medium from cultured cells, APP has to undergo proteolysis. There are three main cleavages of APP that are relevant to the pathobiology of AD, the so-called α-, β-, and γ-cleavages. The α-cleavage, which occurs roughly in the middle of the Aβ domain in APP is executed by the metalloproteases ADAM10 or ADAM17 (the latter also known as TACE). The β-cleavage, occurring at the N terminus of Aβ, is generated by the transmembrane aspartyl protease Beta site APP Cleaving Enzyme1 (BACE1). The γ-cleavage, generating the Aβ C termini and subsequent release of the peptide, is effected by a multi-subunit aspartyl protease named γ-secretase. ADAM10/17 cleavage followed by γ-secretase cleavage results in the release of the soluble p3 peptide, an N-terminally truncated Aβ fragment that fails to form amyloid deposits in humans. This proteolytic route is commonly referred to as the non-amyloidogenic pathway. Consecutive cleavages by BACE1 and γ-secretase generates the intact Aβ peptide, hence this processing scheme has been termed the amyloidogenic pathway. With this knowledge at hand, it is possible to envision two possible avenues of lowering Aβ production: stimulating non-amyloidogenic processing, or inhibit or modulate amyloidogenic processing. This application focuses on the latter strategy, inhibition or modulation of amyloidogenic processing.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders (Varghese, J., et al, Journal of Medicinal Chemistry, 2003, 46, 4625-4630). β-amyloid deposits are predominately an aggregate of Aβ peptide, which in turn is a product of the proteolysis of amyloid precursor protein (APP). More specifically, Aβ peptide results from the cleavage of APP at the C-terminus by one or more γ-secretases, and at the N-terminus by β-secretase enzyme (BACE), also known as aspartyl protease or Asp2 or Beta site APP Cleaving Enzyme (BACE), as part of the β-amyloidogenic pathway.

BACE activity is correlated directly to the generation of Aβ peptide from APP (Sinha, et al, Nature, 1999, 402, 537-540), and studies increasingly indicate that the inhibition of BACE inhibits the production of Aβ peptide (Roberds, S. L., et al, Human Molecular Genetics, 2001, 10, 1317-1324). BACE is a membrane bound type 1 protein that is synthesized as a partially active proenzyme, and is abundantly expressed in brain tissue. It is thought to represent the major β-secretase activity, and is considered to be the rate-limiting step in the production of amyloid-β-peptide (Aβ).

Drugs that reduce or block BACE activity should therefore reduce Aβ levels and levels of fragments of Aβ in the brain, or elsewhere where Aβ or fragments thereof deposit, and thus slow the formation of amyloid plaques and the progression of AD or other maladies involving deposition of Aβ or fragments thereof. BACE is therefore an important candidate for the development of drugs as a treatment and/or prophylaxis of Aβ-related pathologies such as Down's syndrome, β-amyloid angiopathy such as but not limited to cerebral amyloid angiopathy or hereditary cerebral hemorrhage, disorders associated with cognitive impairment such as but not limited to MCI ("mild cognitive impairment"), Alzheimer's disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration.

It would therefore be useful to inhibit the deposition of Aβ and portions thereof by inhibiting BACE through inhibitors such as the compounds provided herein.

DESCRIPTION OF THE INVENTION

The present invention is directed to compounds according to formula (I):

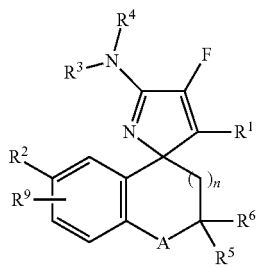

wherein
A is —O—, —CH$_2$—, —CH$_2$CH$_2$—, —OCH$_2$—, —CH$_2$O—, or —CF$_2$—;
n is 0 or 1;
$R^1$ is H, C$_{1-6}$alkyl or C$_{0-6}$alkylC$_{3-6}$cycloalkyl;
$R^2$ is C$_{0-6}$alkylaryl, C$_{0-6}$alkylheteroaryl, C$_{2-6}$alkynyl, C$_{1-6}$alkyl, halogen, cyano, or OR$^8$, wherein said C$_{0-6}$alkylaryl, C$_{0-6}$alkylheteroaryl, C$_{2-6}$alkynyl, or C$_{1-6}$alkyl is optionally substituted with one to three R$^7$;
$R^3$ is H;
$R^4$ is H;
$R^5$ and $R^6$ is independently hydrogen, heterocyclyl, C$_{3-6}$cycloalkyl, aryl, heteroaryl or C$_{1-6}$alkyl, wherein said heterocyclyl, C$_{3-6}$cycloalkyl, aryl, heteroaryl or C$_{1-6}$alkyl is optionally substituted with one or two substituents independently selected from halogen, C$_{1-6}$alkyl, C$_{1-6}$haloalkyl, cyano, or OR$^8$; provided that R$^5$ and R$^6$ are not hydrogen at the same time;
or R$^5$ and R$^6$ together with the carbon to which they are attached, form a ring B, which is a 3-7 membered cycloalkyl or heterocyclyl monocyclic ring, or a 7-12 membered bicyclic cycloalkyl or heterocyclyl ring; and wherein ring B is optionally substituted by one or more substituents independently selected from oxo, halogen, C$_{1-6}$alkyl, C$_{1-6}$haloalkyl, cyano, or OR$^8$; and ring B is optionally fused with an aryl or heteroaryl to form a bi- or polycyclic system;
$R^7$ is independently C$_{1-6}$alkyl, halogen, cyano, C$_{0-6}$alkylaryl, C$_{0-6}$alkylheteroaryl, C$_{0-6}$alkylC$_{3-6}$cycloalkyl, OC$_{1-6}$alkyl, or C$_{2-6}$alkynyl, wherein said C$_{1-6}$alkyl, C$_{0-6}$alkylaryl, C$_{0-6}$alkylheteroaryl, C$_{0-6}$alkylC$_{3-6}$cycloalkyl, OC$_{1-6}$alkyl, or C$_{2-6}$alkynyl is optionally substituted with 1-3 substituents independently selected from halogen, cyano, C$_{1-6}$alkyl, C$_{0-6}$alkylC$_{3-6}$cycloalkyl, C$_{1-6}$haloalkyl, OC$_{1-6}$alkyl, and OC$_{1-6}$haloalkyl;
$R^8$ is independently hydrogen, C$_{1-6}$alkyl, C$_{0-6}$alkyl C$_{3-6}$cycloalkyl, C$_{2-6}$alkynyl, aryl or heteroaryl; wherein said C$_{1-6}$alkyl, aryl or heteroaryl is optionally substituted with one or more substituents independently selected from halogen, cyano, and C$_{1-6}$alkyl; and
$R^9$ is H, F, OH, CH$_3$, Cl or OCH$_3$;
$R^9$ is one or more substituents independently selected from H, F, OH, CH$_3$, Cl and OCH$_3$;
as a free base or a pharmaceutically acceptable salt thereof.
In one embodiment of the present invention, A is —O—, —CH$_2$—, —OCH$_2$— or —CH$_2$O—.

In one embodiment of the present invention, R$^2$ is C$_{0-6}$alkylaryl, C$_{0-6}$alkylheteroaryl or C$_{2-6}$alkynyl, wherein said C$_{0-6}$alkylaryl, C$_{0-6}$alkylheteroaryl or C$_{2-6}$alkynyl is optionally substituted with one to three R$^7$.
In one embodiment of the present invention, R$^5$ and R$^6$ are independently hydrogen or heterocyclyl wherein said heterocyclyl is optionally substituted with one or two substituents independently selected from C$_{1-6}$alkyl or OR$^8$; provided that R$^5$ and R$^6$ are not both hydrogen.
In one embodiment of the present invention, R$^5$ and R$^6$ together with the carbon to which they are attached, form a ring B, which is a 3-7 membered cycloalkyl or heterocyclyl monocyclic ring, or a 9-12 membered bicyclic cycloalkyl or heterocyclyl ring; and wherein ring B is optionally substituted by one or two substituents independently selected from oxo, halogen, C$_{1-6}$alkyl or OR$^8$; and ring B is optionally fused with an aryl or heteroaryl to form a bi- or polycyclic system.
In one embodiment of the present invention, R$^7$ is C$_{1-6}$alkyl, halogen, cyano, OC$_{1-6}$alkyl or C$_{2-6}$alkynyl, wherein said C$_{1-6}$alkyl, OC$_{1-6}$alkyl or C$_{2-6}$alkynyl is optionally substituted with 1-3 substituents independently selected from halogen, cyano, C$_{1-6}$alkyl, C$_{0-6}$alkylC$_{3-6}$cycloalkyl, C$_{1-6}$haloalkyl, OC$_{1-6}$alkyl and OC$_{1-6}$haloalkyl.
In one embodiment of the present invention, R$^8$ is independently C$_{1-6}$alkyl or C$_{2-6}$alkynyl, wherein said C$_{1-6}$alkyl is optionally substituted with one or more halogen.
In one embodiment of the present invention, R$^9$ is H or F.
In one embodiment of the present invention,
A is —O—, —CH$_2$—, —OCH$_2$— or —CH$_2$O—;
n is 0 or 1;
$R^2$ is C$_{0-6}$alkylaryl, C$_{0-6}$alkylheteroaryl or C$_{2-6}$alkynyl, wherein said C$_{0-6}$alkylaryl, C$_{0-6}$alkylheteroaryl or C$_{2-6}$alkynyl is optionally substituted with one to three R$^7$;
$R^5$ and $R^6$ are independently hydrogen or heterocyclyl wherein said heterocyclyl is optionally substituted with one or two substituents independently selected from C$_{1-6}$alkyl or OR$^8$ provided that R$^5$ and R$^6$ are not hydrogen at the same time;
or R$^5$ and R$^6$ together with the carbon to which they are attached, form a ring B, which is a 3-7 membered cycloalkyl or heterocyclyl monocyclic ring, or a 9-12 membered bicyclic cycloalkyl or heterocyclyl ring; and wherein ring B is optionally substituted by one or two substituents independently selected from oxo, halogen, C$_{1-6}$alkyl or OR$^8$; and ring B is optionally fused with an aryl or heteroaryl to form a bi- or polycyclic system;
$R^7$ is C$_{1-6}$alkyl, halogen, cyano, OC$_{1-6}$alkyl or C$_{2-6}$alkynyl, wherein said C$_{1-6}$alkyl, OC$_{1-6}$alkyl or C$_{2-6}$alkynyl is optionally substituted with 1-3 substituents independently selected from halogen, cyano, C$_{1-6}$alkyl, C$_{0-6}$alkylC$_{3-6}$cycloalkyl, C$_{1-6}$haloalkyl, OC$_{1-6}$alkyl and OC$_{1-6}$haloalkyl;
$R^8$ is independently C$_{1-6}$alkyl or C$_{2-6}$alkynyl, wherein said C$_{1-6}$alkyl is optionally substituted with one or more halogen; and
$R^9$ is H, F, OH, CH$_3$, Cl, or OR$^8$.
In one embodiment of the present invention,
A is —O—, —CH$_2$—, —OCH$_2$— or —CH$_2$O—;
n is 0 or 1;
$R^2$ is aryl, heteroaryl or C$_{2-6}$alkynyl, wherein said aryl, heteroaryl or C$_{2-6}$alkynyl is optionally substituted with one to three R$^7$;
$R^5$ and $R^6$ is independently hydrogen or heterocyclyl, wherein said heterocyclyl is optionally substituted with two substituents independently selected from C$_{1-6}$alkyl; provided that R$^5$ and R$^6$ are not hydrogen at the same time;

or R⁵ and R⁶ together with the carbon to which they are attached, form a ring B, which is a 3-7 membered cycloalkyl or heterocyclyl monocyclic ring, or a 9-12 membered bicyclic cycloalkyl or heterocyclyl ring; and wherein ring B is optionally substituted by one or two substituents independently selected from oxo, halogen, $C_{1-6}$alkyl or $OR^8$; and ring B is optionally fused with an aryl or heteroaryl to form a bicyclic system;

$R^7$ is $C_{1-6}$alkyl, halogen, cyano, $OC_{1-6}$alkyl or $C_{2-6}$alkynyl, wherein said $C_{1-6}$alkyl, $OC_{1-6}$alkyl or $C_{2-6}$alkynyl is optionally substituted with 1-3 substituents independently selected from halogen, cyano, $C_{1-6}$alkyl, $C_{0-6}$alkyl$C_{3-6}$cycloalkyl, $C_{1-6}$haloalkyl, $OC_{1-6}$alkyl and $OC_{1-6}$haloalkyl;

$R^8$ is independently $C_{1-6}$alkyl or $C_{2-6}$alkynyl, wherein said $C_{1-6}$alkyl is optionally substituted with one or more halogen; and $R^9$ is H, F, OH, $CH_3$, Cl or $OR^8$.

In one embodiment of the present invention,
A is —O—, —CH₂—, —OCH₂— or —CH₂O—;
n is 0;
$R^2$ is aryl, heteroaryl or $C_{2-6}$alkynyl, wherein said aryl, heteroaryl or $C_{2-6}$alkynyl is optionally substituted with one to three $R^7$;
$R^5$ and $R^6$ together with the carbon to which they are attached form a cyclohexyl ring, which is substituted with $OR^8$;
$R^7$ is $C_{1-3}$alkyl, halogen, cyano, $OC_{1-3}$alkyl or $C_{2-6}$alkynyl, wherein $C_{1-3}$alkyl is optionally substituted with $OC_{1-3}$alkyl;
$R^8$ is $C_{1-3}$alkyl;
$R^9$ is H or F.

In one embodiment of the present invention,
A is —O—, —CH₂—, —OCH₂— or —CH₂O—;
n is 0;
$R^2$ is phenyl, pyridinyl or pyrimidinyl, wherein said phenyl, pyridinyl or pyrimidinyl is optionally substituted with one or two $R^7$;
$R^5$ and $R^6$ together with the carbon to which they are attached form a cyclohexyl ring, which is substituted with methoxy;
$R^7$ is chloro, fluoro, cyano, methoxy, methoxymethyl or prop-1-yn-1-yl; and
$R^9$ is H or F.

In one embodiment of the present invention,
A is —O—, —CH₂—;
n is 0;
$R^2$ is phenyl, pyridinyl or pyrimidinyl, wherein said phenyl, pyridinyl or pyrimidinyl is optionally substituted with one or two $R^7$;
$R^5$ and $R^6$ together with the carbon to which they are attached form a cyclohexyl ring, which is substituted with methoxy;
$R^7$ is fluoro, cyano, or prop-1-yn-1-yl; and
$R^9$ is H or F.

One embodiment of the present invention is a compound selected from:
(1r,4r)-4"-fluoro-4-methoxy-6'-(pyrimidin-5-yl)-3'H-dispiro[cyclohexane-1,2'-indene-1,2"-pyrrol]-5"amine;
(1s,4s)-4"-Fluoro-4-methoxy-6'-(pyrimidin-5-yl)-3'H-dispiro[cyclohexane-1,2'-indene-1,2"-pyrrol]-5"amine;
(1r,4r)-4"-Fluoro-4-methoxy-6'-[5-(prop-1-yn-1-yl)pyridin-3-yl]-3'H-dispiro[cyclohexane-1,2'-indene-1',2"-pyrrol]-5"amine;
(1s,4s)-4"-Fluoro-4-methoxy-6'-[5-(prop-1-yn-1-yl)pyridin-3-yl]-3'H-dispiro[cyclohexane-1,2'-indene-1',2"-pyrrol]-5"amine;
3-[(1s,4s)-5"-Amino-4"-fluoro-4-methoxydispiro[cyclohexane-1,2'-[1]benzofuran-3',2"-pyrrol]-5'-yl]-5-fluorobenzonitrile;
4'-Fluoro-3,3-dimethyl-6-(pyrimidin-5-yl)spiro[chroman-4,2'-pyrrol]-5'-amine;
4'-Fluoro-6-(5-fluoropyridin-3-yl)-3,3-dimethylspiro[chroman-4,2'-pyrrol]-5'-amine;
6-(3,5-Difluorophenyl)-4'-fluoro-3,3-dimethylspiro[chroman-4,2'-pyrrol]-5'-amine;
4'-Fluoro-2,2-dimethyl-6-(pyrimidin-5-yl)-2,3-dihydrospiro[indene-1,2'-pyrrol]-5'-amine;
4"-Fluoro-6'-(3-fluoropropoxy)-4-[(2H3)methyloxy]-3'H-dispiro[cyclohexane-1,2'-indene-1',2"-pyrrol]-5"-amine, isomer 1, and
4"-Fluoro-6'-(3-fluoropropoxy)-4-[(2H3)methyloxy]-3'H-dispiro[cyclohexane-1,2'-indene-1',2"-pyrrol]-5"-amine, isomer 2.

Other compounds of the invention are selected from:
4"-fluoro-4-methoxy-6'-(pyridin-3-yl)-3'H-dispiro[cyclohexane-1,2'-indene-1',2"-pyrrol]-5"-amine;
4"-fluoro-6'-(5-fluoropyridin-3-yl)-4-methoxy-3'H-dispiro[cyclohexane-1,2'-indene-1',2"-pyrrol]-5"-amine;
6'-(5-chloropyridin-3-yl)-4"-fluoro-4-methoxy-3'H-dispiro[cyclohexane-1,2'-indene-1',2"-pyrrol]-5"-amine;
6'-(5-chloro-6-methylpyridin-3-yl)-4"-fluoro-4-methoxy-3'H-dispiro[cyclohexane-1,2'-indene-1',2"-pyrrol]-5"-amine;
4"-fluoro-4-methoxy-6'-(5-methylpyridin-3-yl)-3'H-dispiro[cyclohexane-1,2'-indene-1',2"-pyrrol]-5"-amine;
4"-fluoro-4-methoxy-6'-(3-methoxyphenyl)-3'H-dispiro[cyclohexane-1,2'-indene-1',2"-pyrrol]-5"-amine;
6'-(3-chlorophenyl)-4"-fluoro-4-methoxy-3'H-dispiro[cyclohexane-1,2'-indene-1',2"-pyrrol]-5"-amine;
3-(5"-amino-4"-fluoro-4-methoxy-3'H-dispiro[cyclohexane-1,2'-indene-1',2"-pyrrol]-6'-yl)-5-fluorobenzonitrile;
3-(5"-amino-4"-fluoro-4-methoxy-3'H-dispiro[cyclohexane-1,2'-indene-1',2"-pyrrol]-6'-yl)-5-chlorobenzonitrile;
4"-fluoro-4-methoxy-6'-phenyl-3'H-dispiro[cyclohexane-1,2'-indene-1',2"-pyrrol]-5"-amine;
4"-fluoro-6'-[3-fluoro-5-(methoxymethyl)phenyl]-4-methoxy-3'H-dispiro[cyclohexane-1,2'-indene-1',2"-pyrrol]-5"-amine;
6'-[3-chloro-5-(methoxymethyl)phenyl]-4"-fluoro-4-methoxy-3'H-dispiro[cyclohexane-1,2'-indene-1',2"-pyrrol]-5"-amine;
3-(5"-amino-4"-fluoro-4-methoxy-3'H-dispiro[cyclohexane-1,2'-indene-1',2"-pyrrol]-6'-yl)-5-(methoxymethyl)benzonitrile;
4"-fluoro-4-methoxy-4-methyl-6'-(pyrimidin-5-yl)-3'H-dispiro[cyclohexane-1,2'-indene-1',2"-pyrrol]-5"-amine;
4-(difluoromethoxy)-4"-fluoro-6'-(pyrimidin-5-yl)-3'H-dispiro[cyclohexane-1,2'-indene-1',2"-pyrrol]-5"-amine
4"-fluoro-4-methoxy-5'-(pyrimidin-5-yl)dispiro[cyclohexane-1,2'-[1]benzofuran-3',2"-pyrrol]-5"-amine;
4"-fluoro-4-methoxy-5'-(pyridin-3-yl)dispiro[cyclohexane-1,2'-[1]benzofuran-3',2"-pyrrol]-5"-amine;
4"-fluoro-5'-(5-fluoropyridin-3-yl)-4-methoxydispiro[cyclohexane-1,2'-[1]benzo furan-3',2"-pyrrol]-5"-amine;
5'-(5-chloropyridin-3-yl)-4"-fluoro-4-methoxydispiro[cyclohexane-1,2'-[1]benzo furan-3',2"-pyrrol]-5"-amine;
5'-(5-chloro-6-methylpyridin-3-yl)-4"-fluoro-4-methoxydispiro[cyclohexane-1,2'-[1]benzofuran-3',2"-pyrrol]-5"-amine;
4"-fluoro-4-methoxy-5'-(5-methylpyridin-3-yl)dispiro[cyclohexane-1,2'-[1]benzo furan-3',2"-pyrrol]-5"-amine;

4"-fluoro-4-methoxy-5'-(3-methoxyphenyl)dispiro[cyclohexane-1,2'-[1]benzo furan-3',2"-pyrrol]-5"-amine;

5'-(3-chlorophenyl)-4"-fluoro-4-methoxydispiro[cyclohexane-1,2'-[1]benzofuran-3',2"-pyrrol]-5"-amine;

3-(5"-amino-4"-fluoro-4-methoxydispiro[cyclohexane-1,2'-[1]benzofuran-3',2"-pyrrol]-5'-yl)-5-chlorobenzonitrile;

4"-fluoro-4-methoxy-5'-phenyldispiro[cyclohexane-1,2'-[1]benzofuran-3',2"-pyrrol]-5"-amine;

4"-fluoro-5'-[3-fluoro-5-(methoxymethyl)phenyl]-4-methoxydispiro[cyclohexane-1,2'-[1]benzofuran-3',2"-pyrrol]-5"-amine;

5'-[3-chloro-5-(methoxymethyl)phenyl]-4"-fluoro-4-methoxydispiro[cyclohexane-1,2'-[1]benzofuran-3',2"-pyrrol]-5"-amine;

3-(5"-amino-4"-fluoro-4-methoxydispiro[cyclohexane-1,2'-[1]benzofuran-3',2"-pyrrol]-5'-yl)-5-(methoxymethyl)benzonitrile;

4"-fluoro-4-methoxy-5'-[5-(prop-1-yn-1-yl)pyridin-3-yl]dispiro[cyclohexane-1,2'-[1]benzofuran-3',2"-pyrrol]-5"-amine;

4"-fluoro-4-methoxy-4-methyl-5'-(pyrimidin-5-yl)dispiro[cyclohexane-1,2'-[1]benzofuran-3',2"-pyrrol]-5"-amine; and 4-(difluoromethoxy)-4"-fluoro-5'-(pyrimidin-5-yl)dispiro[cyclohexane-1,2'-[1]benzofuran-3',2"-pyrrol]-5"-amine, as a free base or a pharmaceutically acceptable salt thereof.

The present invention relates to the use of compounds of formula (I) as hereinbefore defined as well as to the salts thereof. Salts for use in pharmaceutical compositions will be pharmaceutically acceptable salts, but other salts may be useful in the production of the compounds of formula (I).

The compounds of the formula (I) may be administered in the form of a prodrug which is broken down in the human or animal body to give a compound of the formula (I). Examples of prodrugs include in vivo hydrolysable esters of a compound of the formula (I). An in vivo hydrolysable (or cleavable) ester of a compound of the formula (I) that contains a carboxy or a hydroxy group is, for example, a pharmaceutically acceptable ester which is hydrolysed in the human or animal body to produce the parent acid or alcohol. Various forms of prodrugs are known in the art.

The definitions set forth in this application are intended to clarify terms used throughout this application. The term "herein" means the entire application.

A variety of compounds in the present invention may exist in particular geometric or stereoisomeric forms. The present invention takes into account all such compounds, including tautomers, cis- and trans isomers, R- and S-enantiomers, diastereomers, (D)-isomers, (L)-isomers, the racemic mixtures thereof, and other mixtures thereof, as being covered within the scope of this invention. Additional asymmetric carbon atoms may be present in a substituent such as an alkyl group. All such isomers, as well as mixtures thereof, are intended to be included in this invention. The compounds herein described may have asymmetric centers. Compounds of the present invention containing an asymmetrically substituted atom may be isolated in optically active or racemic forms. It is well known in the art how to prepare optically active forms, such as by resolution of racemic forms, by synthesis from optically active starting materials, or synthesis using optically active reagents. When required, separation of the racemic material can be achieved by methods known in the art. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents, positions of substituents and/or variables are permissible only if such combinations result in stable compounds.

As used in this application, the term "optionally substituted" means that substitution is optional and therefore it is possible for the designated atom or moiety to be unsubstituted.

As used herein, "alkyl", used alone or as a suffix or prefix, is intended to include both branched and straight chain saturated aliphatic hydrocarbon groups having from 1 to 12 carbon atoms or if a specified number of carbon atoms is provided then that specific number would be intended. For example "$C_{0-6}$alkyl" denotes alkyl having 0, 1, 2, 3, 4, 5 or 6 carbon atoms. Examples of alkyl include, but are not limited to, methyl, ethyl, n-propyl, i-propyl, n-butyl, i-butyl, sec-butyl, t-butyl, pentyl, and hexyl. In the case where a subscript is the integer 0 (zero) the group to which the subscript refers to indicates that the group may be absent, i.e. there is a direct bond between the groups.

As used herein, "alkynyl" used alone or as a suffix or prefix is intended to include to include both branched and straight-chain alkynyl or olefin containing aliphatic hydrocarbon groups having from 2 to 12 carbon atoms or if a specified number of carbon atoms is provided then that specific number would be intended. For example ethynyl, propynyl (e.g. 1-propynyl, 2-propynyl), 3-butynyl, pentynyl, hexynyl and 1-methylpent-2-ynyl.

As used herein, "aromatic" refers to hydrocarbonyl groups having one or more unsaturated carbon ring(s) having aromatic characters, (e.g. 4n+2 delocalized electrons) and comprising up to 14 carbon atoms. In addition "heteroaromatic" refers to groups having one or more unsaturated rings containing carbon and one or more heteroatoms such as nitrogen, oxygen or sulphur having aromatic character (e.g. 4n+2 delocalized electrons).

As used herein, the term "aryl" refers to an aromatic ring structure made up of from 5 to 14 carbon atoms. Ring structures containing 5, 6, 7 and 8 carbon atoms would be single-ring aromatic groups, for example, phenyl. Ring structures containing 8, 9, 10, 11, 12, 13, or 14 would be polycyclic, for example naphthyl. The aromatic ring can be substituted at one or more ring positions with such substituents as described above. The term "aryl" also includes polycyclic ring systems having two or more cyclic rings in which two or more carbons are common to two adjoining rings (the rings are "fused rings") wherein at least one of the rings is aromatic, for example, the other cyclic rings can be cycloalkyls, cycloalkenyls, cycloalkynyls, aryls and/or heterocyclyls. Examples of polycyclic rings include, but are not limited to, 2,3-dihydro-1,4-benzodioxine and 2,3-dihydro-1-benzofuran.

As used herein, the terms "cycloalkyl" or "carbocyclyl" are intended to include saturated ring groups, having the specified number of carbon atoms. These may include fused or bridged polycyclic systems. Cycloalkyls have from 3 to 14 carbon atoms in their ring structure. In one embodiment, cycloalkyls have 3, 4, 5, or 6 carbons in the ring structure. For example, "$C_{3-6}$cycloalkyl" denotes such groups as cyclopropyl, cyclobutyl, cyclopentyl, or cyclohexyl.

As used herein, the term "cycloalkenyl" is intended to include unsaturated ring groups, having the specified number of carbon atoms. These may include fused or bridged polycyclic systems. Cycloalkenyls may have from 3 to 10 carbon atoms in their ring structure. In one embodiment, cycloalkenyls have 3, 4, 5, or 6 carbons in the ring structure. For example, "$C_{3-6}$cycloalkenyl" denotes such groups as cyclopropenyl, cyclobutenyl, cyclopentenyl, or cyclohexenyl.

As used herein, "halo" or "halogen" refers to fluoro, chloro, bromo, and iodo.

"Counterion" is used to represent a small, negatively or positively charged species such as chloride, bromide, hydroxide, acetate, sulfate, tosylate, benezensulfonate, ammonium, lithium ion and sodium ion and the like.

As used herein, the term "heterocyclyl" or "heterocyclic" or "heterocycle" refers to a saturated, unsaturated or partially saturated, monocyclic, bicyclic or tricyclic ring (unless otherwise stated) containing 3 to 20 atoms of which 1, 2, 3, 4 or 5 ring atoms are chosen from nitrogen, sulphur or oxygen, which may, unless otherwise specified, be carbon or nitrogen linked, wherein a —$CH_2$— group is optionally be replaced by a —C(O)—; and where unless stated to the contrary a ring nitrogen or sulphur atom is optionally oxidised to form the N-oxide or S-oxide(s) or a ring nitrogen is optionally quarternized; wherein a ring NH is optionally substituted with acetyl, formyl, methyl or mesyl; and a ring is optionally substituted with one or more halo. It is understood that when the total number of S and O atoms in the heterocyclyl exceeds 1, then these heteroatoms are not adjacent to one another. If the said heterocyclyl group is bi- or tricyclic then at least one of the rings may optionally be a heteroaromatic or aromatic ring provided that at least one of the rings is non-heteroaromatic. If the said heterocyclyl group is monocyclic then it must not be aromatic. Examples of heterocyclyls include, but are not limited to, piperidinyl, N-acetylpiperidinyl, N-methylpiperidinyl, N-formylpiperazinyl, N-mesylpiperazinyl, homopiperazinyl, piperazinyl, azetidinyl, oxetanyl, morpholinyl, tetrahydroisoquinolinyl, tetrahydroquinolinyl, indolinyl, tetrahydropyranyl, dihydro-2H-pyranyl, tetrahydrofuranyl, tetrahydro-thiopyranyl, tetrahydro-thiopyran 1-oxide, tetrahydro-thiopyran 1,1-dioxide, 1H-pyridin-2-one, and 2,5-dioxoimidazolidinyl.

As used herein, "heteroaryl" refers to a heteroaromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl (i.e., pyridinyl), pyrimidinyl, pyrazinyl, pyridazinyl, triazinyl, furyl (i.e. furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, benzoxazolyl, aza-benzoxazolyl imidazothiazolyl, benzo[1,4]dioxinyl, benzo[1,3]dioxolyl and the like. In some embodiments, the heteroaryl group has from 1 to 20 carbon atoms, and in further embodiments from 3 to 20 carbon atoms. In some embodiments, the heteroaryl group contains 3 to 14, 4 to 14, 3 to 7, or 5 to 6 ring-forming atoms. In some embodiments, the heteroaryl group has 1 to 4, 1 to 3, or 1 to 2 heteroatoms. In some embodiments, the heteroaryl group has 1 heteroatom.

As used herein, "haloalkyl", used alone or as a suffix or prefix, is intended to include both branched and straight chain saturated aliphatic hydrocarbon groups, having at least one halogen substituent and having from 1 to 12 carbon atoms or if a specified number of carbon atoms is provided then that specific number would be intended. For example "$C_{0-6}$haloalkyl" denotes alkyl having 0, 1, 2, 3, 4, 5 or 6 carbon atoms. Examples of haloalkyl include, but are not limited to, fluoromethyl, difluoromethyl, trifluoromethyl, chlorofluoromethyl, 1-fluoroethyl, 3-fluoropropyl, 2-chloropropyl, 3,4-difluorobutyl.

As used herein, the phrase "protecting group" means temporary substituents which protect a potentially reactive functional group from undesired chemical transformations. Examples of such protecting groups include esters of carboxylic acids, silyl ethers of alcohols, and acetals and ketals of aldehydes and ketones respectively. The field of protecting group chemistry has been reviewed (Greene, T. W.; Wuts, P. G. M. *Protective Groups in Organic Synthesis, 3$^{rd}$* ed.; Wiley: New York, 1999).

As used herein, "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the non-toxic salts or the quaternary ammonium salts of the parent compound formed, for example, from non-toxic inorganic or organic acids. For example, such non-toxic salts include those derived from inorganic acids such as hydrochloric acid.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like diethyl ether, ethyl acetate, ethanol, isopropanol, or acetonitrile are used.

The present invention further includes all tautomeric forms of compounds of the invention.

As used herein, "tautomer" means other structural isomers that exist in equilibrium resulting from the migration of a hydrogen atom. For example, keto-enol tautomerism where the resulting compound has the properties of both a ketone and an unsaturated alcohol. Other examples of tautomerism include 2H-imidazole-4-amine and its tautomer 1,2-dihydroimidazol-5-imine, and 2H-imidazol-4-thiol and its tautomer 1,2-dihydroimidazol-5-thione. It is understood that in compound representations throughout this description, only one of the possible tautomers of the compound is drawn or named.

As used herein "stable compound" and "stable structure" are meant to indicate a compound that is sufficiently robust to survive isolation to a useful degree of purity from a reaction mixture, and formulation into an efficacious therapeutic agent.

Compounds of the invention further include hydrates and solvates.

The present invention further includes isotopically-labelled compounds of the invention. An "isotopically" or "radio-labelled" compound is a compound of the invention where one or more atoms are replaced or substituted by an atom having an atomic mass or mass number different from the atomic mass or mass number typically found in nature (i.e., naturally occurring). Suitable isotopes that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}G$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labelled compounds will depend on the specific application of that radio-labelled compound. For example, for in vitro receptor labelling and competition assays, compounds that incorporate $^{3}H$, $^{14}C$, $^{82}Br$, $^{125}I$, $^{131}I$ or $^{35}S$ will generally be most useful. For radio-imaging applications $^{11}C$, $^{18}F$, $^{125}I$, $^{123}I$, $^{131}I$, $^{75}Br$, $^{76}Br$ or $^{77}Br$ will generally be most useful.

It is understood that a "radio-labelled compound" is a compound that has incorporated at least one radionuclide. In some embodiments the radionuclide is selected from the group consisting of $^{3}H$, $^{14}C$, $^{125}I$, $^{35}S$ and $^{82}Br$.

Compounds of the present invention may be administered orally, parenteral, buccal, vaginal, rectal, inhalation, insufflation, sublingually, intramuscularly, subcutaneously, topically, intranasally, intraperitoneally, intrathoracically, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

The quantity of the compound to be administered will vary for the patient being treated and will vary from about 100 ng/kg of body weight to 100 mg/kg of body weight per day. For instance, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention.

In another aspect of the invention, there is provided that the compounds of the invention, or a pharmaceutically acceptable salt thereof, can be used as medicaments, e.g. to treat or prevent Aβ-related pathologies.

In another aspect of the invention, there is provided that the compounds of the invention, or a pharmaceutically acceptable salt thereof, can be used for the manufacture of a medicament to treat or prevent Aβ-related pathologies.

In another aspect of the invention, there is provided a method for the treatment of Aβ-related pathologies, comprising administering a therapeutically effective amount of a compound of Formula (I), or a pharmaceutically acceptable salt thereof, to a subject, such as a mammal or a human being, in need thereof.

The compounds of the invention and their pharmaceutically acceptable salts thereby provides methods of treatment of Aβ-related pathologies, such as, but not limited to, Alzheimer's disease, Down's syndrome, β-amyloid angiopathy, cerebral amyloid angiopathy, hereditary cerebral hemorrhage, a disorder associated with cognitive impairment, MCI ("mild cognitive impairment"), memory loss, attention deficit symptoms associated with Alzheimer's disease, neurodegeneration associated with Alzheimer's disease, dementia of mixed vascular origin, dementia of degenerative origin, pre-senile dementia, senile dementia, dementia associated with Parkinson's disease, progressive supranuclear palsy traumatic brain injury and cortical basal degeneration.

In another aspect of the invention, there is provided a pharmaceutical composition comprising as active ingredient a therapeutically effective amount of a compound according formula (I) in association with pharmaceutically acceptable excipients, carriers or diluents.

In another aspect of the invention, there is provided a method of inhibiting activity of BACE with a compound according to formula (I).

In another aspect of the invention, there is provided a method of treating or preventing an Aβ-related pathology in a mammal, such as a human being, comprising administering to said patient a therapeutically effective amount of a compound according to formula (I), and at least one cognitive enhancing agent, memory enhancing agent, or choline esterase inhibitor, wherein said Aβ-related pathology is Alzheimer's disease.

The treatment of Aβ-related pathology defined herein may be applied as a mono therapy or may involve, in addition to the compound of the invention, conjoint treatment with conventional therapy of value in treating one or more disease conditions referred to herein. Such conventional therapy may include one or more of the following categories of agents: acetyl cholinesterase inhibitors, anti-inflammatory agents, cognitive and/or memory enhancing agents or atypical antipsychotic agents. Cognitive enhancing agents, memory enhancing agents and acetyl choline esterase inhibitors includes, but not limited to, donepezil (ARICEPT), galantamine (REMINYL or RAZADYNE), rivastigmine (EXELON), tacrine (COGNEX) and memantine (NAMENDA, AXURA or EBIXA). Atypical antipsychotic agents includes, but is not limited to, olanzapine (marketed as ZYPREXA), aripiprazole (marketed as ABILIFY), risperidone (marketed as RISPERDAL), quetiapine (marketed as SEROQUEL), clozapine (marketed as CLOZARIL), ziprasidone (marketed as GEODON) and olanzapine/fluoxetine (marketed as SYMBYAX).

Such conjoint treatment may be achieved by way of the simultaneous, sequential or separate dosing of the individual components of the treatment. Such combination products employ the compounds of the invention.

Additional conventional chemotherapy may include one or more of the following categories of agents: (i) antidepressants, (ii) atypical antipsychotics, (iii) antipsychotics, (iv) anxiolytics, (v) anticonvulsants, (vi) currently used Alzheimer's therapies, (vii) Parkinson's therapies, (viii) migraine therapies, (ix) stroke therapies, (x) urinary incontinence therapies, (xi) neuropathic pain therapies, (xii) nociceptive pain therapies, (xiii) insomnia therapies and (xiv) mood stabilizers. Known treatments for the foregoing therapies may be employed in combination with the invention described herein.

Such combination products employ the compounds of this invention within the dosage range described herein and the other pharmaceutically active compound or compounds within approved dosage ranges and/or the dosage described in the publication reference.

Methods of Preparation

The present invention also relates to processes for preparing the compound of formula (I) as a free base or a pharmaceutically acceptable salt thereof. Throughout the following description of such processes it is understood that, where appropriate, suitable protecting groups will be added to, and subsequently removed from the various reactants and intermediates in a manner that will be readily understood by one skilled in the art of organic synthesis. Conventional procedures for using such protecting groups as well as examples of suitable protecting groups are for example described in *Protective Groups in Organic Synthesis* by T. W. Greene, P. G. M Wutz, 3$^{rd}$ Edition, Wiley-Interscience, New York, 1999. It is understood that microwaves (MW) can alternatively be used for the heating of reaction mixtures. Another aspect of the present invention provides a process for preparing a compound of formula (I), or a pharmaceutically acceptable salt thereof, wherein, unless specified otherwise, $R^1$-$R^9$, n and A are defined as for formula (I) above, or are groups that can be converted into $R^1$-$R^9$, or A in subsequent transformations. LG represents a leaving group such as halogen (such as chlorine, bromine or iodine) or an alkyl-, aryl- or haloalkyl-sulfonate (such as triflate) and PG represents a protecting group. Said process comprises of the following methods.

Preparation Methods

Method (i): Formation of a Corresponding Compound of Formula (IIIa):

Scheme 1

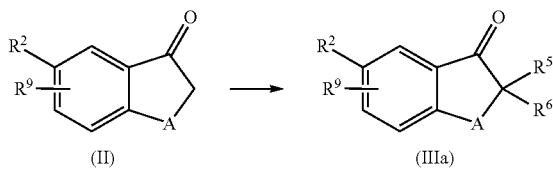

A ketone of formula (II), is treated with a suitable bas such as sodium hydride, KOtBu, or LDA in presence of an alkyl acrylate or a (bis-substituted)alkyl halide, triflate or mesylate to give a compound of formula (IIIa) (Scheme 1). Said reaction may be performed at a temperature range between −78° C. and +50° C., in a suitable solvent, such as tetrahydrofuran or dimethylformamide. Alkyations may be carried out in a sequential way with intermediates isolated and purified or in a one-pot stepwise fashion. If the reactions yield a product substituted with an olefin, cyano, keto, ester, sulfone or the like it could optionally be reacted further by Dieckman cyclization, reduction, RCM, nucleophilic substitution or cycloaddition to give highly substituted spirocyclic intermediates.

Method (ii): Formation of a Corresponding Compound of Formula (IIIa):

Scheme 2

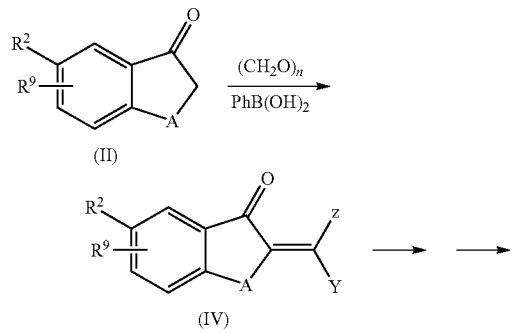

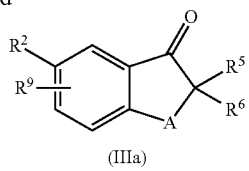

A ketone of formula (II), is reacted with an aldehyde or ketone such as formaldehyde in a temperature range between room temperature and +100° C. in presence of any protic acid such as a boronic acid in a suitable solvent such as benzene or toluene (Scheme 2). The intermediate (IV), wherein Z and Y are defined as for example hydrogen or alkyl, can be reacted with various dienes utilizing the Diels-Alder reaction in a temperature range between room temperature and +220° C. optionally in a sealed tube. The reaction can be carried out neat or in a suitable solvent such as benzene, toluene or THF. A Lewis acid or any other agent that may assist the reaction can be added to yield enriched enantiomers or diastereomers. The resulting spirocyclic ring may optionally contain one or more substituent which may be further converted by known functional group transformations.

Method (iii): Formation of a Corresponding Compound of Formula (IIIa):

Scheme 3

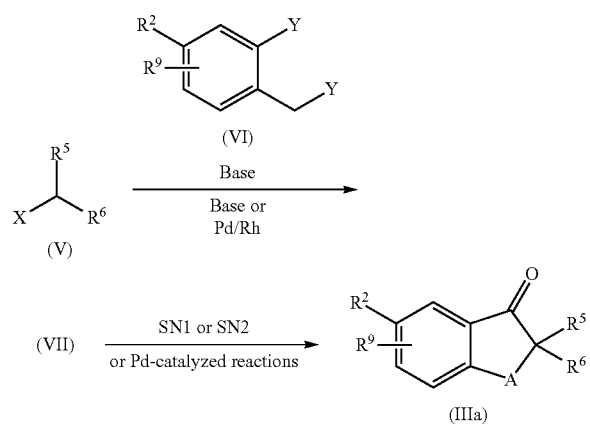

An alkyl or cycloalkyl or heterocycloalkyl derivative (V) containing electron withdrawing groups X such as cyano, carboxylic acid or alkylesters can be alkylated with optionally substituted ortho-halo benzyl halide (VI) (Y=halogen such as bromo or chloro) (Scheme 3). Said reaction is assisted by a base such as LDA, NaH or LiHMDS in a solvent such as benzene, THF or toluene at temperature range between −78° C. and 80° C. An alkylated intermediate (VII) can be isolated and further subjected to a base such as BuLi or LDA in solvents such as THF to effect ring cyclizations. Alternatively one can also utilize transition metal chemistry such as Pd, Cu or Rh containing chelating agents such as phosphine derivatives or amines in solvents such as DMF, THF or toluene in presence of a base such as triethylamine or sodium carbonate at temperature range between room temperature and +100° C. In the event where the product (VII) from the reaction contains a substituent such as olefin, sulfone, cyano, and the like, they can be further manipulated (Scheme 3) by nucleophilic substitution, PD-catalyzed reactions or any other known reaction to give highly substituted spirocyclic compounds (IIIa).

Method (iv) Formation of a Corresponding Compound of Formula (XVIII):

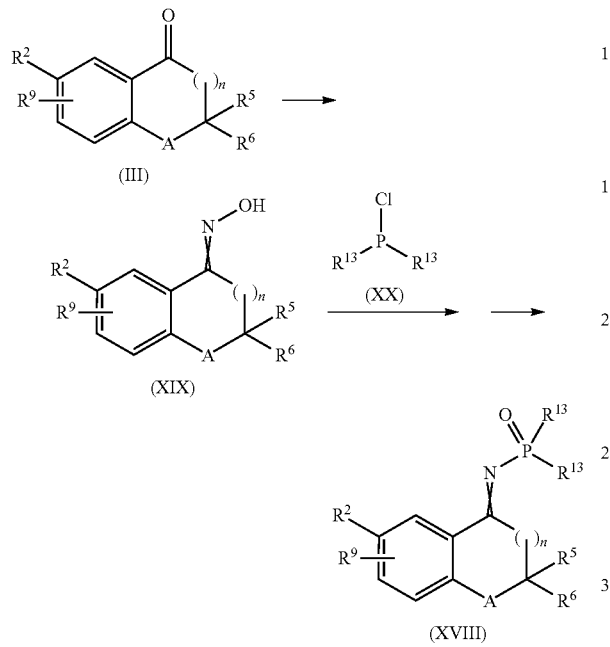

A compound of formula (XIX) may be obtained by reacting a compound of formula (III) with hydroxylamine hydrochloride and a base such as potassium acetate in a suitable solvent such as a mixture of water and a suitable alcohol such as ethanol at reflux temperature (Scheme 4a). Said compound (XIX) may be further transformed into a compound of formula (XVIII) by reacting it with a compound of formula (XX), wherein $R^{13}$ is alkyl or aryl. The reaction is performed in a suitable solvent such as dichloromethane in the presence of triethylamine at a temperature between −78° C. and room temperature.

Method (v) Formation of a Corresponding Compound of Formula (XXI):

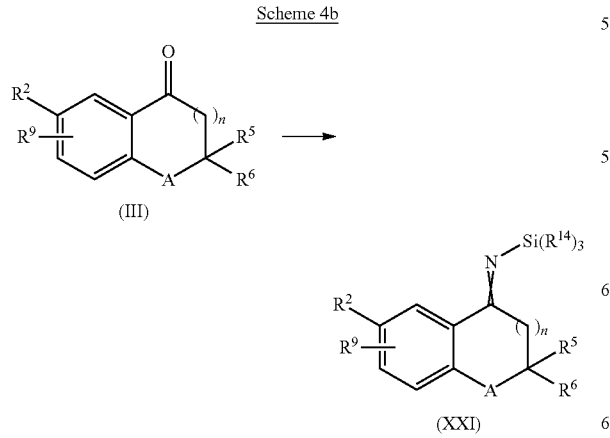

A compound of formula (XXI) wherein $R^{14}$ is an alkyl such as methyl may be obtained by reacting a compound of formula (III) with a silicon compound such as LiHMDS in a suitable solvent such as dichloromethane, 2-methyl-tetrahydrofuran or tetrahydrofuran (Scheme 4b).

Method (vi) Formation of a Corresponding Compound of Formula (M1):

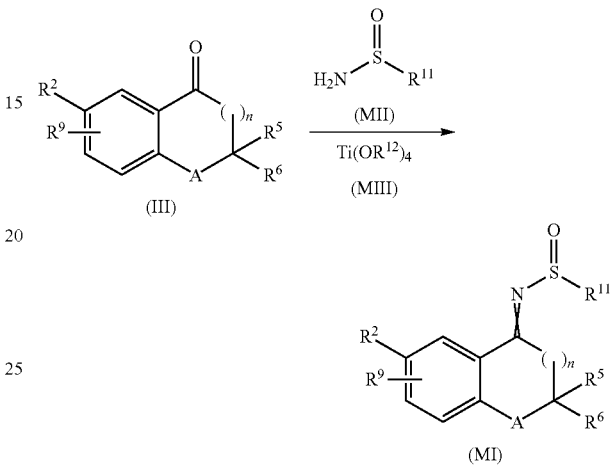

A compound of formula (M1) may be obtained by reacting a compound of formula (III) with a compound of formula (MII) (Scheme 4c), wherein $R^{11}$ is alkyl (such as for example tert-butyl). The reaction is performed in the presence of a suitable Lewis acid, such as a compound of formula (MIII), wherein $R^{12}$ is alkyl (such as ethyl or isopropyl). The reaction is performed in a suitable solvent (such as dichloromethane, 2-methyl-tetrahydrofuran or tetrahydrofuran) at a temperature between room temperature and 130° C. using microwave heating or conventional heating in an oil bath.

Method (vii) Formation of a Corresponding Compound of Formula (MIV):

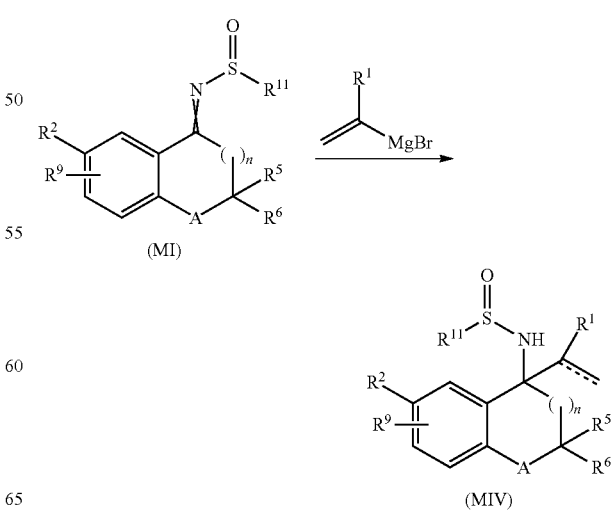

A compound of formula (MI), is reacted with vinylmagnesium bromides to form a compound of formula (MIV). Said reaction may be performed at a temperature range between 0° C. and room temperature, in a suitable solvent, such as e.g. dichloromethane, 2-methyl-tetrahydrofuran or tetrahydrofuran (Scheme 5).

Method (viii): Formation of a Corresponding Compound of Formula (MV):

Scheme 6

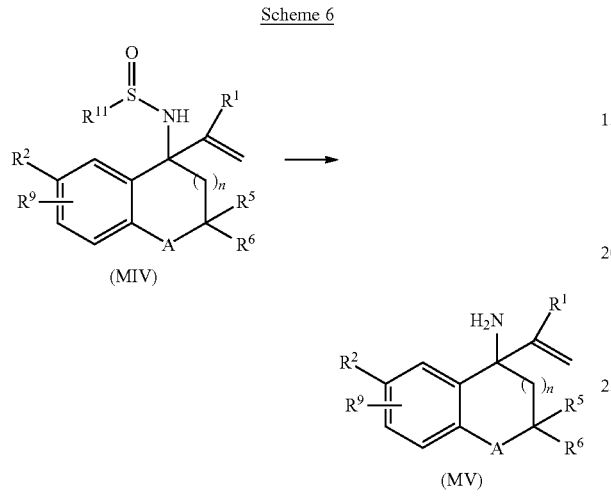

A compound of formula (MV) may be obtained by reacting a compound of formula (MIV) (Scheme 6) with a mineral acid, such as hydrogen chloride in a suitable solvent, such as isopropanol or dioxane. Said reaction may be performed at a temperature range between 0° C. and room temperature, in a suitable solvent, such as dioxane or methanol.

Method (ix) Formation of a Corresponding Compound of Formula (MVI):

Scheme 7

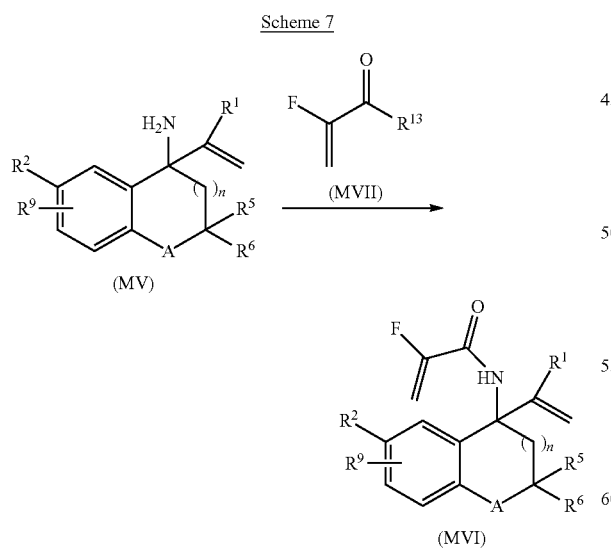

A compound of formula (MVI) can be obtained by reacting an amine of formula (MV) with a compound of formula (MVII) (Scheme 7), wherein $R^{13}$ is hydroxyl or chloride. If $R^{13}$ is hydroxyl, an amide coupling reagent can be used, such as HBTU, HATU or T3P. Said reaction may be performed at a temperature range between 0° C. and room temperature, in a suitable solvent, such as tetrahydrofuran or dichloromethane in the presence of a suitable amine base, such as triethyl amine or diisopropyl ethylamine.

Method (x) Formation of a Corresponding Compound of Formula (MVIII):

Scheme 8

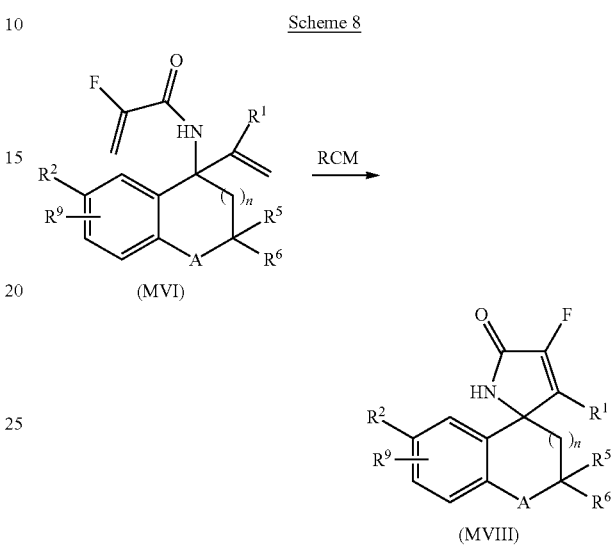

A compound of formula (MVIII) may be obtained by reacting a compound of formula (MVI) (Scheme 8) in the presence of a catalyst, such as Grubbs Catalyst $2^{nd}$ Generation or Hoveyeda-Grubbs Catalyst $2^{nd}$ Generation in a suitable solvent, such as dichloromethane or toluene. Said reaction may be performed at a temperature between 60° C. and 180° C. using microwave heating or conventional heating in an oil bath.

Method (xi) Formation of a Corresponding Compound of Formula (MIX):

Scheme 9

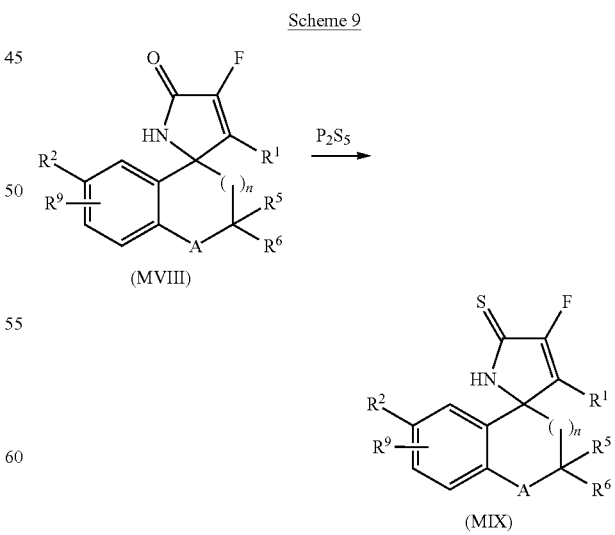

A compound of formula (MIX) may be obtained by reacting a compound of formula (MVIII) with phosphorus pentasulfide. Said reaction may be performed at a temperature between room temperature and 150° C. using microwave heating or conventional heating in an oil bath in a suitable solvent such as pyridine or 1,2-dichloroethane.

Method (xii) Formation of a Corresponding Compound of Formula (I):

Scheme 10

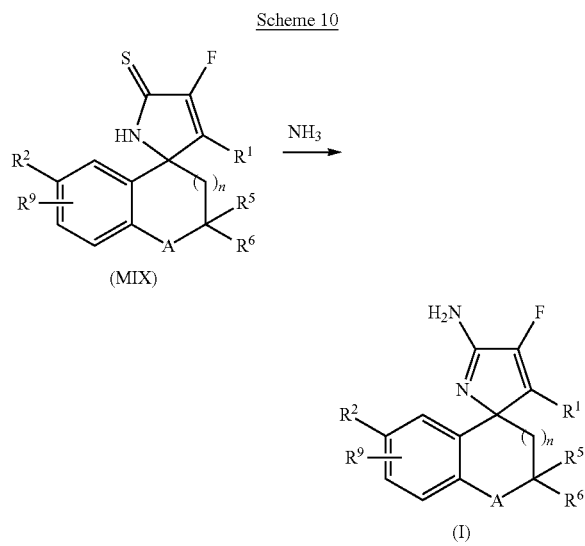

A compound of formula (I) can be obtained by treating a compound of formula (MIX) with ammonia, in a suitable solvent such as methanol, tetrahydrofuran, or 2-methyl-tetrahydrofuran optionally in the presence of an oxidation agent, such as tert-butyl hydroperoxide, at a temperature between room temperature and 150° C., optionally in a closed system (Scheme 10).

Method (xiii) Formation of a Corresponding Compound of Formula (I):

Scheme 11

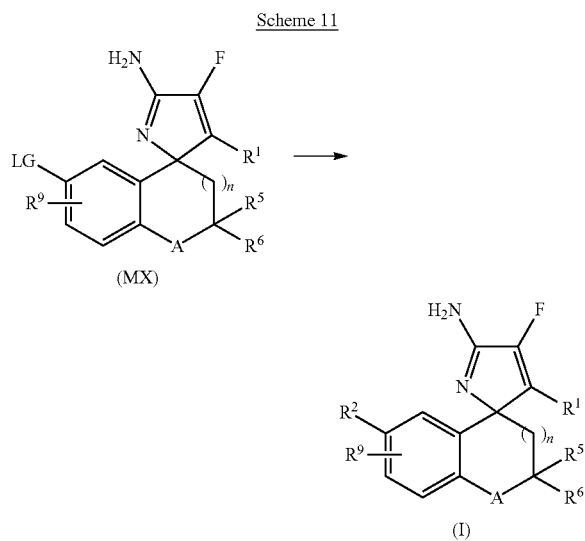

A compound of formula (I) wherein $R^2$ is an optionally substituted aryl or heteroaryl, may be obtained (Scheme 11) by starting from, for example, a compound of formula (MX), and reacting said compound of formula (MX) with a boronic acid or a boronic ester or a stannane of formula T-$R^2$, wherein T is for example $B(OH)_2$, $B(Oalkyl)_2$, or $Sn(alkyl)_3$, and $R^2$ is an optionally substituted aryl or a heteroaryl, in the presence of a transition metal catalyst such as a palladium catalyst, such as bistriphenylphosphine)palladium(II) chloride, tetrakis(triphenylphosphine)-palladium(0), palladium diphenylphosphinoferrocene dichloride, palladium(II) acetate or bis(dibenzylideneacetone) palladium (0). Optionally, a suitable ligand such as triphenylphosphine, tri-tert-butylphosphine or 2-(dicyclohexylphosphino)biphenyl, or zinc and sodium triphenylphosphinetrimetasulfonate, is used. A suitable base, such as cesium fluoride, an alkyl amine, such as triethyl amine, or an alkali metal carbonate or hydroxide such as potassium carbonate, sodium carbonate, cesium carbonate, or sodium hydroxide, may be used in the reaction. Said reaction may be performed in a suitable solvent, such as toluene, tetrahydrofuran, 2-methyl-tetrahydrofuran, dioxane, dimethoxyethane, water, ethanol, N,N-dimethylacetamide, acetonitrile or N,N-dimethylformamide, or mixtures thereof.

Alternatively a compound of formula (I) wherein $R^2$ is an optionally substituted aryl or heteroaryl can be prepared from compound (MX) by transformation into a compound (Ia) wherein T is as described above ($B(OH)_2$ or $B(Oalkyl)_2$) (Scheme 11a). Compound (Ia) is then reacted with a compound $R^2$-LG wherein $R^2$ is an optionally substituted aryl or heteroaryl and LG is a leaving group such as a halogen to yield compound (I).

Scheme 11a

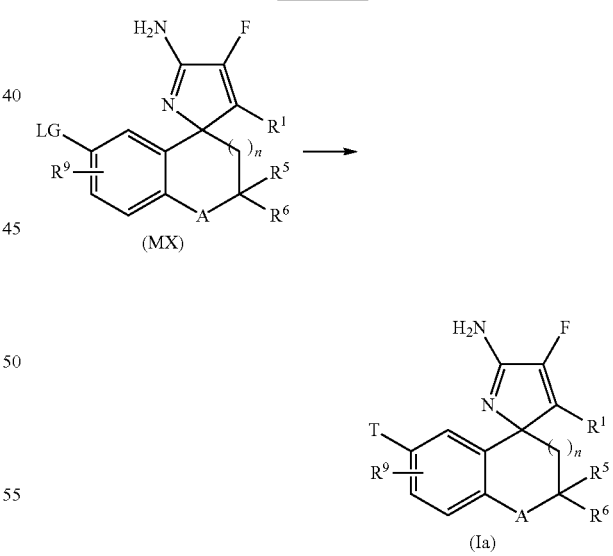

Method (xiv) Formation of a Corresponding Compound of Formula (I):

A compound of formula (I), wherein $R^2$ is cyano, may be obtained (Scheme 11) by starting from, for example, a compound of formula (MX), wherein LG is a leaving group such as a halogen, (such as iodide, bromide or chlorine), and reacting said compound of formula (MX) with a metal cyano reagent such as copper(I) cyanide.

Method (xv) Formation of a Corresponding Compound of Formula (MVIII):

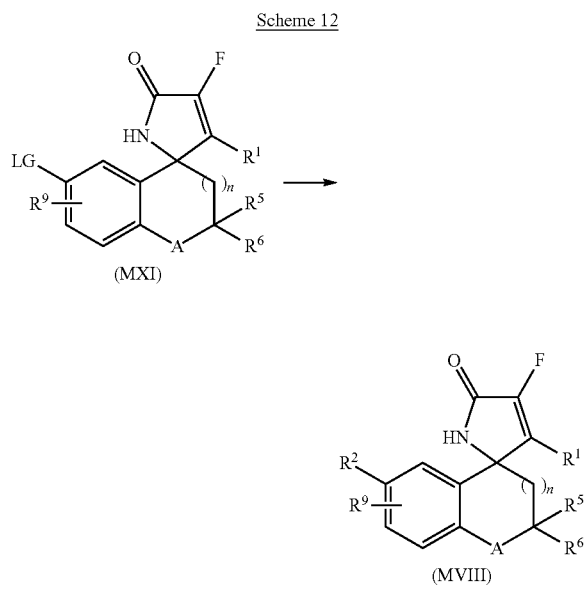

A compound of formula (MVIII) wherein R² is an optionally substituted aryl or heteroaryl, may be obtained (Scheme 12) by starting from, for example, a compound of formula (MXI), and reacting said compound of formula (MXI) with a boronic acid or a boronic ester or a stannane of formula T-R², wherein T is for example B(OH)₂, B(Oalkyl)₂, or Sn(alkyl)₃ and R² is an optionally substituted aryl or a heteroaryl, in the presence of a transition metal catalyst such as a palladium catalyst, such as bis(triphenylphosphine)palladium(II) chloride, tetrakis(triphenylphosphine)-palladium(0), palladium diphenylphosphinoferrocene dichloride, palladium(II) acetate or bis(dibenzylideneacetone) palladium (0). Optionally, a suitable ligand such as triphenylphosphine, tri-tert-butylphosphine or 2-(dicyclohexylphosphino)biphenyl, or zinc and sodium triphenylphosphinetrimetasulfonate, is used. A suitable base, such as cesium fluoride, an alkyl amine, such as triethyl amine, or an alkali metal carbonate or hydroxide such as potassium carbonate, sodium carbonate, cesium carbonate, or sodium hydroxide, may be used in the reaction. Said reaction may be performed in a suitable solvent, such as toluene, tetrahydrofuran, 2-methyl-tetrahydrofuran, dioxane, dimethoxyethane, water, ethanol, N,N-dimethylacetamide, acetonitrile or N,N-dimethylformamide, or mixtures thereof.

Alternatively a compound of formula (MVIII) wherein R² is an optionally substituted aryl or heteroaryl can be prepared from compound (MXI) by transformation into a compound (MVIIIa) wherein T is as described above (B(OH)₂ or B(Oalkyl)₂) (Scheme 12a). Compound (MVIIIa) is then reacted with a compound R²-LG wherein R² is an optionally substituted aryl or heteroaryl and LG is a leaving group such as a halogen to yield compound (MVIII).

Method (xvi) Formation of a Corresponding Compound of Formula (I):

A compound of formula (I), wherein R² is an alkyl group such as methyl may be generated from a compound of formula (MX) (Scheme 11), wherein LG represents a leaving group, such as a halogen, (such as iodide, bromide or chlorine), by reaction with an organometallic reagent generated from zinc iodide and methylmagnesium bromide under the influence of a transition metal catalyst such as for example bis(triphenylphosphine)palladium(II) chloride.

Method (xvii) Formation of a Corresponding Compound of Formula (I):

A compound of formula (I), wherein R² is an alkyne may be generated from a compound of formula (MX) (Scheme 11), wherein LG represents a leaving group, such as a halogen, (such as iodide or bromide), by reaction with an alkyne such as such as an alkylethyne or a cycloalkylethyne under the influence of a transition metal catalyst such as for example tetrakis(triphenylphosphine)palladium(0) in presence of a base such as triethylamine and copper(I)iodide. The alkyne is optionally silylated. Said reaction may be performed at a temperature range between room temperature and reflux temperature, in a suitable solvent, such as THF or toluene.

Method (xviii) Formation of a Corresponding Compound of Formula (IIIb):

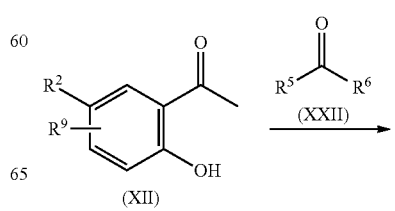

-continued

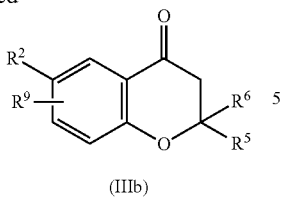

(IIIb)

A compound of formula (IIIb) may be obtained by reacting a ketone of formula (XII) with an aldehyde or ketone of formula (XXII) in presence of a base such as pyrrolidine, piperidine, proline, morpholine or Borax in a suitable solvent such as benzene, toluene, methanol or ethanol or a mixture of water and a suitable alcohol such as methanol or ethanol in a temperature range between room temperature and +180° C. (Scheme 13).

Method (xix) Formation of a Compound of Formula (I)

Scheme 14

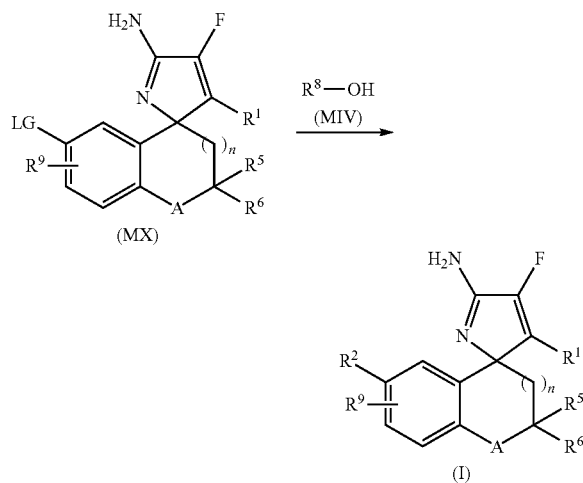

A compound of formula (I) wherein $R^2$ is $OR^8$ may be prepared by reacting a compound of formula (MX), wherein LG represents a leaving group, such as a halogen, (such as iodide or bromide), with an alcohol of formula (MIV) in the presence of a suitable palladium catalyst such as palladium (II)acetate, optionally in the presence of a suitable ligand such as 2-(di-t-butylphosphino)-1,1'-binaphthyl (Scheme 14). Said reaction is performed in the presence of a suitable base such as cesium carbonate in a suitable solvent such as THF, 2-methyl-tetrahydrofuran or toluene at a temperature between 20° C. and 160° C.

Method (xx): Formation of a Corresponding Compound of Formula (IIIc):

Scheme 15

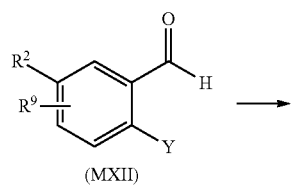

(MXII)

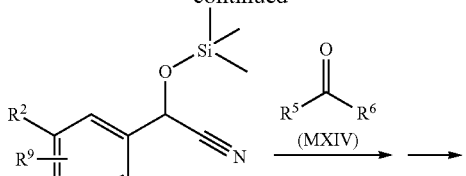

(MXIII)

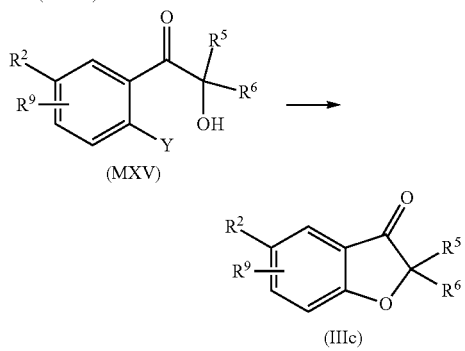

An aldehyde of formula (MXII), wherein Y is halogen such as fluorine, may be treated with trimethyl silyl cyanide in the presence of a base, such as DMAP to form an intermediate of formula (MXIII). Said reaction may be performed at a temperature between 0° C. and 100° C., in a suitable solvent, such as acetonitrile. The intermediate (MXIII) may be treated with a suitable base, such as LiHMDS, and further reacted with a ketone of formula (MXIV) to form a compound of formula (MXV) after acidic work up. Said reaction may be performed at a temperature between −78° C. and RT, in a suitable solvent, such as THF. Said compound of formula (MXV) may be subjected to a suitable base, such as potassium tert-butoxide to form a ketone of formula (IIIc). Alternatively, this reaction may be performed in the presence of a metal catalyst, such as a palladium or copper catalyst. Said reaction may be performed at a temperature between room temperature and 100° C., in a suitable solvent, such as THF. If the reactions yield a product substituted with an olefin, cyano, keto, ester, sulfone or the like it could optionally be reacted further by Dieckman cyclization, reduction, hydrolysis, RCM, nucleophilic substitution or cycloaddition to give highly substituted spirocyclic intermediates.

Compounds of formula (II), (III), (V), (VI), (XX), (MII), (MIII), (MVII), (MXII), and (MXIV) may be commercially available compounds, or may be known in the literature, or may be prepared by standard processes known in the art.

General Methods:

All solvents used were of analytical grade and commercially available anhydrous solvents were routinely used for reactions. Starting materials used were available from commercial sources, or prepared according to literature procedures. Room temperature refers to 20-25° C. Solvent mixture compositions are given as volume percentages or volume ratios.

Microwave heating was performed in a Biotage Creator, Initiator or Smith Synthesizer Single-mode microwave cavity producing continuous irradiation at 2450 MHz. It is understood that microwaves can be used for the heating of reaction mixtures.

Thin layer chromatography (TLC) was performed on Merck TLC-plates (Silica gel 60 $F_{254}$) and spots were UV visualized. Straight phase flash column chromatography was manually performed on Merck Silica gel 60 (0.040-0.063 mm), or automatically using an ISCO Combiflash® Companion™ system using RediSep™ normal-phase flash columns using the solvent system indicated. Phase separation was optionally performed on an Isolute® phase separator.
NMR NMR spectra were recorded on a 400-600 MHz NMR spectrometer fitted with a probe of suitable configuration. Spectra were recorded at ambient temperature unless otherwise stated. Chemical shifts are given in ppm down- and upfield from TMS (0.00 ppm). The following reference signals were used in $^1$H-NMR: TMS δ 0.00, or the residual solvent signal of DMSO-$d_6$ δ 2.49, $CD_3OD$ δ 3.30, acetone-$d_6$ 2.04 or $CDCl_3$ δ 7.25 (unless otherwise indicated). Resonance multiplicities are denoted s, d, t, q, m, br and app for singlet, doublet, triplet, quartet, multiplet, broad and apparent, respectively. In some cases only diagnostic signals are reported.

HPLC, HPLCMS, and LCMS Analyses:

High pressure liquid chromatography (HPLC) was performed on a reversed phase (RP) column A linear gradient was applied using for example mobile phase A (10 mM $NH_4OAc$ in 5% $CH_3OH$ or 5% $CH_3CN$ (aq.), or 0.1% $NH_3$ (aq.) or 0.1% formic acid (aq.)) and B ($CH_3OH$ or $CH_3CN$). Mass spectrometry (MS) analyses were performed in positive and/or negative ion mode using electrospray ionization (ESI+/−) and/or atmospheric pressure chemical ionization (APCI+/−).

GCFID and GCMS Analyses:

Gas chromatography (GC) was performed on a GC equipped with a mass spectrometer (MS) or a flame ionization detector (FID). The MS ion source was either an electron impact (EI) or a chemical ionization (CI, reactant gas methane). For separation a capillary column was used for example DB-5MS, (J&W Scientific). A linear temperature gradient was applied.

Preparative chromatography was carried out with a Waters FractionLynx system with a Autosampler combined Automated Fraction Collector (Waters 2767), Gradient Pump (Waters 2525), Column Switch (Waters CFO) and PDA (Waters 2996). Column; XBridge® Prep C8-10 μm OBD™ 19×300 mm, with guard column; XTerra® Prep MS C8 10 μm 19×10 mm Cartridge. A gradient of A (95% 0.1 M $NH_4OAc$ in MilliQ water and 5% MeCN) in B (100% MeCN) or a gradient of A (95% 0.1 M $NH_4OAc$ in MilliQ water and 5% MeOH), A (0.2% $NH_3$ in MilliQ water) or A (0.2% formic acid in MilliQ water) in B (100% MeOH) was applied for LC-separation at flow rate 20 ml/min.

SFC Analyses:

Supercritical Fluid Chromatography (SFC) was performed on a straight phase column. A isocratic flow was applied using mobile phase A ($CO_2$) and for example mobile phase B (MeOH, EtOH or IPA).

Straight Phase HPLC Analyses:

High pressure liquid chromatography (HPLC) was performed on a straight phase column. A linear gradient or isocratic flow was applied using for example mobile phase A (Heptane) and B (EtOH or IPA).

Preparative chiral chromatography for separation of enantiomers was run on for example a LaPrep® system using the specified column and mobile phase system.

TERMS AND ABBREVIATIONS

ACN acetonitrile
aq aqueous;
Atm atmospheric pressure;
Boc t-butoxycarbonyl;
Borax di-sodium tetraborate or sodium borate or sodium tetraborate;
Cbz benzyloxycarbonyl;
CDI 1,1'-carbonyldiimidazole;
dba dibenzylideneacetone
DCM dichloromethane;
DEA diethylamine;
DIBAL-H diisobutylaluminium hydride
DIPEA diisopropylethylamine;
DME 1,2-dimethoxyethane
DMF N,N-dimethyl formamide;
DMSO dimethyl sulfoxide;
$Et_2O$ diethyl ether;
EtOAc ethyl acetate;
EtOH ethanol;
eq. or equiv. equivalent
h hour(s);
HATU 2-(7-aza-1H-benzotriazole-1-yl)-1,1,3,3-tetramethyluronium hexafluorophosphate
HBTU O-benzotriazole-N,N,N',N'-tetramethyluronium hexafluorophosphate
HPLC high performance liquid chromatography;
LCMS liquid chromatography mass spectrometry
LDA lithium diisopropylamide
LiHMDS lithium bis(trimethylsilyl)amide
MeOH methanol;
min minute(s);
MS mass spectrometry
MW microwave(s)
$NH_4OAc$ ammonium acetate;
NMR nuclear magnetic resonance;
ox oxidation;
Psi pounds per square inch;
quant. quantitative;
RCM ring closing metathesis;
r.t. room temperature;
sat. saturated;
SFC supercritical fluid chromatography;
T3P propylphosphonic anhydride
TFA trifluoroacetic acid;
THF tetrahydrofuran;
TLC thin layer chromatography
TMEDA tetramethylethylenediamine
UPLC ultra performance liquid chromatography Compounds have been named using CambridgeSoft MedChem ELN v2.2 or ACD/Name, version 10.0, or 10.06, or version 12.01, software from Advanced Chemistry Development, Inc. (ACD/Labs), Toronto ON, Canada, www.acd-labs.com, or Lexichem, version 1.9, software from OpenEye.

EXAMPLES

Below follows a number of non-limiting examples of compounds of the invention.

General Method for Suzuki Coupling

The bromide (1 eq), the boronic acid (1.2 eq) and bis(triphenylphosphine)-palladium(II)chloride (0.1 eq) were taken up in DME (1 mL) and water (0.5 mL). Sodium carbonate (1M) (2.5 eq) was added and the reaction was heated to 80° C. for 2 h.

Intermediate 1: 6'-Bromo-4-methoxyspiro[cyclohexane-1,2'-inden]-1'(3'H)-one

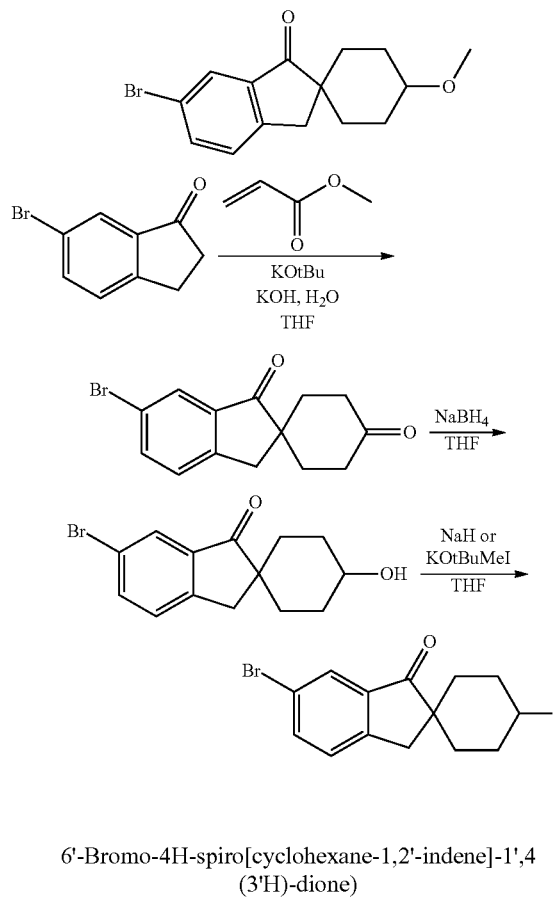

6'-Bromo-4H-spiro[cyclohexane-1,2'-indene]-1',4(3'H)-dione)

Potassium tert-butoxide (7.50 g, 66.81 mmol) was added in portions to 6-bromo-2,3-dihydro-1H-inden-1-one (11.75 g, 55.67 mmol) and methyl acrylate (11.05 mL, 122.5 mmol) in THF (55 mL) cooled in an ice-bath. The mixture was stirred for 1.5 h at r.t. Water (80 mL) and potassium hydroxide (3.12 g, 55.7 mmol) was added and the mixture was heated to 75° C. and then at 60° C. overnight. The mixture was cooled to 0° C., and the formed precipitate was filtered off and dried in vacuo to give the title compound (11.69 g, 72% yield). $^1$H NMR (500 MHz, CDCl$_3$) δ ppm 1.83-1.92 (m, 2H), 2.15-2.27 (m, 2H), 2.40-2.50 (m, 2H), 2.71 (dt, 2H), 3.17 (s, 2H), 7.39 (d, 1H), 7.75 (dd, 1H), 7.92 (d, 1H); MS (ES+) m/z 293, 295 [M+H]$^+$.

6'-Bromo-4-hydroxyspiro[cyclohexane-1,2'-inden]-1'(3'H)-one

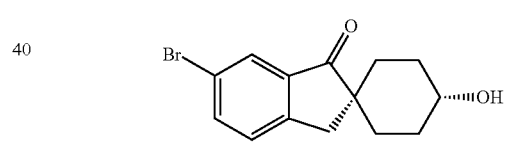

6'-Bromo-4H-spiro[cyclohexane-1,2'-indene]-1',4(3'H)-dione (6.1 g, 20.8 mmol) was dissolved in THF (220 mL) and cooled to −65° C. Sodium borohydride (0.354 g, 9.36 mmol) was added and the cooling bath was removed. The mixture was allowed to reach 0° C. (approx. 30 min). Water (10 mL) was added, and most of the organic solvent was removed by evaporation. The residue was partitioned between EtOAc (100 mL), and brine (50 mL). The organic phase was dried (MgSO$_4$) and evaporated to give a product which was combined with additional product obtained in a similar way starting from 14.6 g of 6'-bromo-4H-spiro [cyclohexane-1,2'-indene]-1',4(3'H)-dione. Purification was done by column chromatography (120 g silica, eluent: CH$_2$Cl$_2$ to CH$_2$Cl$_2$/MeOH, 90:10 gradient) affording 13.6 g (66% yield) of the title compound. The obtained material consisted of a 80:20 mixture of isomer 1 and isomer 2. Analytical samples of the isomers were isolated by column chromatography using EtOAc 0% to 100% in heptane to yield:

Isomer 1: (1r,4r)-6'-Bromo-4-hydroxyspiro[cyclohexane-1,2'-inden]-1'(3'H)-one

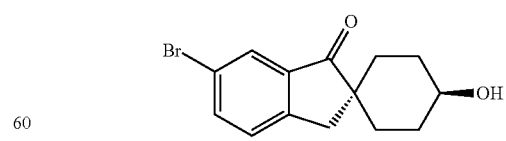

$^1$H NMR (400 MHz, DMSO-d$_6$) δ ppm 1.20-1.43 (m, 4H), 1.49-1.62 (m, 2H), 1.79-1.89 (m, 2H), 2.99 (s, 2H), 3.39-3.50 (m, 1H), 4.68 (d, 1H), 7.56 (d, 1H), 7.76 (d, 1H), 7.85 (dd, 1H); MS (ES+) m/z 317, 319 [M+Na]$^+$ Isomer 2: (1s,4s)-6'-bromo-4-hydroxyspiro[cyclohexane-1,2'-inden]-1'(3'H)-one $^1$H NMR (400 MHz, DMSO-d$_6$) δ ppm 1.07-1.20 (m, 2H), 1.51-1.63 (m, 2H), 1.65-1.76 (m, 2H), 1.93 (td, 2H), 2.98 (s, 2H), 3.83 (d, 1H), 4.45 (d, 1H), 7.51-7.55 (m, 1H), 7.76 (d, 1H), 7.84 (dd, 1H); MS (ES+) m/z 317, 319 [M+Na]$^+$.

6'-Bromo-4-methoxyspiro[cyclohexane-1,2'-inden]-1'(3'H)-one

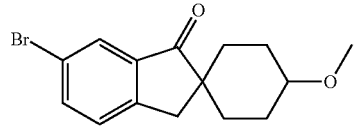 [SMILES: COC1CCC2(CC1)Cc1ccc(Br)cc1C2=O]

A mixture of isomers of 6'-bromo-4-hydroxyspiro[cyclohexane-1,2'-inden]-1'(371)-one (12.7 g, 43.0 mmol) was dissolved in THF (210 mL) under N₂ and cooled to 0° C. Potassium tert-butoxide (5.79 g, 51.6 mmol) was added portionwise and the mixture was stirred at 0° C. for 25 min. Methyl iodide (4.30 mL, 68.8 mmol) was added. The cooling bath was removed, and the mixture was stirred at r.t. Additional potassium tert-butoxide (0.483 g, 4.30 mmol) was added twice, after 2 h and 3 h respectively, and then the mixture was stirred for 2 h. Water (100 mL) was added and the resulting solution was partitioned between brine (200 mL) and EtOAc (200 mL). The aqueous phase was extracted with another portion of EtOAc (100 mL). The combined organic phases were dried (MgSO₄) and evaporated to give 12.5 g (94% yield) of a mixture (approx. 80:20) of two isomers.

Isomer 1: (1r,4r)-6'-bromo-4-methoxyspiro[cyclohexane-1,2'-inden]-1'(3'H)-one

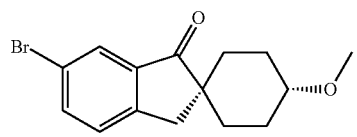 [SMILES: CO[C@H]1CC[C@]2(CC1)Cc1ccc(Br)cc1C2=O]

and Isomer 2: (1s,4s)-6'-bromo-4-methoxyspiro[cyclohexane-1,2'-inden]-1'(3'H)-one

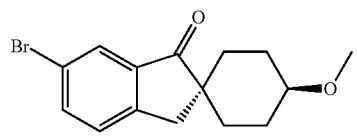 [SMILES: CO[C@H]1CC[C@@]2(CC1)Cc1ccc(Br)cc1C2=O]

¹H NMR (400 MHz, DMSO-d₆) δ ppm 1.20-1.32 (m, 2H), 1.40-1.48 (m, 2H), 1.51-1.62 (m, 2H), 1.97-2.07 (m, 2H), 3.00 (s, 2H), 3.15-3.23 (m, 1H), 3.26 (s, 3H), 7.56 (d, 1H), 7.77 (d, 1H), 7.86 (dd, 1H); MS (ES+) m/z 309, 311 [M+H]⁺.

Intermediate 1 may also be prepared by a process described in WO2010105179.

Example 1: (1r,4r)-4''-fluoro-4-methoxy-6'-(pyrimidin-5-yl)-3'H-dispiro[cyclohexane-1,2'-indene-1,2''-pyrrol]-5''amine

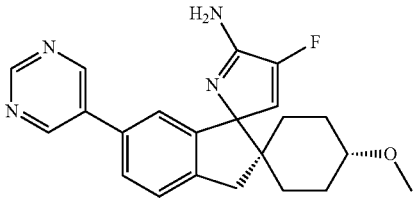

Step 1: N-(6'-Bromo-4-methoxyspiro[cyclohexane-1,2'-inden]-1'(3'H)-ylidene)-2-methylpropane-2-sulfinamide 6'-Bromo-4-methoxyspiro[cyclohexane-1,2'-inden]-1'(3'H)-one (Intermediate 1, mixture of isomers) (1.14 g, 3.69 mmol), 2-methylpropane-2-sulfinamide (0.670 g, 5.53 mmol) and titanium ethoxide (1.519 mL, 7.37 mmol) were dissolved in 2-methyltetrahydrofuran (8 mL) and heated to reflux for 26 h. The reaction was allowed to cool to room temperature. EtOAc (80 mL) and NaHCO₃ (sat, 15 mL) was added under stirring. The mixture was then left standing without stirring for 15 min. The mixture was filtered and the phases separated. The aqueous phase was extracted with EtOAc. The combined organic phases were, dried over MgSO₄ and concentrated. Column chromatography (silica gel) with a gradient of 0-20% EtOAc in n-heptane gave the title compound (1.00 g, 66% yield). MS (ES+) m/z 412, 414 [M+H]⁺.

Step 2: N-(6'-Bromo-1'-ethenyl-4-methoxy 1',3'-dihydrospiro[cyclohexane-1,2'-inden]-1'-yl)-2-methylpropane-2-sulfinamide N-(6'-bromo-4-methoxyspiro[cyclohexane-1,2'-inden]-1'(3'H)-ylidene)-2-methylpropane-2-sulfinamide (mixture of isomers) (2.55 g, 6.18 mmol) was dissolved in THF (50 mL) under a nitrogen atmosphere. The reaction was cooled to 0° C. Vinylmagnesium bromide (1M in THF) (13.60 mL, 13.60 mmol) was added. The reaction was stirred for 1 h. The reaction was quenched with a saturated NH₄Cl solution. The phases were separated and the aqueous phase extracted with THF. The combined organic phases were washed with brine, dried over MgSO₄, filtered and the solvent evaporated to yield 2.7 g (99%) of the title compound. MS (ES+) m/z 440, 442 [M+H]⁺.

Step 3: 6'-Bromo-1'-ethenyl-4-methoxy-1',3'-dihydrospiro[cyclohexane-1,2'-inden]-1'-amine N-(6'-bromo-1'-ethenyl-4-methoxy-1',3'-dihydrospiro[cyclohexane-1,2'-inden]-1'-yl)-2-methylpropane-2-sulfinamide (mixture of isomers) (2.7 g, 6.13 mmol) was dissolved in 1,4-dioxane (20 mL) and cooled to 0° C. HCl (5M in isopropanol) (12.26 mL, 61.30 mmol) was added and the reaction was stirred at r.t. for 30 min. The reaction mixture was poured into water and basified with 2M KOH. The mixture was extracted with dichloromethane. The combined organic phases were dried over MgSO₄, filtered and the solvents evaporated to yield 2.7 g (131%) of the title compound. MS (ES+) m/z 319, 321 [M–NH3]+.

Step 4: N-(6'-Bromo-1'-ethenyl-4-methoxy-1',3'-dihydrospiro[cyclohexane-1,2'-inden]-1'-yl)-2-fluoroprop-2-enamide 2-Fluoroacrylic acid (1.45 g, 16.06 mmol) and HBTU (7.31 g, 19.27 mmol) were dissolved in dichloromethane (30 mL). Triethylamine (3.36 mL, 24.09 mmol) was added and the reaction was stirred for 6 min. 6'-Bromo-1'-ethenyl-4-methoxy-1,3'-dihydrospiro[cyclohexane-1,2'-inden]-1'-amine (mixture of isomers) (2.7 g, 8.03 mmol) was added as a solution in dichloromethane (20 mL). The reaction was stirred for 16 h. The reaction mixture was poured in water. The phases were separated and the aqueous phase extracted with dichloromethane. The combined organic phases were dried over MgSO4, filtered and the solvent evaporated. Column chromatography (silica gel) using dichloromethane yielded 1.4 g (43%) of the title compound. MS (ES–) m/z 406, 408 [M–H]−.

Step 5: 6'-Bromo-4''-fluoro-4-methoxy-3'H-dispiro[cyclohexane-1,2'-indene-1',2''-pyrrol]-5''(1''H)-one N-(6'-Bromo-1'-ethenyl-4-methoxy-1',3'-dihydrospiro[cyclohexane-1,2'-inden]-1'-yl)-2-fluoroprop-2-enamide (mixture of isomers) (1.4 g, 3.43 mmol) and Grubbs Catalyst 2nd Generation (0.292 g, 0.34 mmol) were taken up in dichloromethane (20 mL). The reaction was put under nitrogen atmosphere and heated to 120° C. for 40 min by microwave heating. Another addition of the same amount of catalyst was made and the reaction was heated to 120° C. for 40 min by microwave heating. Hoveyda-Grubbs Catalyst 2nd Generation (0.216 g, 0.34 mmol) was added and the reaction was heated to 120° C. for 40 min. Another addition of the same amount of catalyst was made and the reaction was heated to 120° C. for 40 min by microwave heating. Column chromatography using EtOAc 0% to 100% in heptane yielded 277 mg (21%) of the title compound. MS (ES–) m/z 378, 380 [M–H]−.

Step 6: 6'-Bromo-4''-fluoro-4-methoxy-3'H-dispiro[cyclohexane-1,2'-indene-1',2''-pyrrol]-5''-amine 6'-Bromo-4''-fluoro-4-methoxy-3'H-dispiro[cyclohexane-1,2'-indene-1',2''-pyrrol]-5''(1''H)-one (mixture of isomers) (277 mg, 0.73 mmol) was dissolved in pyridine (2.5 mL). Phosphorus pentasulfide (277 mg, 0.62 mmol) was added and the reaction was stirred at 120° C. for 1 h. The reaction was cooled to r.t. Ammonia (7M in MeOH) (4.16 mL, 29.14 mmol) and tert-butyl hydroperoxide (70% in water) (1.501 mL, 10.93 mmol) were added and the reaction was stirred at r.t. for 16 h. The reaction mixture was extracted with dichloromethane. The combined organic phases were dried over MgSO4, filtered and the solvents evaporated. Column chromatography using MeOH with 7M NH3 0% to 5% in DCM yielded 120 mg (43%) of the title compound. MS (ES+) m/z 379, 381 [M+H]+.

Step 7: (1r,4r)-4''-fluoro-4-methoxy-6'-(pyrimidin-5-yl)-3'H-dispiro[cyclohexane-1,2'-indene-1,2''-pyrrol]-5''amine 6'-Bromo-4''-fluoro-4-methoxy-3'H-dispiro[cyclohexane-1,2'-indene-1',2''-pyrrol]-5''-amine (mixture of isomers) (60 mg, 0.16 mmol) was reacted with pyrimidin-5-ylboronic acid (23.52 mg, 0.19 mmol) using the general method for Suzuki coupling. The reaction mixture was filtered and the two isomers were isolated by RP-HPLC. 15.8 mg (26%) of the equatorial product. 1H NMR (500 MHz, CDCl3) δ ppm 1.27-1.42 (m, 3H), 1.50 (td, 1H), 1.61-1.75 (m, 2H), 1.93-2.03 (m, 2H), 2.98 (d, 1H), 3.05-3.14 (m, 1H), 3.20 (d, 1H), 3.35 (s, 3H), 4.92 (br. s., 2H), 6.44 (d, 1H), 7.08 (s, 1H), 7.35-7.45 (m, 2H), 8.87 (s, 2H), 9.15 (s, 1H); MS (ES+) m/z 379 [M+H]+.

Example 2: (1s,4s)-4''-Fluoro-4-methoxy-6'-(pyrimidin-5-yl)-3'H-dispiro[cyclohexane-1,2'-indene-1,2''-pyrrol]-5''amine

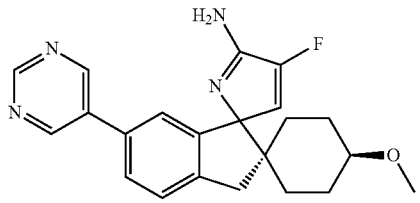

6'-Bromo-4''-fluoro-4-methoxy-3'H-dispiro[cyclohexane-1,2'-indene-1',2''-pyrrol]-5''-amine (mixture of isomers) (60 mg, 0.16 mmol) was reacted with pyrimidin-5-ylboronic acid (23.52 mg, 0.19 mmol) using the general method for Suzuki coupling. The reaction mixture was filtered and the two isomers were isolated by RP-HPLC. 6.3 mg (11%) of the axial product. 1H NMR (500 MHz, CDCl3) δ ppm 1.30-1.77 (m, 6H), 1.76-1.97 (m, 2H), 2.98-3.22 (m, 2H), 3.30 (s, 3H), 3.44 (br. s., 1H), 6.49 (d, 1H), 7.10 (s, 1H), 7.40 (d, 2H), 8.88 (s, 2H), 9.16 (s, 1H); MS (ES+) m/z 379 [M+H]+.

Example 3: (1r,4r)-4''-Fluoro-4-methoxy-6'-[5-(prop-1-yn-1-yl)pyridin-3-yl]-3'H-dispiro[cyclohexane-1,2'-indene-1',2''-pyrrol]-5''amine

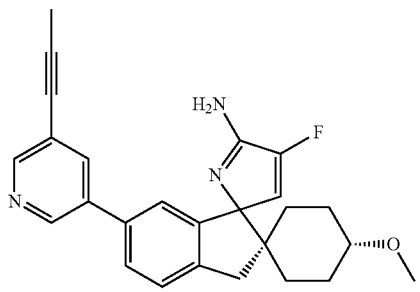

6'-Bromo-4''-fluoro-4-methoxy-3'H-dispiro[cyclohexane-1,2'-indene-1',2''-pyrrol]-5''-amine (mixture of isomers) (60 mg, 0.16 mmol) was reacted with 5-(prop-1-ynyl)pyridin-3-ylboronic acid (30.6 mg, 0.19 mmol) (For preparation see WO2011002408, WO2011002407, or WO2006138264.) using the general method for Suzuki coupling. The reaction mixture was filtered and the two isomers isolated by RP-HPLC. 14.4 mg (22%) of the equatorial product. 1H NMR (500 MHz, CDCl3) δ ppm 1.26-1.42 (m, 3H), 1.48 (td, 1H), 1.59-1.78 (m, 2H), 1.92-2.02 (m, 2H), 2.09 (s, 3H), 2.97 (d, 1H), 3.05-3.13 (m, 1H), 3.18 (d, 1H), 3.35 (s, 3H), 5.00 (br.

s., 2H), 6.43 (d, 1H), 7.07 (s, 1H), 7.33-7.42 (m, 2H), 7.79 (s, 1H), 8.54 (s, 1H), 8.63 (d, 1H); MS (ES+) m/z 416 [M+H]+.

Example 4: (1s,4s)-4''-Fluoro-4-methoxy-6'-[5-(prop-1-yn-1-yl)pyridin-3-yl]-3'H-dispiro[cyclohexane-1,2'-indene-1',2''-pyrrol]-5''amine

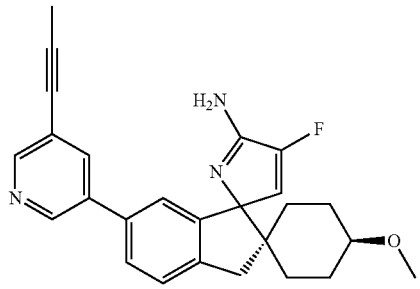

6'-Bromo-4''-fluoro-4-methoxy-3'H-dispiro[cyclohexane-1,2'-indene-1',2''-pyrrol]-5''-amine (mixture of isomers) (60 mg, 0.16 mmol) was reacted with 5-(prop-1-ynyl)pyridin-3-ylboronic acid (30.6 mg, 0.19 mmol) (For preparation see WO2011002408, WO2011002407, or WO2006138264.) using the general method for Suzuki coupling. The reaction mixture was filtered and the two isomers isolated by RP-HPLC. 7.5 mg (11%) of the axial product. ¹H NMR (500 MHz, CDCl₃) δ ppm 1.31-1.94 (m, 8H), 2.09 (s, 3H), 2.99-3.19 (m, 2H), 3.29 (s, 3H), 3.43 (br. s., 1H), 4.78 (br. s., 2H), 6.48 (br. s., 1H), 7.08 (s, 1H), 7.33-7.42 (m, 2H), 7.79 (s, 1H), 8.54 (s, 1H), 8.63 (d, 1H); MS (ES+) m/z 416 [M+H]+.

Intermediate 2: 5-Bromo-4'-methoxy-3H-spiro[1-benzofuran-2,1'-cyclohexan]-3-one

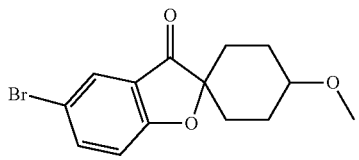 [SMILES: COC1CCC2(CC1)Oc1ccc(Br)cc1C2=O]

may be prepared by the following method:

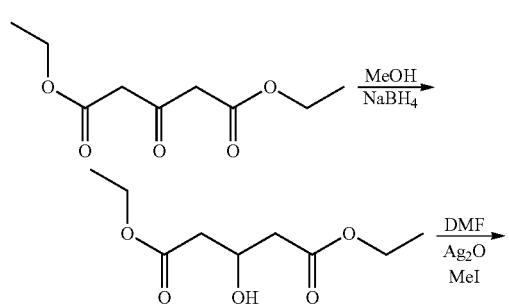

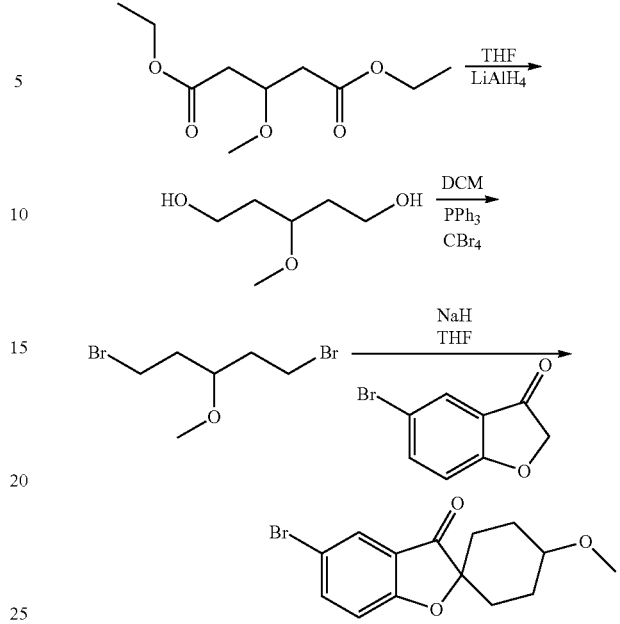

or alternatively via the following method:

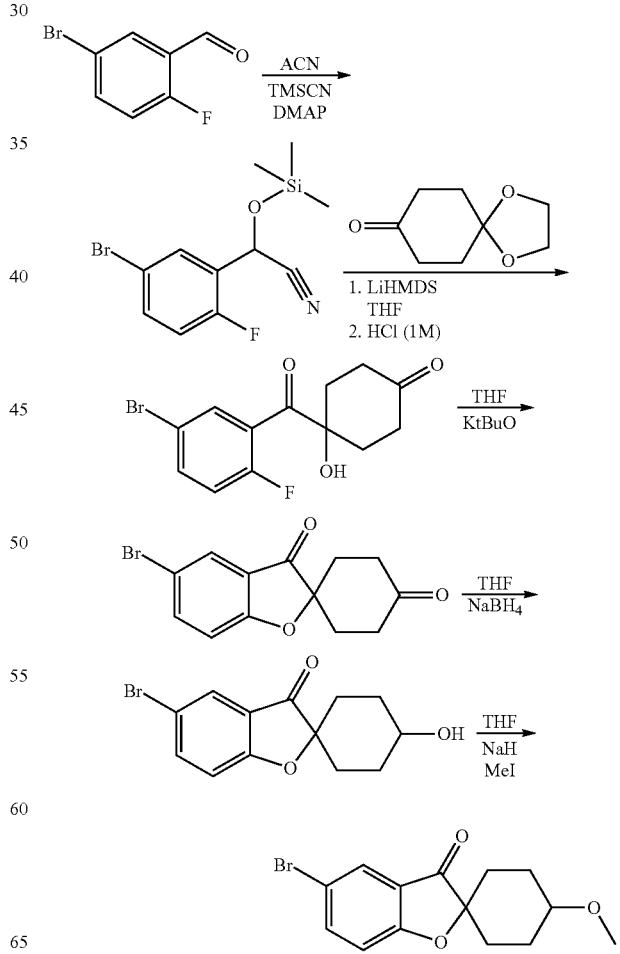

or alternatively via the following method:

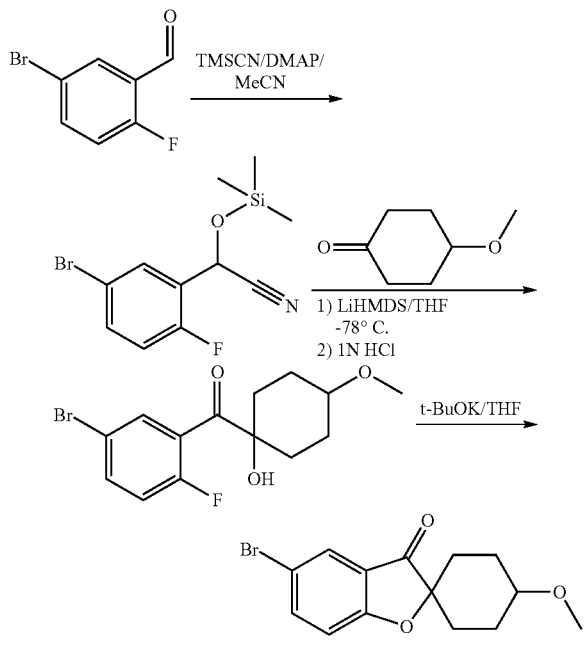

(5-Bromo-2-fluorophenyl)[(trimethylsilyl)oxy]acetonitrile

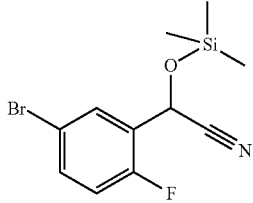 [SMILES: C[Si](C)(C)OC(C#N)c1cc(Br)ccc1F]

To a solution of 5-bromo-2-fluoro-benzaldehyde (30.45 g, 150 mmol) in tetrahydrofuran (250 mL), was added DMAP (0.203 g, 1.73 mmol) followed by trimethylsilyl cyanide (18.24 g, 183.8 mmol). The reaction mixture was stirred at r.t. for 4 h and then concentrated in vacuo to afford 45.8 g (quantitative yield) of the title compound which was used directly in the next step without further purification. $^1$H NMR (400 MHz, CDCl$_3$) δ ppm 1.71 (m, 6H), 2.31 (m, 2H), 3.32 (m, 1H), 3.41 (s, 3H), 7.03 (d, 1H), 7.36 (t, 1H), 7.77 (d, 1H).

(5-Bromo-2-fluorophenyl)(1-hydroxy-4-methoxycyclohexyl)methanone

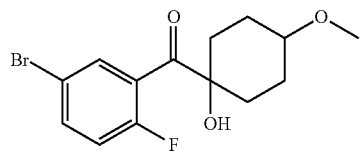 [SMILES: COC1CCC(O)(C(=O)c2cc(Br)ccc2F)CC1]

LiHMDS (1.0 M, 165 mL, 165 mmol) was added dropwise to a solution of (5-Bromo-2-fluorophenyl)[(trimethylsilyl)oxy]acetonitrile (45.80 g, 150 mmol) in acetonitrile (250 mL) at −78° C. The reaction mixture was stirred for 1.5 h and a solution of 4-methoxycyclohexanone (Lee, C. K.; Lee, I.-S. H.; Noland, W. E. Heterocycles, 2007, 71, 419-428) (20.3 g, 150 mmol) in tetrahydrofuran (30 mL) was added slowly and the stirring at −78° C. was continued for 3 h. 1M HCl aq. (300 mL) was added at −78° C., and the mixture was allowed to warm slowly to r.t. and stirred overnight. The phases were separated and the aqueous layer was extracted with ethyl acetate (2×500 mL). The combined extracts were dried over sodium sulfate, filtered, and concentrated in vacuo to afford 57 g of material. A portion of the product (30 g) was purified by flash column chromatography using a gradient of 0 to 50% ethyl acetate in hexanes to afford 9.24 g of the title compound.

5-Bromo-4'-methoxy-3H-spiro[benzofuran-2,1'-cyclohexan]-3-one

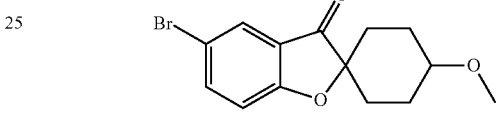

A mixture of (5-bromo-2-fluorophenyl)(1-hydroxy-4-methoxycyclohexyl)-methanone (1.05 g, 3.17 mmol) and potassium tert-butoxide (0.445 g, 3.80 mmol) in tetrahydrofuran (10 mL) was heated in a microwave reactor at 70° C. for 30 min. The solvent was removed in vacuo and the residue was purified by flash column chromatography using a gradient of 0 to 15% ethyl acetate in hexanes to afford 388 mg (39% yield) of the title compound. $^1$H NMR (400 MHz, CDCl$_3$): δ ppm 1.71 (m, 6H), 2.31 (m, 2H), 3.32 (m, 1H), 3.41 (s, 3H), 7.03 (d, 1H), 7.36 (t, 1H), 7.77 (d, 1H); MS (ES+) m/z: 312 [M+H]$^+$.

Example 5: 3-[(1s,4s)-5"-Amino-4"-fluoro-4-methoxydispiro[cyclohexane-1,2'-[1]benzofuran-3', 2"-pyrrol]-5'-yl]-5-fluorobenzonitrile

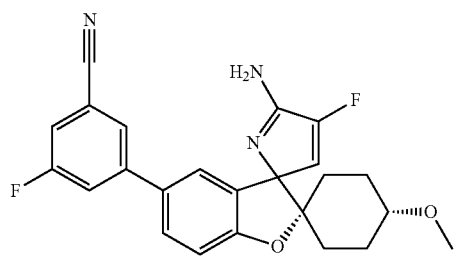

Step 1: N-((1's,4's)-5-Bromo-4'-methoxy-3H-spiro[benzofuran-2,1'-cyclohexane]-3-ylidene)-2-methylpropane-2-sulfinamide (1's,4's)-5-Bromo-4'-methoxy-3H-spiro[benzofuran-2,1'-cyclohexan]-3-one (Intermediate 3) (5.91 g, 18.99 mmol) and 2-methylpropane-2-sulfinamide (4.60 g, 37.99 mmol) were dissolved in methyl THF (50 mL). Titanium(IV) ethoxide (30 mL, 47.35 mmol) was added and the reaction was heated to reflux for 16 h. The reaction mixture was poured into 100 ml of EtOAc. 30 ml of water was added and stirred vigorously. The formed slurry was allowed to settle and was filtered by suction filtration. The filtrate was dried over MgSO$_4$, filtered and the solvents evaporated. The product was crystallized from Et$_2$O and heptane yielding 6.5 g (83%) of the title compound. $^1$H NMR (500 MHz, CDCl$_3$) δ ppm 1.32 (s, 9H) 1.63-1.95 (m, 6H) 2.07-2.17 (m, 2H) 3.33 (t, 1H) 3.41 (s, 3H) 6.93 (d, 1H) 7.59 (dd, 1H) 8.52 (br. s., 1H); MS (ES+) m/z 414, 416 [M+H]$^+$.

Step 2: N-((1's,4's)-5-Bromo-4'-methoxy-3-vinyl-3H-spiro[benzofuran-2,1'-cyclohexane]-3-yl)-2-methylpropane-2-sulfinamide N-((1's,4's)-5-Bromo-4'-methoxy-3H-spiro[benzofuran-2,1'-cyclohexane]-3-ylidene)-2-methylpropane-2-sulfinamide (6.5 g, 15.69 mmol) was dissolved in THF (100 mL) and put under nitrogen atmosphere. The reaction was cooled to 0° C. vinylmagnesium bromide (38 mL, 38 mmol) was added. The reaction was stirred for 1 h at r.t. The reaction was quenched with sat NH$_4$Cl solution. The phases were separated and the aqueous phase extracted with THF. The combined organic phases were dried over MgSO$_4$, filtered and the solvent evaporated to yield 6.48 g (93%). MS (ES+) m/z 442, 444 (M+H)+

Step 3: (1's,4's)-5-Bromo-4'-methoxy-3-vinyl-3H-spiro[benzofuran-2,1'-cyclohexan]-3-amine N-((1's,4's)-5-Bromo-4'-methoxy-3-vinyl-3H-spiro[benzofuran-2,1'-cyclohexane]-3-yl)-2-methylpropane-2-sulfinamide (6.48 g, 14.65 mmol) was dissolved in dioxane (50 mL) and cooled to 0° C. HCl (5M in isopropanol) (29.3 mL, 146.47 mmol) was added and the reaction was stirred at r.t. for 30 min. The reaction mixture was poured into a mixture of 100 ml 2M KOH and ice. The mixture was extracted with EtOAc. The combined organic phases were dried over MgSO$_4$, filtered and the solvents evaporated to yield 5.7 g (115%). MS (ES+) m/z 321, 323 (M–NH$_2$)+

Step 4: N-((1's,4's)-5-Bromo-4'-methoxy-3-vinyl-3H-spiro[benzofuran-2,1'-cyclohexane]-3-yl)-2-fluoroacrylamide 2-Fluoroacrylic acid (3.04 g, 33.70 mmol) and O-(1H-Benzotriazol-1-yl)-N,N,N',N'-tetramethyluronium hexafluorophosphate (25.6 g, 67.41 mmol) were dissolved in DCM (60 mL). Triethylamine (11.74 mL, 84.26 mmol) was added and the reaction was stirred for 6 min. (1's,4's)-5-Bromo-4'-methoxy-3-vinyl-3H-spiro[benzofuran-2,1'-cyclohexan]-3-amine (5.7 g, 16.85 mmol) was added as a solution in DCM (40 mL). The reaction was stirred for 16 h. The reaction mixture was poured in water. The phases were separated and the aqueous phase extracted with DCM. The combined organic phases were dried over MgSO$_4$, filtered and the solvent evaporated. The product was purified by column chromatography using MeOH 0% to 10% in DCM to yield 1 g (14.46%). $^1$H NMR (500 MHz, CDCl$_3$) δ ppm 1.53-1.60 (m, 1H) 1.60-1.72 (m, 2H) 1.89-2.10 (m, 5H) 3.23 (tt, 3.98 Hz, 1H) 3.37 (s, 3H) 4.81 (d, 1H) 5.18 (dd, 1H) 5.29 (d, 1H) 5.64-5.77 (m, 1H) 6.49-6.59 (m, 2H) 6.74 (d, 1H) 7.32 (d, 1H) 7.37 (dd, 1H). MS (ES–) m/z 408, 410 [M–H]$^-$ Step 5: (1s,4s)-5'-Bromo-4"-fluoro-4-methoxy-dispiro[cyclohexane-1,2'-[1]benzofuran-3',2"-pyrrol]-5"(1"H)-one N-((1's,4's)-5-Bromo-4'-methoxy-3-vinyl-3H-spiro[benzofuran-2,1'-cyclohexane]-3-yl)-2-fluoroacrylamide (1 g, 2.44 mmol) and Grubbs Catalyst 2nd Generation (0.207 g, 0.24 mmol) were taken up in DCM (20 mL) the reaction was put under nitrogen atmosphere and heated to 120° C. for 40 min by microwave heating. The reaction was repeated three times with Hoveyda-Grubbs Catalyst 2nd Generation (0.153 g, 0.24 mmol), once with 2,6-diisopropylphenylimido neophylidenemolybdenum (VI) bis(hexafluoro-t-butoxide) (0.1 g, 0.13 mmol), added under a blanket of argon and once with 2,6-diisopropylphenylimidoneophylidene[racemic-BI-PHEN]molybdenium(VI) (0.1 g, 0.13 mmol) also added under a blanket of argon. The product was purified by column chromatography using EtOAc 0% to 100% in heptane yielding 195 mg (21%) of the title compound. MS (ES+) m/z 382, 384 [M+H]$^+$ Step 6: (1s,4s)-5'-Bromo-4"-fluoro-4-methoxy-dispiro[cyclohexane-1,2'-[1]benzofuran-3',2"-pyrrol]-5"-amine (1s,4s)-5'-Bromo-4"-fluoro-4-methoxydispiro[cyclohexane-1,2'-[1]benzofuran-3',2"-pyrrol]-5"(1"H)-one (195 mg, 0.51 mmol) was taken up in pyridine (1.5 mL) and phosphorus pentasulfide (220 mg, 0.49 mmol) was added. The reaction was stirred at 120° C. for 1 h. The reaction was allowed to cool to r.t. Ammonia (7M in MeOH) (2.92 mL, 20.41 mmol) and tert-butyl hydroperoxide (70% in water) (1.051 mL, 7.65 mmol) were added. The reaction was stirred at r.t. for 16 h. The solvents were evaporated and the residue purified by column chromatography using MeOH with 7M NH$_3$ 0% to 5% to yield 31 mg (16%) of the title compound. $^1$H NMR (500 MHz, CDCl$_3$) δ ppm 1.34-1.49 (m, 2H) 1.60-1.75 (m, 2H) 1.89-2.05 (m, 3H) 2.13-2.24 (m, 1H) 3.15 (tt, 1H) 3.36 (s, 3H) 6.43 (d, 1H) 6.76 (d, 1H) 6.97 (d, 1H) 7.24-7.31 (m, 1H). MS (ES+) m/z 381, 383 [M+H]$^+$ Step 7: 3-[(1s,4s)-5"-Amino-4"-fluoro-4-methoxy-dispiro[cyclohexane-1,2'-[1]benzofuran-3',2"-pyrrol]-5'-yl]-5-fluorobenzonitrile (1s,4s)-5'-Bromo-4"-fluoro-4-methoxydispiro[cyclohexane-1,2'-[1]benzofuran-3',2"-pyrrol]-5"-amine (25 mg, 0.07 mmol) was reacted with 3-cyano-5-fluorophenylboronic acid (26.0 mg, 0.16 mmol) using the general method for Suzuki coupling and the product purified by RP-HPLC to yield 6.5 mg (3.5%). $^1$H NMR (500 MHz, CDCl$_3$) δ ppm 1.37-1.54 (m, 2H) 1.65-1.80 (m, 2H) 1.91-2.02 (m, 2H) 2.02-2.12 (m, 1H) 2.23 (m, 1H) 3.18 (tt, 1H) 3.37 (s, 3H) 4.94 (br. s., 2H) 6.49 (d, 1H) 6.98 (d, 1H) 7.03 (d, 1H) 7.24 (d, 1H) 7.39 (dd, 1H) 7.42 (m, 1H) 7.57 (s, 1H). MS (ES+) m/z 422 [M+H]$^+$

Example 6: 4'-Fluoro-3,3-dimethyl-6-(pyrimidin-5-yl)spiro[chroman-4,2'-pyrrol]-5'-amine

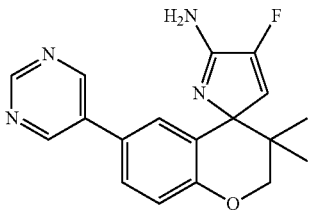 [SMILES: CC1(C)COc2ccc(-c3cncnc3)cc2C12C=C(F)C(N)=N2]

Step 1: 6-Bromo-3,3-dimethylchroman-4-one

6-Bromochroman-4-one (7.5 g, 33.03 mmol) was dissolved in THF (100 mL). Iodomethane (10.3 ml, 165.09 mmol) was added and the reaction was cooled to −78° C. Potassium tert-butoxide (18.5 g, 164.87 mmol) was added portion-wise and the reaction was slowly allowed to warm to r.t. The reaction was stirred for 16 h. Water was added and the mixture was extracted with diethyl ether. The combined organic phases were dried over MgSO$_4$, filtered and the solvents evaporated to yield 7.7 g (91%) of the title compound. $^1$H NMR (500 MHz, CDCl$_3$) δ ppm 1.21 (s, 6H) 4.15 (s, 2H) 6.88 (d, 1H) 7.54 (dd, 1H) 8.01 (d, 1H). MS (EI+) m/z 254, 256 [M]$^+$

Step 2: N-(6-Bromo-3,3-dimethylchroman-4-ylidene)-2-methylpropane-2-sulfinamide 6-Bromo-3,3-dimethylchroman-4-one (7.7 g, 30.18 mmol) and 2-methylpropane-2-sulfinamide (8.05 g, 66.40 mmol) were dissolved in methyl THF (50 mL). Titanium (IV) ethoxide (15.15 g, 66.40 mmol) was added and the reaction was fitted with a Dean-Stark condenser and heated to reflux for 2 days, during which 25 mL of solvent was removed from the Dean-Stark trap. The reaction mixture was poured into 100 ml of EtOAc. 30 mL of water was added and the mixture was stirred vigorously. The formed slurry was allowed to settle and was filtered by suction filtration. The filtrate was dried over MgSO$_4$, filtered and the solvents evaporated. Column chromatography using EtOAc 0% to 50% in heptane 0-50% yielded 4.4 g (41%) of the title compound. $^1$H NMR (500 MHz, DMSO-d$_6$) δ ppm 1.23 (s, 9H) 1.23-1.30 (m, 6H) 4.09 (s, 2H) 7.00 (d, 1H) 7.64 (dd, 1H) 8.08 (d, 1H). MS (ES+) m/z 358, 360 [M+H]$^+$.

Step 3: N-(6-Bromo-3,3-dimethyl-4-vinylchroman-4-yl)-2-methylpropane-2-sulfinamide N-(6-Bromo-3,3-dimethylchroman-4-ylidene)-2-methylpropane-2-sulfinamide (1.17 g, 3.27 mmol) was dissolved in THF (25 mL) and put under nitrogen atmosphere. The reaction was cooled to 0° C. Vinylmagnesium bromide (6.53 mL, 6.53 mmol) was added. The reaction was stirred for 1 h at r.t. The reaction was quenched with sat NH$_4$Cl solution. The phases were separated and the aqueous phase extracted with THF. The combined organic phases were dried over MgSO$_4$, filtered and the solvent evaporated to yield 1.1 g (87%) of the title compound. $^1$H NMR (500 MHz, DMSO-d$_6$) δ ppm 0.89 (s, 3H) 0.98 (s, 3H) 1.20 (s, 9H) 3.78-3.90 (m, 2H) 4.54 (d, 1H) 5.17 (s, 1H) 5.44 (d, 1H) 6.24 (dd, 1H) 6.74 (d, 1H) 7.32 (dd, 1H) 7.84 (d, 1H). MS (ES+) m/z 386, 388 [M+H]$^+$

Step 4: N-(6-Bromo-3,3-dimethyl-4-vinylchroman-4-yl)-2-methylpropane-2-sulfinamide N-(6-Bromo-3,3-dimethylchroman-4-ylidene)-2-methylpropane-2-sulfinamide (3.2 g, 8.93 mmol) was dissolved in THF (50 mL) and put under nitrogen atmosphere. The reaction was cooled to 0° C. Vinylmagnesium bromide (17.86 mL, 17.86 mmol) was added. The reaction was stirred for 1 h at r.t. The reaction was quenched with sat NH$_4$Cl solution. The phases were separated and the aqueous phase extracted with THF. The combined organic phases were dried over MgSO$_4$, filtered and the solvent evaporated to yield 3.2 g (93%) of the title compound $^1$H NMR (500 MHz, DMSO-d$_6$) δ ppm 0.89 (s, 3H) 0.98 (s, 3H) 1.20 (s, 9H) 3.78-3.90 (m, 2H) 4.54 (d, 1H) 5.17 (s, 1H) 5.44 (d, 1H) 6.24 (dd, 1H) 6.74 (d, 1H) 7.32 (dd, 1H) 7.84 (d, 1H). MS (ES+) m/z 386, 388 [M+H]$^+$

Step 5: 6-Bromo-3,3-dimethyl-4-vinylchroman-4-amine

N-(6-Bromo-3,3-dimethyl-4-vinylchroman-4-yl)-2-methylpropane-2-sulfinamide (4.3 g, 11.13 mmol) was dissolved in dioxane (50 mL) and cooled to 0° C. HCl (5M in isopropanol) (22.26 mL, 111.30 mmol) was added and the reaction was stirred at r.t. for 30 min. The reaction mixture was poured into a mixture of 100 ml 2M KOH and ice. The mixture was extracted with EtOAc. The combined organic phases were dried over MgSO$_4$, filtered and the solvents evaporated to yield 3.2 g (100%) of the title compound. $^1$H NMR (500 MHz, DMSO-d$_6$) δ ppm 0.85 (d, J=2.84 Hz, 6H) 1.93 (br. s., 2H) 3.79-4.02 (m, 2H) 5.08 (d, J=17.02 Hz, 1H) 5.23 (d, J=10.72 Hz, 1H) 6.01 (dd, J=17.18, 10.56 Hz, 1H) 6.71 (d, J=8.51 Hz, 1H) 7.24 (dd, J=8.67, 2.36 Hz, 1H) 7.40 (d, J=2.21 Hz, 1H). MS (ES+) m/z 265, 267 [M−NH$_2$]$^+$

Step 6: N-(6-Bromo-3,3-dimethyl-4-vinylchroman-4-yl)-2-fluoroacrylamide

2-Fluoroacrylic acid (2.042 g, 22.68 mmol) and O-(1H-benzotriazol-1-yl)-N,N,N',N'-tetramethyluronium hexafluorophosphate (10.32 g, 27.22 mmol) were taken up in DCM (30 mL) and TEA (4.74 mL, 34.02 mmol) was added. The reaction was stirred for 6 min. 6-bromo-3,3-dimethyl-4-vinylchroman-4-amine (3.2 g, 11.34 mmol) was added as a solution in DCM (20 mL) and the reaction was stirred for 16 h. The reaction mixture was poured into brine and the phases were separated. The aqueous phase was extracted with DCM. The combined organic phases were dried over MgSO$_4$, filtered and the solvent evaporated. The product was purified by column chromatography using EtOAc 0% to 100% in heptane to yield 1.5 g (37%) of the title compound. $^1$H NMR (500 MHz, DMSO-d$_6$) δ ppm 0.92 (s, 3H) 0.99 (s, 3H) 3.80-3.99 (m, 2H) 4.72 (d, 1H) 5.28 (dd, 1H) 5.36 (d, 1H) 5.43-5.59 (m, 1H) 6.45 (dd, 1H) 6.77 (d, 1H) 7.27 (s, 1H) 7.31 (d, 1H) 7.55 (br. s., 1H). MS (ES+) m/z 354, 356 [M+H]$^+$

Step 7: 6-Bromo-4'-fluoro-3,3-dimethylspiro[chroman-4,2'-pyrrol]-5'(1'H)-one N-(6-Bromo-3,3-dimethyl-4-vinylchroman-4-yl)-2-fluoroacrylamide (1.5 g, 4.23 mmol) was dissolved in DCM (20 mL) and Hoveyda-Grubbs Catalyst 2nd Generation (0.266 g, 0.42 mmol) was added and the reaction was heated to 120° C. for 40 min. The procedure was repeated twice with Hoveyda-Grubbs Catalyst 2nd Generation and three times with Grubbs Catalyst 2nd Generation (0.360 g, 0.42 mmol). The product was purified by column chromatography using EtOAc 0% to 100% in heptane to yield 465 mg (34%) of the title compound. $^1$H NMR (500 MHz, DMSO-$d_6$) δ ppm 0.87 (s, 3H) 0.91 (s, 3H) 3.96-4.12 (m, 2H) 6.84 (d, 1H) 6.97 (d, 1H) 7.10 (d, 1H) 7.38 (dd, 1H) 9.17 (br. s., 1H). MS (ES+) m/z 326, 328 [M+H]$^+$ Step 8: 6-Bromo-4'-fluoro-3,3-dimethylspiro[chroman-4,2'-pyrrol]-5'-amine 6-Bromo-4'-fluoro-3,3-dimethylspiro[chroman-4,2'-pyrrol]-5'(1'H)-one (465 mg, 1.43 mmol) and phosphorus pentasulfide (465 mg, 1.05 mmol) were taken up in pyridine (3 mL). The reaction was heated to 120° C. for 1 h. The reaction mixture was cooled to r.t. and ammonia (7M in MeOH) (8.15 mL, 57.03 mmol) and tert-butyl hydroperoxide (70% in water) (2.94 mL, 21.39 mmol) were added. The reaction was stirred at r.t. for 16 h. The solvents were evaporated and the residue purified by column chromatography using MeOH with 7M NH$_3$ 0% to 10% in DCM 0-10% to yield 120 mg (26%) mg of the title compound. $^1$H NMR (500 MHz, CDCl$_3$) δ ppm 0.89 (s, 3H) 1.01 (s, 3H) 3.84 (d, 1H) 4.23 (d, 1H) 6.43 (d, 1H) 6.74 (d, 1H) 6.97 (d, 1H) 7.22 (dd, 1H). MS (ES+) m/z 325, 327 [M+H]$^+$ Step 9: 4'-Fluoro-3,3-dimethyl-6-(pyrimidin-5-yl)spiro[chroman-4,2'-pyrrol]-5'-amine 6-Bromo-4'-fluoro-3,3-dimethylspiro[chroman-4,2'-pyrrol]-5'-amine (60 mg, 0.18 mmol) was reacted with pyrimidin-5-ylboronic acid (27.4 mg, 0.22 mmol) using the general method for Suzuki coupling. This procedure was repeated three times more. The reaction mixture was filtered and extracted with DCM. The solvents were evaporated and the products purified by RP-HPLC to yield 10.3 mg (17%) of the title compound. $^1$H NMR (500 MHz, CDCl$_3$) δ ppm 0.95 (s, 3H) 1.04 (s, 3H) 3.92 (d, 1H) 4.30 (d, 1H) 4.57 (br. s., 2H) 6.50 (d, 1H) 7.00 (d, 1H) 7.06 (d, 1H) 7.36 (dd, 2.36 Hz, 1H) 8.82 (s, 2H) 9.12 (s, 1H). MS (ES+) m/z 325 [M+H]$^+$ Example 7: 4'-Fluoro-6-(5-fluoropyridin-3-yl)-3,3-dimethylspiro[chroman-4,2'-pyrrol]-5'-amine

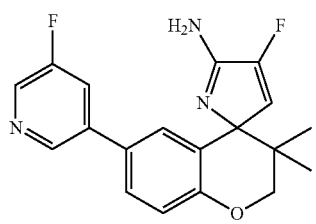 [SMILES: CC1(C)COc2ccc(-c3cncc(F)c3)cc2C12C=C(F)C(N)=N2]

6-Bromo-4'-fluoro-3,3-dimethylspiro[chroman-4,2'-pyrrol]-5'-amine (60 mg, 0.18 mmol) was reacted with 5-fluoropyridin-3-ylboronic acid (31.2 mg, 0.22 mmol) using the general method for Suzuki coupling. This procedure was repeated three times more. The reaction mixture was filtered and extracted with DCM. The solvents were evaporated and the product purified by RP-HPLC to yield 9.1 mg (14%) of the title compound. $^1$H NMR (500 MHz, CDCl$_3$) δ ppm 0.94 (s, 3H) 1.05 (s, 3H) 3.92 (d, 1H) 4.31 (d, 1H) 6.50 (d, 1H) 6.98 (d, 1H) 7.06 (d, 1H) 7.36 (dd, 1H) 7.46 (dt, 1H) 8.38 (d, 1H) 8.54 (t, 1H). MS (ES+) m/z 342 [M+H]$^+$.

Example 8: 6-(3,5-Difluorophenyl)-4'-fluoro-3,3-dimethylspiro[chroman-4,2'-pyrrol]-5'-amine

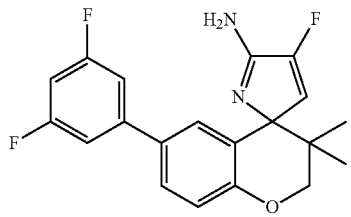 [SMILES: CC1(C)COc2ccc(-c3cc(F)cc(F)c3)cc2C12C=C(F)C(N)=N2]

Step 1: 6-(3,5-Difluorophenyl)-4'-fluoro-3,3-dimethylspiro[chroman-4,2'-pyrrol]-5'(1'H)-one 6-Bromo-4'-fluoro-3,3-dimethylspiro[chroman-4,2'-pyrrol]-5'(1'H)-one (124 mg, 0.38 mmol) was reacted with 3,5-difluorophenylboronic acid (72.0 mg, 0.46 mmol) using the general method for Suzuki coupling. The reaction mixture was extracted with DCM. The solvents were evaporated and the product purified by column chromatography using EtOAc 0% to 50% in heptane to yield 38.8 mg (28%) of the title compound. MS (ES+) m/z 358, 360 [M+H]$^+$ Step 2: 6-(3,5-Difluorophenyl)-4'-fluoro-3,3-dimethylspiro[chroman-4,2'-pyrrol]-5'-amine 6-(3,5-Difluorophenyl)-4'-fluoro-3,3-dimethylspiro[chroman-4,2'-pyrrol]-5'(1'H)-one (38.8 mg, 0.11 mmol) and phosphorus pentasulfide (40 mg, 0.09 mmol) were taken up in pyridine (1 mL). The reaction was heated to 120° C. for 1 h. The reaction mixture was cooled and ammonia (7M in MeOH) (0.617 mL, 4.32 mmol) and tert-butyl hydroperoxide (70% in water) (0.223 mL, 1.62 mmol) was added. The reaction was stirred at r.t. for 16 h. The product was purified by RP-HPLC to yield 12.1 mg (31%) of the title compound. $^1$H NMR (500 MHz, CDCl$_3$) δ ppm 0.93 (s, 3H) 1.05 (s, 3H) 3.90 (d, 1H) 4.30 (d, 1H) 6.49 (d, 1H) 6.71 (tt, 1H) 6.94 (d, 1H) 6.95-6.99 (m, 1H) 7.03 (d, 1H) 7.33 (dd, 1H). MS (ES+) m/z 359 [M+H]$^+$ Example 9: 4'-fluoro-2,2-dimethyl-6-(pyrimidin-5-yl)-2,3-dihydrospiro[indene-1,2'-pyrrol]-5'-amine

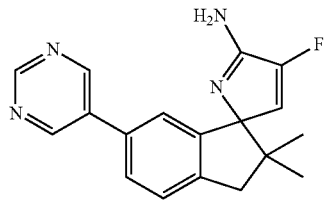 [SMILES: CC1(C)Cc2ccc(-c3cncnc3)cc2C12C=C(F)C(N)=N2]

Step 1: 6-bromo-2,2-dimethyl-2,3-dihydro-1H-inden-1-one

To a solution of 6-bromo-2,3-dihydro-1H-inden-1-one (5 g, 23.69 mmol) in dry THF (150 mL) was added iodomethane (3.70 mL, 59.23 mmol) and the mixture was stirred for 15 min. Sodium hydride (2.369 g, 59.23 mmol) was added in portions and stirring continued. After 2.5 h, water (100 mL) was added slowly and the mixture was extracted with EtOAc. The organic layer was dried over Na$_2$SO$_4$, filtered and concentrated. Purification by column chromatography using a gradient of 0-8% EtOAc in heptane as eluent afforded 4.74 g (84%) of the title compound. $^1$H NMR (500 MHz, CHLOROFORM-d) δ 1.24 (s, 6H), 2.95 (s, 2H), 7.32 (d, 1H), 7.70 (dd, 1H), 7.89 (d, 1H). MS (EI) m/z 238, 240 [M$^+$.].

Step 2: N-(6-bromo-2,2-dimethyl-2,3-dihydro-4H-inden-1-ylidene)-2-methylpropane-2-sulfinamide 6-bromo-2,2-dimethyl-2,3-dihydro-1H-inden-1-one (4.74 g, 19.82 mmol) and tert-Butyl sulfinamide (4.32 g, 35.68 mmol) were dissolved in 2-methyl tetrahydrofuran (50 mL) and Titanium(IV) ethoxide (8.29 mL, 39.65 mmol) was added. The resulting mixture was heated at reflux for 2.5 days. The mixture was allowed to cool to r.t. and EtOAc (100 mL) was added, followed by dropwise addition of water (15 mL) under vigorous stirring. After 10 min of stirring the mixture was allowed to stand still overnight. The formed solids were filtered off and the organic layer was concentrated. Purification of the product by column chromatography using a gradient of 0-15% EtOAc in heptane as eluent yielded 5.17 g (76%) of the title compound.
$^1$H NMR (500 MHz, CHLOROFORM-d) δ 1.27-1.41 (s, 15H), 2.93 (s., 2H), 7.23 (d, 1H), 7.60 (dd, 1H), 8.36-8.79 (br. s., 1H). MS (ES+) m/z 342, 344 [M+H]$^+$.

Step 3: N-(6-bromo-2,2-dimethyl-1-vinyl-2,3-dihydro-1H-inden-1-yl)-2-methylpropane-2-sulfinamide A solution of N-(6-bromo-2,2-dimethyl-2,3-dihydro-1H-inden-1-ylidene)-2-methylpropane-2-sulfinamide (2 g, 5.84 mmol) in dry 2-methyl tetrahydrofuran (40 mL) was cooled to −78° C. under nitrogen. Vinylmagnesium bromide (1.0 M in THF, 7.01 mL, 7.01 mmol) was added dropwise and the resulting mixture was left stirring at −78° C. After 2 h, more vinylmagnesium bromide (1.0 M in THF) (5.84 mL, 5.84 mmol) was added and stirring continued. After another hour at −78° C., the cooling bath was removed and the mixture was allowed to reach room temp. After a total of 4 h the reaction was quenched by addition of sat. NH$_4$Cl(aq) (100 mL) and the phases were separated. The aq phase was extracted twice with EtOAc and the combined organics were washed with brine, dried over Na$_2$SO$_4$, filtered and evaporated to yield 2.29 g (quant.) of the title compound which was used without further purification. $^1$H NMR (400 MHz, CHLOROFORM-d) δ 1.02 (s, 3H), 1.11 (s, 3H), 1.27 (s, 9H), 2.60 (s, 2H), 4.52 (dd, 1H), 5.28 (dd, 1H), 6.00 (dd, 1H), 7.03 (d, 1H), 7.36 (dd, 1H), 7.88 (d, 1H). MS (ES+) m/z 370, 372 [M+H]$^+$ Step 4: 6-bromo-2,2-dimethyl-1-vinyl-2,3-dihydro-1H-inden-1-amine A solution of N-(6-bromo-2,2-dimethyl-1-vinyl-2,3-dihydro-1H-inden-1-yl)-2-methylpropane-2-sulfinamide (2.29 g, 6.18 mmol) in dry dichloromethane (2 mL) was cooled to 0° C. HCl (4 M in dioxane, 6.18 mL, 24.73 mmol) was added dropwise and the resulting mixture was stirred at r.t. for 30 min. A white precipitate had formed. Et$_2$O (60 mL) was added and the solid was filtered off. Dichloromethane and sat. NaHCO$_3$ (aq) was added and the phases were separated. The organic layer was dried over Na$_2$SO$_4$, filtered and concentrated to afford 1.12 g (68.0%) of the title compound. $^1$H NMR (500 MHz, CHLOROFORM-d) δ 0.99 (s, 3H), 1.05 (s, 3H), 1.40 (br. s., 2H), 2.67 (s, 2H), 4.98 (dd, 1H), 5.13 (dd, 1H), 5.96 (dd, 1H), 7.06 (d, 1H), 7.28 (s, 1H), 7.31 (dd, 1H). MS (ES+) m/z 249, 251 [M−NH2]$^+$ Step 5: N-(6-bromo-2,2-dimethyl-1-vinyl-2,3-dihydro-1H-inden-1-yl)-2-fluoroacrylamide To a suspension of 6-bromo-2,2-dimethyl-1-vinyl-2,3-dihydro-1H-inden-1-amine (1.12 g, 4.21 mmol) and 2-fluoropropenoic acid (0.568 g, 6.31 mmol) in dry EtOAc (20 mL) were added 1-propanephosphonic acid cyclic anhydride (T3P) (3.76 mL, 6.31 mmol) and triethylamine (1.47 mL, 10.52 mmol) under nitrogen. After 1.5 h, more 2-fluoropropenoic acid (0.189 g, 2.10 mmol) and 1-propanephosphonic acid cyclic anhydride (T3P) (1.25 mL, 2.10 mmol) was added and stirring continued. After a total of 2.5 days, water was added and the phases were separated. The aq layer was extracted twice with EtOAc and the combined organics were dried over MgSO$_4$, filtered and concentrated. Purification by column chromatography using a gradient of 0-10% EtOAc in heptane as eluent afforded 1.097 g (77%) of the title compound. $^1$H NMR (500 MHz, CHLOROFORM-d) δ 1.10 (s, 3H), 1.22 (s, 3H), 2.67-2.77 (m, 2H), 4.71 (d, 1H), 5.13 (dd, 1H), 5.23 (d, 1H), 5.62-5.75 (m, 1H), 6.36 (dd, 1H), 6.62 (br. s., 1H), 7.08 (d, 1H), 7.38 (dd, 1H), 7.53 (d, 1H). MS (ES−) m/z 336, 338 [M−H]$^-$ Step 6: 6-bromo-4'-fluoro-2,2-dimethyl-2,3-dihydrospiro[indene-1,2'-pyrrol]-5'(1'H)-one To a solution of N-(6-bromo-2,2-dimethyl-1-vinyl-2,3-dihydro-1H-inden-1-yl)-2-fluoroacrylamide (0.300 g, 0.89 mmol) in dry toluene (30 mL) under nitrogen was added Hoveyda-Grubbs catalyst, 2nd Generation (56 mg, 0.09 mmol) and the mixture was stirred at 100° C. overnight. A second portion of Hoveyda-Grubbs catalyst, 2nd Generation (56 mg, 0.09 mmol) was added and the reaction was continued. After 24 h, a new portion of Hoveyda-Grubbs catalyst, 2nd Generation (56 mg, 0.09 mmol) was added, as well as after 48 h. After 2.5 days the mixture was cooled to r.t. and concentrated. Purification by column chromatography using a gradient of 0-50% EtOAc in heptane as eluent yielded 96 mg (34.9%) of the title compound. $^1$H NMR (500 MHz, CHLOROFORM-d) δ ppm 1.09 (s, 3H) 1.12 (s, 3H) 2.83 (m, 2H) 6.19 (br. s., 1H) 6.27 (d, 1H) 7.14 (d, 1H) 7.25 (d, 1H) 7.41 (dd, 1H). MS (ES+) m/z 310, 312 [M+H]$^+$ Step 7: 6-bromo-4'-fluoro-2,2-dimethyl-2,3-dihydrospiro[indene-1,2'-pyrrol]-5'-amine To solution of 6-bromo-4'-fluoro-2,2-dimethyl-2,3-dihydrospiro[indene-1,2'-pyrrol]-5'(1'H)-one (96 mg, 0.31 mmol) in dry pyridine (3 mL) was added phosphorus pentasulfide (0.124 g, 0.28 mmol) and the reaction was heated at reflux for 3 h. The reaction was allowed to cool to r.t. and ammonia (7N in MeOH, 4.20 mL, 29.43 mmol) and tert-butyl hydroperoxide (70% in water, 0.606 mL, 4.41 mmol) were added. After stirring for 3 days, the reaction mixture was concentrated somewhat and DCM and water were added. The layers were separated and the aq phase was extracted with DCM three times. The combined organic layers were washed with brine, dried over Na$_2$SO$_4$, filtered and evaporated. The mixture was purified by column chromatography using a gradient of 0-10% MeOH containing 0.1M NH$_3$ in dichloromethane as eluent, followed by preparative chromatography to afford 14.5 mg, (15.9%) of the title compound. ¹H NMR (500 MHz, CHLOROFORM-d) δ ppm 1.06 (2×s, 2×3H) 2.73 (d, 1H) 3.02 (d, 1H) 6.40 (d, 1H) 7.05 (s, 1H) 7.13 (d, 1H) 7.32 (dd, 1H). MS (ES+) m/z 309, 311 [M+H]⁺

Step 8: 4'-Fluoro-2,2-dimethyl-6-(pyrimidin-5-yl)-2,3-dihydrospiro[indene-1,2'-pyrrol]-5'-amine 6-bromo-4'-fluoro-2,2-dimethyl-2,3-dihydrospiro[indene-1,2'-pyrrol]-5'-amine (13 mg, 0.04 mmol), pyrimidin-5-ylboronic acid (6.8 mg, 0.05 mmol), sodium tetrachloropalladate(II) (0.6 mg, 2.10 µmol) and 3-(di-tert-butylphosphonium)propane sulfonate (1.1 mg, 4.20 µmol) were placed in a microwave tube. 2-Methyl tetrahydrofuran (0.5 mL) was added followed by aqueous potassium carbonate (2 M, 63 µL, 0.13 mmol). The mixture was degassed and the vial was capped and heated at 100° C. for 30 min in a microwave reactor. More pyrimidin-5-ylboronic acid (6.8 mg, 0.05 mmol), sodium tetrachloropalladate(II) (0.6 mg, 2.10 µmol) and 3-(di-tert-butylphosphonium)propane sulfonate (1.1 mg, 4.20 µmol) was added and the mixture was heated at 100° C. for another 30 min. Water and EtOAc were added and the phases were separated. The aq phase was extracted once more with EtOAc and the combined organics were dried over MgSO₄, filtered and evaporated. Purification by preparative chromatography afforded 9 mg (69.4%) of the title compound. ¹H NMR (500 MHz, CHLOROFORM-d) δ ppm 1.11 (s, 3H) 1.13 (s, 3H) 2.89 (d, 1H) 3.15 (d, 1H) 4.66 (br. s, 2H) 6.48 (d, 1H) 7.13 (s, 1H) 7.43 (m, 2H) 8.89 (s, 2H) 9.17 (s, 1H). MS (ES+) m/z 309 [M+H]⁺

Intermediates:
6-(3-Fluoropropoxy)-2,3-dihydro-1H-inden-1-one

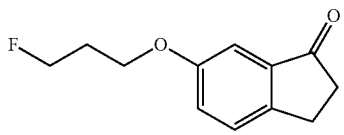 [SMILES: O=C1CCc2ccc(OCCCF)cc21]

To a solution of 6-hydroxy-2,3-dihydro-1H-inden-1-one (4 g, 27.00 mmol) in THF (140 mL) were 3-fluoropropan-1-ol (2.232 mL, 29.70 mmol), Triphenylphosphine (10.62 g, 40.50 mmol) and diisopropyl azodicarboxylate (7.97 mL, 40.50 mmol) slowly added and stirred at r.t overnight. The mixture was concentrated. Purification of the product by silica gel chromatography using Heptane/ethylacetate 4:1-3:1 as eluent gave the title compound (6.25 g, 111%). NMR: ¹H NMR (500 MHz, CHLOROFORM-d) δ ppm 2.12-2.32 (m, 2H) 2.66-2.81 (m, 2H) 3.00-3.15 (m, 2H) 4.13 (t, 2H) 4.61 (t, 1H) 4.70 (t, 1H) 7.15-7.23 (m, 2H) 7.38 (d, 1H).

6'-(3-fluoropropoxy)spiro[cyclohexane-1,2'-indene]-1',4(3'H)-dione

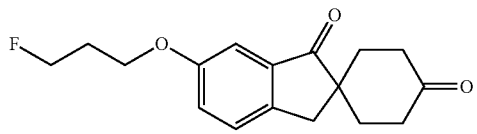 [SMILES: O=C1CCC2(CC1)Cc1ccc(OCCCF)cc1C2=O]

To a mixture of 6-(3-fluoropropoxy)-2,3-dihydro-1H-inden-1-one (6.25 g, 30 mmol) and methyl acrylate (5.96 ml, 66.00 mmol) in 2-methyl THF (26.4 ml) cooled to 0° C. was added Potassium tert-butoxide (3.70 g, 33.00 mmol) in portions. After stirring for 1 h at rt, more methyl acrylate (3.0 ml, 33.24 mmol) and Potassium tert-butoxide (1.7 g, 15.15 mmol) were added, after stirring at r.t for another 15 min, water (39.6 ml) and potassium hydroxide (2.52 g, 45.00 mmol) were added and the mixture was heated at reflux. The reaction mixture was partitioned between brine and ethylacetate, the organic phase was dried over MgSO₄ and concentrated. Purification of the residue by column chromatography using heptane/EtOAc, 2:1-1:1 as eluent gave the title compound (2.100 g, 24.11%). MS (ES+) m/z 291 (M+H)⁺. ¹H NMR (500 MHz, CHLOROFORM-d) δ ppm 1.82-1.93 (m, 2H) 2.14-2.28 (m, 4H) 2.40-2.51 (m, 2H) 2.69 (dt, 2H) 3.16 (s, 2H) 4.14 (t, 2H) 4.61 (t, 1H) 4.71 (t, 1H) 7.20-7.23 (m, 1H) 7.23-7.26 (m, 1H) 7.39 (d, 1H).

6'-(3-fluoropropoxy)-4-hydroxyspiro[cyclohexane-1,2'-inden]-1'(3'H)-one

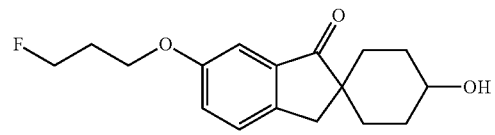 [SMILES: O=C1c2cc(OCCCF)ccc2CC12CCC(O)CC2]

To a solution of 6'-(3-fluoropropoxy)spiro[cyclohexane-1,2'-indene]-1',4(3'H)-dione (2.1 g, 7.23 mmol) in dichloromethane (15 mL), was Borane tert-butylamine complex (0.239 g, 2.75 mmol) added at 0° C. After 1 h was conc HCl (1 mL) added, followed by 20% aqueous NaCl (20 mL) solution. The reaction mixture was allowed to reach room temperature and was stirred for 30 min. Work up together with EN05242-69. The phases were separated and to the water phase were charged with DCM and H₂O. The organic phases were combined, concentrated and dried under vacuum o.n to give a white solid, 6'-(3-fluoropropoxy)-4-hydroxyspiro[cyclohexane-1,2'-inden]-1'(3'H)-one (2.0 g, 95%). MS (ES+) m/z 293 (M+H)+

(1r,4r)-6'-(3-fluoropropoxy)-4-[(2H3)methyloxy]spiro[cyclohexane-1,2'-inden]-1'(3'H)-one

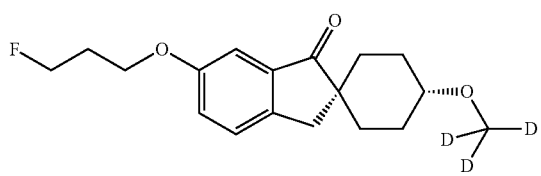 [SMILES: [2H]C([2H])([2H])O[C@H]1CC[C@]2(CC1)Cc1ccc(OCCCF)cc1C2=O]

(1r,4r)-6'-(3-fluoropropoxy)-4-hydroxyspiro[cyclohexane-1,2'-inden]-1'(3'H)-one (2.0 g, 6.84 mmol) was dissolved in 2-methyl THF (45.1 ml) under an inert atmosphere and the solution was cooled to 0° C. Iodomethane-D₃ (0.556 ml, 8.89 mmol) was added followed by portionwise addition of potassium tert-butoxide (1.075 g, 9.58 mmol). The resulting mixture was stirred at r.t. for 3 h. The phases were separated and the organic layer was dried over MgSO₄ and concentrated to afford the title compound (2.2 g, 103%). The product was used as such in the next step.

47

N-[(1r,1'E,4r)-6'-(3-fluoropropoxy)-4-[(2H3)methyloxy]spiro[cyclohexane-1,2'-inden]-1'(3'H)-ylidene]-2-methylpropane-2-sulfinamide

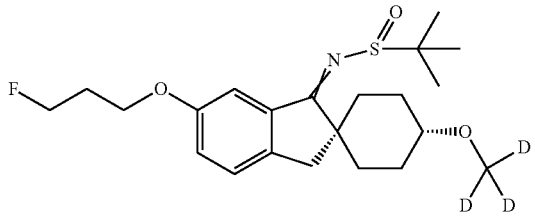 [SMILES: [2H]C([2H])([2H])O[C@H]1CC[C@]2(CC1)Cc1ccc(OCCCF)cc1C2=NS(=O)C(C)(C)C]

(1r,4r)-6'-(3-fluoropropoxy)-4-[(2H3)methyloxy]spiro[cyclohexane-1,2'-inden]-1'(3'H)-one (3.85 g, 12.44 mmol), 2-methylpropane-2-sulfinamide (1.291 g, 16.18 mmol), 2-methyltetrahydrofuran (25 ml) and titanium ethoxide (4.53 ml, 24.89 mmol) were heated to reflux overnight. More of 2-methylpropane-2-sulfinamide (1.96 g, 16.18 mmol) and titanium ethoxide (4.105 ml, 19.12 mmol) were added, the reaction mixture was heated to reflux for another night. More 2-methylpropane-2-sulfinamide (1.57 g, 14.21 mmol) and titanium ethoxide (3.59 g, 16.98 mmol) added, the reaction mixture was heated to reflux for 4 more days. The reaction was allowed to cool to r.t. whereafter it was diluted with EtOAc (150 mL). Water (50 mL) was added dropwise over 10 min under vigorous stirring and then the mixture was left standing without stirring for 1.5 h. Solids were filtered off and the organics were evaporated. Purification of the residue by silica column chromatography using hept/EtOAc, 2:1-1:1 as eluent gave the title compound (2.3 g, 45%). MS (ES+) m/z 413 (M+H)+.

1'-ethenyl-6'-(3-fluoropropoxy)-4-[(2H3)methyloxy]-1',3'-dihydrospiro[cyclohexane-1,2'-inden]-1'-amine

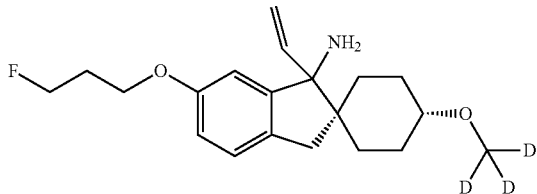

A solution of N-{1'-ethenyl-6'-(3-fluoropropoxy)-4-[(2H3)methyloxy]-1',3'-dihydrospiro[cyclohexane-1,2'-inden]-1'-yl}-2-methylpropane-2-sulfinamide (1.8 g, 4.09 mmol) in dry dichloromethane (2 mL) was cooled to 0° C. HCl (4 M in dioxane) (4.09 mL, 16.34 mmol) was added dropwise to the reaction mixture and was stirred at r.t. for 30 min. EtOAc and saturated aqueous NaHCO₃ were added and the phases were separated. The organic layer was dried over MgSO₄ and concentrated to afford the title compound. The material was used in the next step as such.

48

N-{1'-ethenyl-6'-(3-fluoropropoxy)-4-[(2H3)methyloxy]-1',3'-dihydrospiro[cyclohexane-1,2'-inden]-1'-yl}-2-fluoroprop-2-enamide

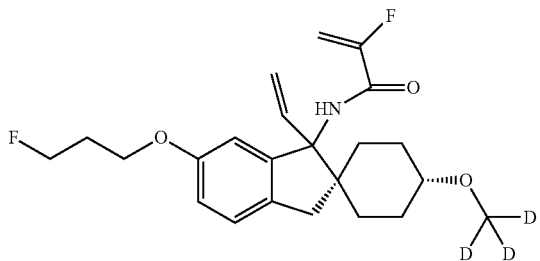

To a suspension of 1'-ethenyl-6'-(3-fluoropropoxy)-4-[(2H3)methyloxy]-1',3'-dihydrospiro[cyclohexane-1,2'-inden]-1'-amine (1.376 g, 4.09 mmol) and in dry ethyl acetate (30 mL) were 1-propanephosphonic acid cyclic anhydride (3.67 mL, 6.14 mmol) and triethylamine (0.570 ml, 4.09 mmol) added at 0° C. under an nitrogen atmosphere. The reaction mixture was then allowed to reach r.t. The mixture was stirred 3 days, then more 1-propanephosphonic acid cyclic anhydride (1.223 mL, 2.05 mmol) and triethylamine (0.285 mL, 2.05 mmol) was added, stirred for another 3 h. Water was then added and the phases were separated. The aqueous phase was extracted with EtOAc and the combined organics were dried over Na₂SO₄ and evaporated. Purification of the residue by silica gel chromatography using heptane/ethylacetate 5:1-4:1-3:1 as eluant gave the title compound (0.45 g, 27% yield). The product was used as such in the next step.

4"-fluoro-6'-(3-fluoropropoxy)-4-[(2H3)methyloxy]-3'H-dispiro[cyclohexane-1,2'-indene-1',2"-pyrrol]-5"(1"H)-one

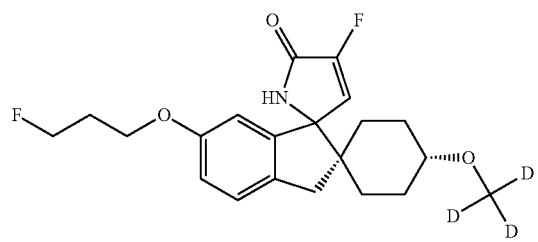

A mixture of N-{1'-ethenyl-6'-(3-fluoropropoxy)-4-[(2H3)methyloxy]-1',3'-dihydrospiro[cyclohexane-1,2'-inden]-1'-yl}-2-fluoroprop-2-enamide (0.446 g, 1.09 mmol) in dry toluene (60 mL) under nitrogen was heated to 100° C. Hoveyda-Grubbs Catalyst 2nd Generation (0.069 g, 0.11 mmol) was and the mixture was left stirring at the same temperature. After 50 min, more Hoveyda-Grubbs Catalyst 2nd Generation (0.069 g, 0.11 mmol) was added and the mixture was stirred overnight. More of Hoveyda-Grubbs Catalyst 2nd Generation (0.069 g, 0.11 mmol) was added. After 5 h more Hoveyda-Grubbs Catalyst 2nd Generation (0.686 g, 1.09 mmol) was added and the reaction was heated over a weekend. More Hoveyda-Grubbs Catalyst 2nd Generation (0.686 g, 1.09 mmol) was again added and the reaction was heated overnight. The reaction mixture was allowed to cool to r.t., and concentrated. Purification of the residue by silica gel chromatography using heptane/ethylacetate 5:1-4:1-3:1-1:1-1:2 as eluant gave the title compound (0.26 g, 62% yield). MS (ES+) m/z 381 (M+H)+. $^1$H NMR (500 MHz, DMSO-d$_6$) δ ppm 1.15-1.30 (m, 5H) 1.33-1.57 (m, 3H) 1.81-1.94 (m, 2H) 2.00-2.13 (m, 3H) 2.77-2.98 (m, 2H) 2.99-3.09 (m, 1H) 3.36 (br. s., OH) 3.93-4.12 (m, 3H) 4.53 (t, 1H) 4.63 (t, 1H) 6.52-6.60 (m, 1H) 6.80 (d, 1H) 6.81-6.85 (m, 1H) 7.15-7.22 (m, 3H) 8.96-9.04 (m, 1H)

4"-fluoro-6'-(3-fluoropropoxy)-4-[(2H3)methyloxy]-3'H-dispiro[cyclohexane-1,2'-indene-1',2"-pyrrole]-5"(1"H)-thione

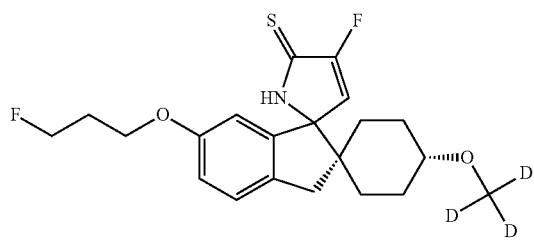

To solution of 4"-fluoro-6'-(3-fluoropropoxy)-4-[(2H3)methyloxy]-3'H-dispiro[cyclohexane-1,2'-indene-1',2"-pyrrol]-5"(1"H)-one (0.257 g, 0.68 mmol) in dry pyridine (11.65 ml) was added phosphorus pentasulfide (0.270 g, 0.61 mmol) and the reaction heated at reflux. After 3 h was the reaction allowed to cool to r.t. and the reaction mixture was taken to the next step. MS (ES+) m/z 397 (M+H)+.

Examples 10 and 11: 4"-fluoro-6'-(3-fluoropropoxy)-4-[(2H3)methyloxy]-3'H-dispiro[cyclohexane-1,2'-indene-1',2"-pyrrol]-5"-amine

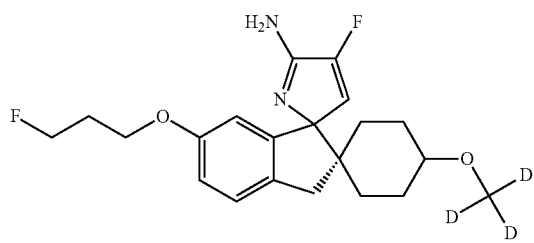

To the solution of 4"-fluoro-6'-(3-fluoropropoxy)-4-[(2H3)methyloxy]-3'H-dispiro[cyclohexane-1,2'-indene-1',2"-pyrrole]-5"(1"H)-thione (270 mg, 0.68 mmol) in pyridine (12 mL) was ammonia (7N in MeOH) (9.71 mL, 68.00 mmol) and tert-butyl hydroperoxide (70% in water) (1.401 mL, 10.20 mmol) added and the reaction was stirred at r.t. for 3 days. The reaction mixture was concentrated somewhat and DCM and water were added and the layers separated. The aqueous phase was extracted with DCM. The combined organic phases were washed with brine, dried over Na$_2$SO$_4$, filtered and concentrated. Purification of the residue by silica gel chromatography using EtOAc, EtOAc/NH$_3$ (7M in methanol) solution 10:1 as eluant followed by preparative HPLC afforded 2 diastereomers:

Example 10, Isomer 1

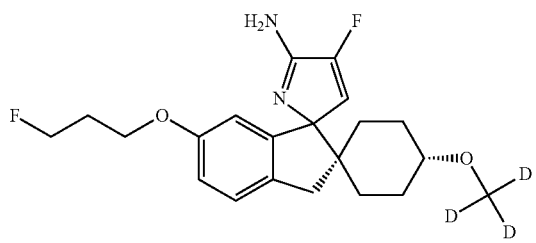

4"-fluoro-6'-(3-fluoropropoxy)-4-[(2H3)methyloxy]-3'H-dispiro[cyclohexane-1,2'-indene-1',2"-pyrrol]-5"-amine (30.6 mg, 12%). MS (ES+) m/z 380 [M+H]+. $^1$H NMR (500 MHz, DMSO-d$_6$) δ ppm 1.05-1.26 (m, 3H) 1.35-1.54 (m, 3H) 1.83 (d, 2H) 1.97-2.11 (m, 2H) 2.74-2.93 (m, 2H) 2.93-3.03 (m, 1H) 3.87-4.02 (m, 2H) 4.52 (t, 1H) 4.61 (t, 1H) 6.26 (br. s., 1H) 6.43 (br. s., 2H) 6.64 (br. s., 1H) 6.70 (dd, 1H) 7.13 (d, 1H)

Example 11, Isomer 2

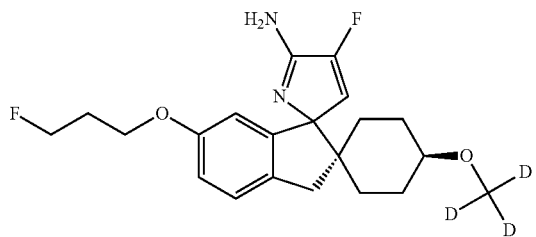

4"-fluoro-6'-(3-fluoropropoxy)-4-[(2H3)methyloxy]-3'H-dispiro[cyclohexane-1,2'-iii indene-1',2"-pyrrol]-5"-amine (4.8 mg, 2%). MS (ES+) m/z 380 [M+H]+. $^1$H NMR (500 MHz, DMSO-d$_6$) δ ppm 1.08-1.26 (m, 2H) 1.35-1.53 (m, 3H) 1.58-1.79 (m, 3H) 1.92-2.11 (m, 2H) 2.76-2.97 (m, 2H) 3.85-4.03 (m, 2H) 4.52 (t, 1H) 4.62 (t, 1H) 6.26 (br. s., 1H) 6.40 (br. s., 2H) 6.64 (br. s., 1H) 6.70 (dd, 1H) 7.12 (d, 1H)

Intermediate 3: 3-Chloro-2-methyl-5-(4,4,5,5-tetramethyl-1,3,2-dioxaborolan-2-yl)pyridine

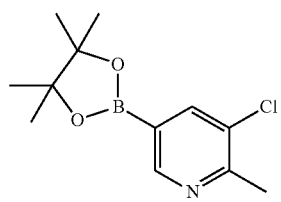 [SMILES: Cc1ncc(B2OC(C)(C)C(C)(C)O2)cc1Cl]

A suspension of 4,4,4',4',5,5,5',5'-octamethyl-2,2'-bi(1,3,2-dioxaborolane) (0.836 g, 3.29 mmol), 5-bromo-3-chloro-2-methylpyridine (0.34 g, 1.65 mmol), potassium acetate (0.485 g, 4.94 mmol) in dioxane (5 mL) was degassed with a stream of argon for a couple of minutes. 1,1'-bis(diphenylphosphino)ferrocene-palladium(II)dichloride dichloromethane complex (0.067 g, 0.08 mmol) was added and the mixture was heated at reflux under N2 for 1.5 h. The mixture was allowed to cool and filtered. The filter cake was washed with EtOAc. The filtrate was concentrated in vacuo and column chromatography using EtOAc 0% to 80% in heptane gave 442 mg (100%) of the title compound. $^1$H NMR (500 MHz, CDCl$_3$) δ ppm 1.35 (s, 12H), 2.65 (s, 3H), 7.95-8.03 (m, 1H), 8.69 (d, 1H); MS (ES+) m/z: 172 [M–C$_6$H$_9$]$^+$.

Intermediate 4:
3-Bromo-5-(methoxymethyl)benzonitrile

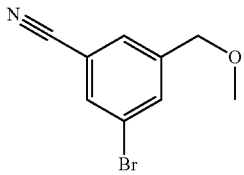

May be prepared by the following method:

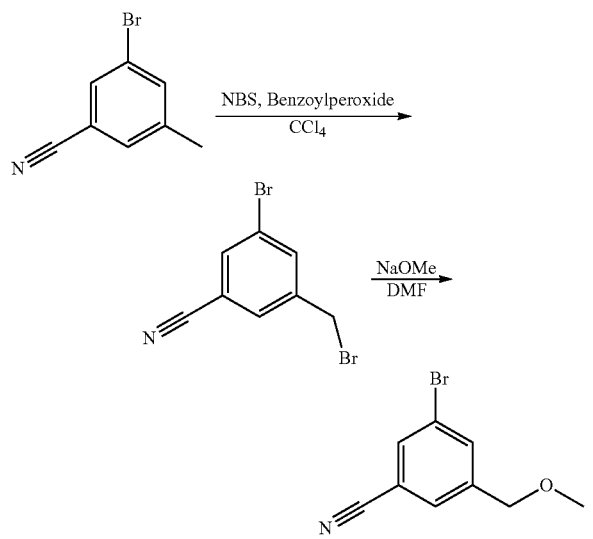

Intermediate 5:
1-Bromo-3-chloro-5-(methoxymethyl)benzene

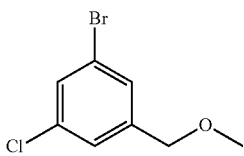

May be prepared by the following method:

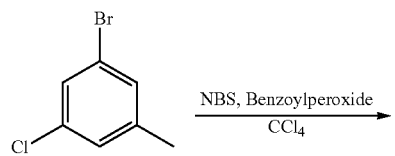

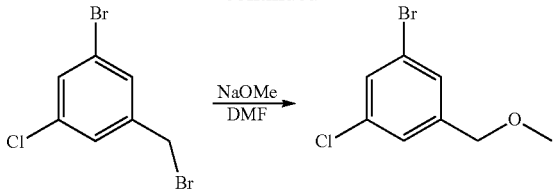

Intermediate 6:
1-Bromo-3-fluoro-5-(methoxymethyl)benzene

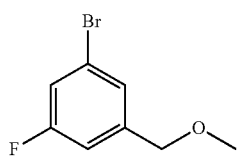

May be prepared by the following method:

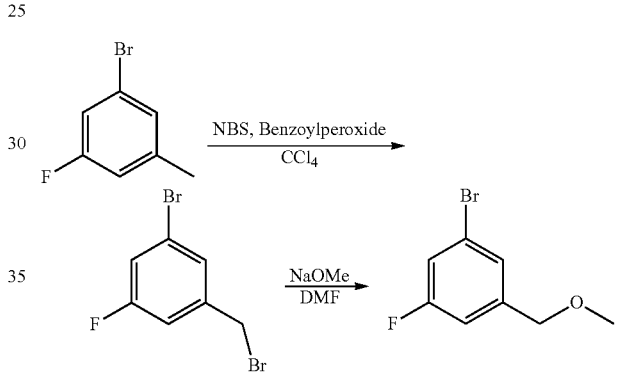

Intermediate 7: 6'-Bromo-4-(difluoromethoxy)spiro[cyclohexane-1,2'-indane]-1'-one

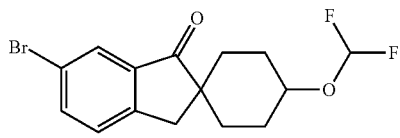 [SMILES: O=C1c2cc(Br)ccc2CC12CCC(OC(F)F)CC2]

6'-bromo-4-hydroxyspiro[cyclohexane-1,2'-inden]-1'(3'H)-one (mixture of isomers) (5 g, 16.94 mmol) was co-evaporated with dry MeCN twice after which it was dissolved in dry acetonitrile (215 mL), Cuprous iodide (0.323 g, 1.69 mmol) was added and the resulting mixture was heated at 60° C. for 5 min under Argon. 2-(Fluorosulphonyl)difluoroacetic acid (2.421 mL, 22.02 mmol) was added in a stream and the reaction mixture was heated for 50 min. Water and diethyl ether were added. The phases were separated and the aqueous phase was extracted twice with Et$_2$O. The combined organic phases were dried over Na$_2$SO$_4$, filtered and concentrated. Column chromatography using EtOAc 14% to 67% in heptanes yielded 2.2 g (37%) of the title compound. 1H NMR (500 MHz, DMSO-d$_6$) δ ppm 1.43-1.67 (m, 6H), 1.96-2.05 (m, 2H), 3.04 (s, 2H), 4.09-4.20 (m, 1H), 6.74 (t, 1H), 7.56 (d, 1H), 7.78 (d, 1H), 7.87 (dd, 1H); MS (ES+) m/z 345 [M+H]+

Intermediate 8: 6'-bromo-4-methoxy-4-methylspiro[cyclohexane-1,2'-inden]-1'(3'H)-one

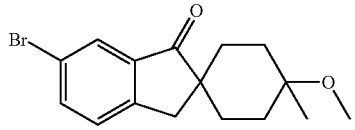 [SMILES: COC1(C)CCC2(CC1)Cc1ccc(Br)cc1C2=O]

May be prepared by the following method:

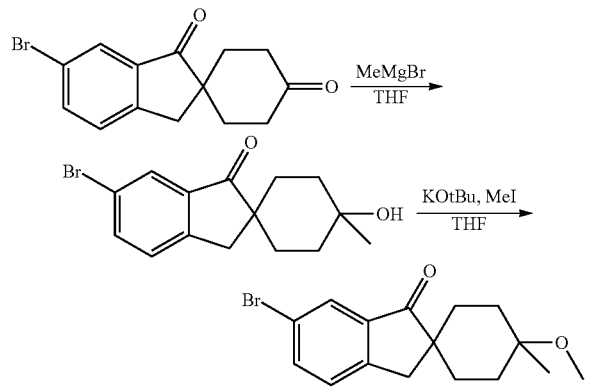

Intermediate 9: 5-Bromo-4'-methoxy-4'-methyl-3H-spiro[1-benzofuran-2,1'-cyclohexan]-3-one

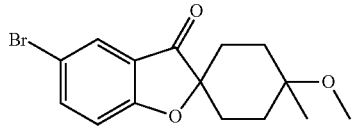 [SMILES: COC1(C)CCC2(CC1)Oc1ccc(Br)cc1C2=O]

May be prepared by the following method:

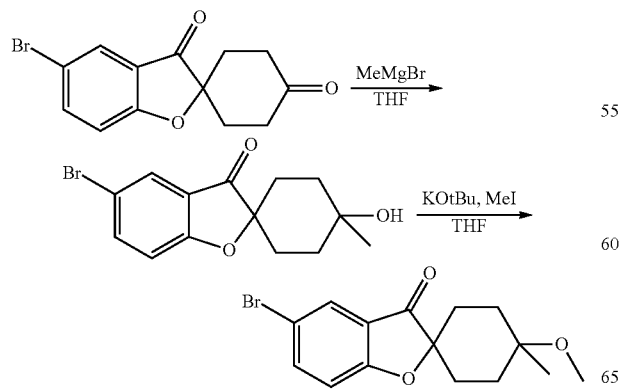

Intermediate 10

5-Bromo-4'-(difluoromethoxy)-3H-spiro[1-benzofuran-2,1'-cyclohexan]-3-one

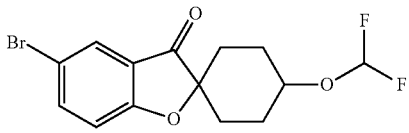 [SMILES: O=C1c2cc(Br)ccc2OC12CCC(OC(F)F)CC2]

May be prepared by the following method:

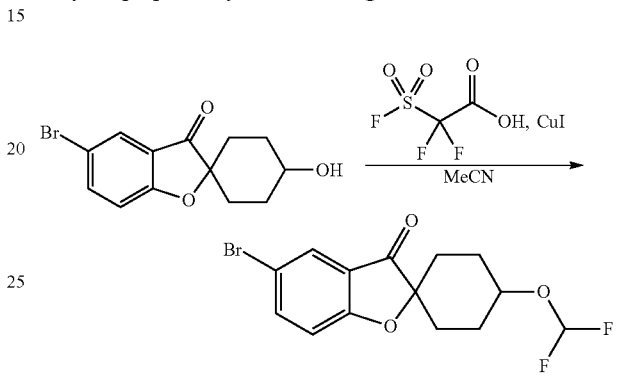

The following compounds may be prepared using 6'-bromo-4''-fluoro-4-methoxy-3'H-dispiro[cyclohexane-1,2'-indene-1',2''-pyrrol]-5''-amine (Example 1, step 7) using methods described above. Additional reagents and methods are listed.

Example 12: 4''-fluoro-4-methoxy-6'-(pyridin-3-yl)-3'H-dispiro[cyclohexane-1,2'-indene-1',2''-pyrrol]-5''-amine

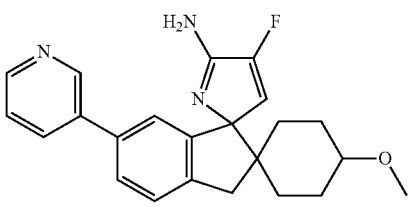 [SMILES: COC1CCC2(CC1)Cc1ccc(-c3cccnc3)cc1C21C=C(F)C(N)=N1]

May be prepared with Pyridine-3-boronic acid by method (xiii).

Example 13: 4''-fluoro-6'-(5-fluoropyridin-3-yl)-4-methoxy-3'H-dispiro[cyclohexane-1,2'-indene-1',2''-pyrrol]-5''-amine

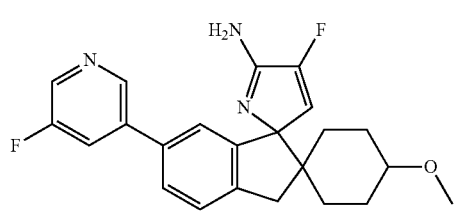 [SMILES: COC1CCC2(CC1)Cc1ccc(-c3cncc(F)c3)cc1C21C=C(F)C(N)=N1]

May be prepared with 5-Fluoropyridine-3-boronic acid by method (xiii)

Example 14: 6'-(5-chloropyridin-3-yl)-4"-fluoro-4-methoxy-3'H-dispiro[cyclohexane-1,2'-indene-1',2"-pyrrol]-5"-amine

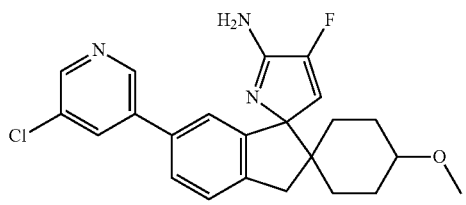 [SMILES: COC1CCC2(CC1)Cc1ccc(-c3cncc(Cl)c3)cc1C21C=C(F)C(N)=N1]

May be prepared with 5-Chloropyridine-3-boronic acid by method (xiii)

Example 15: 6'-(5-chloro-6-methylpyridin-3-yl)-4"-fluoro-4-methoxy-3'H-dispiro[cyclohexane-1,2'-indene-1',2"-pyrrol]-5"-amine

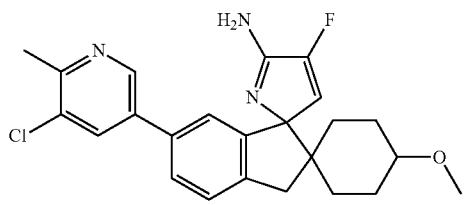 [SMILES: COC1CCC2(CC1)Cc1ccc(-c3cnc(C)c(Cl)c3)cc1C21C=C(F)C(N)=N1]

May be prepared with Intermediate 3 by method (xiii)

Example 16: 4"-fluoro-4-methoxy-6'-(5-methylpyridin-3-yl)-3'H-dispiro[cyclohexane-1,2'-indene-1',2"-pyrrol]-5"-amine

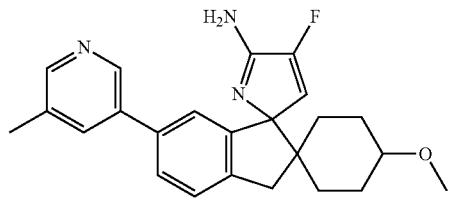

May be prepared with 5-Methylpyridine-3-boronic acid by method (xiii)

Example 17: 4"-fluoro-4-methoxy-6'-(3-methoxyphenyl)-3'H-dispiro[cyclohexane-1,2'-indene-1',2"-pyrrol]-5"-amine

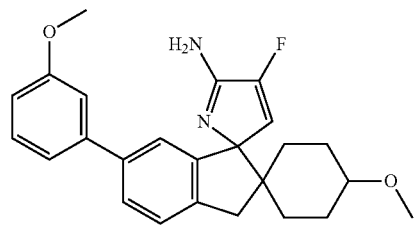

May be prepared with 3-Methoxyphenylboronic acid by method (xiii)

Example 18: 6'-(3-chlorophenyl)-4"-fluoro-4-methoxy-3'H-dispiro[cyclohexane-1,2'-indene-1',2"-pyrrol]-5"-amine

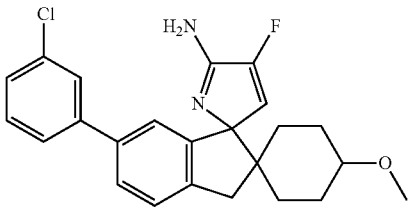 [SMILES: COC1CCC2(CC1)Cc1ccc(-c3cccc(Cl)c3)cc1C21C=C(F)C(N)=N1]

May be prepared with 3-Chlorophenylboronic acid by method (xiii)

Example 19: 3-(5"-amino-4"-fluoro-4-methoxy-3'H-dispiro[cyclohexane-1,2'-indene-1',2"-pyrrol]-6'-yl)-5-fluorobenzonitrile

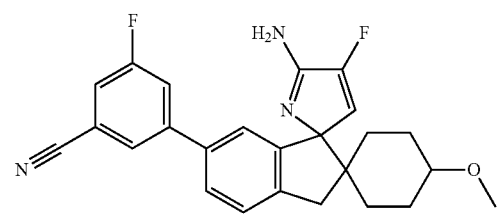 [SMILES: COC1CCC2(CC1)Cc1ccc(-c3cc(F)cc(C#N)c3)cc1C21C=C(F)C(N)=N1]

May be prepared with 3-Cyano-5-fluorophenylboronic acid by method (xiii)

Example 20: 3-(5"-amino-4"-fluoro-4-methoxy-3'H-dispiro[cyclohexane-1,2'-indene-1',2"-pyrrol]-6'-yl)-5-chlorobenzonitrile

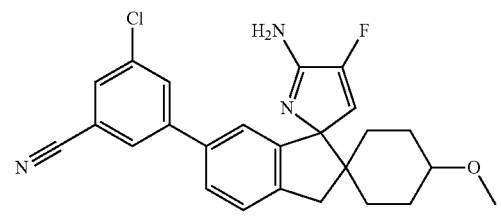

May be prepared with 3-Chloro-5-cyanophenylboronic acid by method (xiii)

Example 21: 4"-fluoro-4-methoxy-6'-phenyl-3'H-dispiro[cyclohexane-1,2'-indene-1',2"-pyrrol]-5"-amine

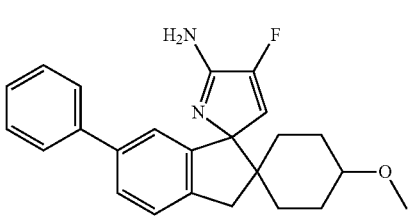 [SMILES: COC1CCC2(CC1)Cc1ccc(-c3ccccc3)cc1C21C=C(F)C(N)=N1]

May be prepared with Phenylboronic acid by method (xiii)

Example 22: 4"-fluoro-6'-[3-fluoro-5-(methoxymethyl)phenyl]-4-methoxy-3'H-dispiro[cyclohexane-1,2'-indene-1',2"-pyrrol]-5"-amine

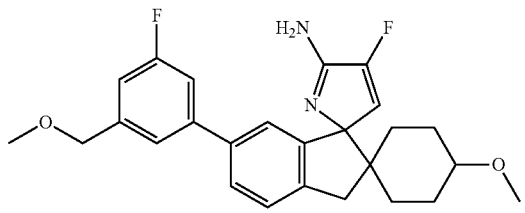

May be prepared with Intermediate 6 by method (xiii)

Example 23: 6'-[3-chloro-5-(methoxymethyl)phenyl]-4"-fluoro-4-methoxy-3'H-dispiro[cyclohexane-1,2'-indene-1',2"-pyrrol]-5"-amine

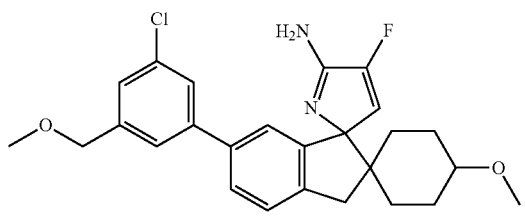

May be prepared with Intermediate 5 by method (xiii)

Example 24: 3-(5"-amino-4"-fluoro-4-methoxy-3'H-dispiro[cyclohexane-1,2'-indene-1',2"-pyrrol]-6'-yl)-5-(methoxymethyl)benzonitrile

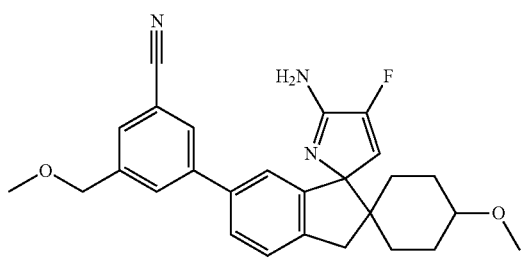

May be prepared with Intermediate 4 by method (xiii)

The following compound may be prepared using Intermediate 8 which can be converted to 6'-bromo-4"-fluoro-4-methoxy-4-methyl-3'H-dispiro[cyclohexane-1,2'-indene-1',2"-pyrrol]-5"-amine using methods described above. Additional reagents and methods are listed.

Example 25: 4"-fluoro-4-methoxy-4-methyl-6'-(pyrimidin-5-yl)-3'H-dispiro[cyclohexane-1,2'-indene-1',2"-pyrrol]-5"-amine

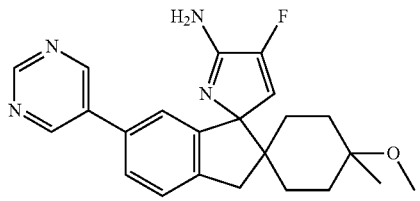 [SMILES: COC1(C)CCC2(CC1)Cc1ccc(-c3cncnc3)cc1C21C=C(F)C(N)=N1]

May be prepared with Pyrimidine-5-boronic acid by method (xiii)

The following compound may be prepared using Intermediate 7 which can be converted to 6'-bromo-4-(difluoromethoxy)-4"-fluoro-3'H-dispiro[cyclohexane-1,2'-indene-1',2"-pyrrol]-5"-amine using methods described above. Additional reagents and methods are listed.

Example 26: 4-(difluoromethoxy)-4"-fluoro-6'-(pyrimidin-5-yl)-3'H-dispiro[cyclohexane-1,2'-indene-1',2"-pyrrol]-5"-amine

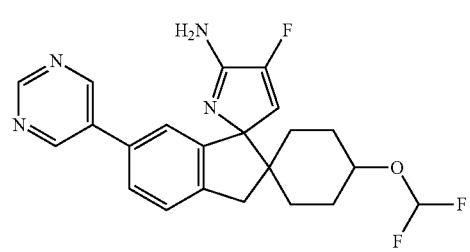

May be prepared with Pyrimidine-5-boronic acid by method (xiii)

The following compounds may be made from 5-bromo-4'-methoxy-3H-spiro[1-benzofuran-2,1'-cyclohexan]-3-one which can be converted to 5'-bromo-4"-fluoro-4-methoxy-dispiro[cyclohexane-1,2'-[1]benzofuran-3',2"-pyrrol]-5"-amine using methods described above. Additional reagents and methods are listed.

Example 27: 4"-fluoro-4-methoxy-5'-(pyrimidin-5-yl)dispiro[cyclohexane-1,2'-[1]benzofuran-3',2"-pyrrol]-5"-amine

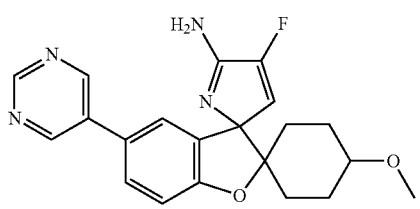 [SMILES: COC1CCC2(CC1)Oc1ccc(-c3cncnc3)cc1C21C=C(F)C(N)=N1]

May be prepared with Pyrimidine-5-boronic acid by method (xiii)

Example 28: 4"-fluoro-4-methoxy-5'-(pyridin-3-yl)dispiro[cyclohexane-1,2'-[1]benzofuran-3',2"-pyrrol]-5"-amine

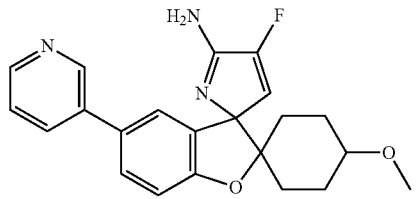

May be prepared with Pyridine-3-boronic acid by method (xiii)

Example 29: 4"-fluoro-5'-(5-fluoropyridin-3-yl)-4-methoxydispiro[cyclohexane-1,2'-[1]benzofuran-3',2"-pyrrol]-5"-amine

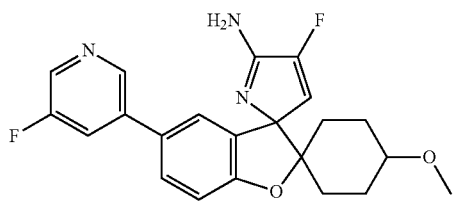

May be prepared with 5-Fluoropyridine-3-boronic acid by method (xiii)

Example 30: 5'-(5-chloropyridin-3-yl)-4"-fluoro-4-methoxydispiro[cyclohexane-1,2'-[1]benzofuran-3',2"-pyrrol]-5"-amine

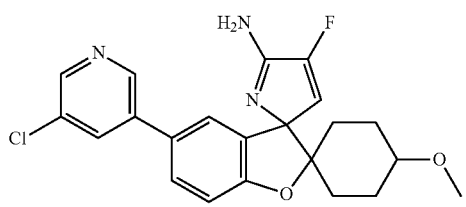 [SMILES: COC1CCC2(CC1)Oc1ccc(-c3cncc(Cl)c3)cc1C21C=C(F)C(N)=N1]

May be prepared with 5-Chloropyridine-3-boronic acid by method (xiii)

Example 31: 5'-(5-chloro-6-methylpyridin-3-yl)-4"-fluoro-4-methoxydispiro[cyclohexane-1,2'-[1]benzofuran-3',2"-pyrrol]-5"-amine

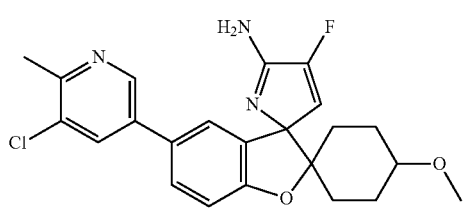 [SMILES: COC1CCC2(CC1)Oc1ccc(-c3cnc(C)c(Cl)c3)cc1C21C=C(F)C(N)=N1]

May be prepared with Intermediate 3 by method (xiii)

Example 32: 4"-fluoro-4-methoxy-5'-(5-methylpyridin-3-yl)dispiro[cyclohexane-1,2'-[1]benzofuran-3',2"-pyrrol]-5"-amine

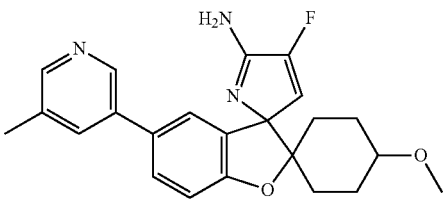

May be prepared with 5-Methylpyridine-3-boronic acid by method (xiii)

Example 33: 4"-fluoro-4-methoxy-5'-(3-methoxyphenyl)dispiro[cyclohexane-1,2'-[1]benzofuran-3',2"-pyrrol]-5"-amine

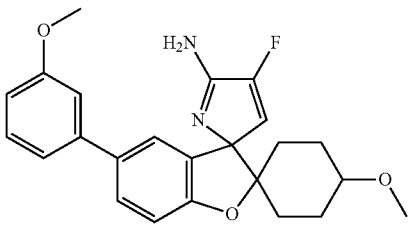 [SMILES: COc1cccc(-c2ccc3c(c2)C2(C=C(F)C(N)=N2)C2(CCC(OC)CC2)O3)c1]

May be prepared with 3-Methoxyphenylboronic acid by method (xiii)

Example 34: 5'-(3-chlorophenyl)-4"-fluoro-4-methoxydispiro[cyclohexane-1,2'-[1]benzofuran-3',2"-pyrrol]-5"-amine

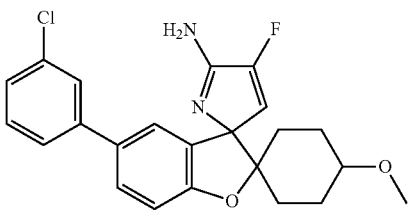 [SMILES: COC1CCC2(CC1)Oc1ccc(-c3cccc(Cl)c3)cc1C21C=C(F)C(N)=N1]

May be prepared with 3-Chlorophenylboronic acid by method (xiii)

Example 35: 3-(5"-amino-4"-fluoro-4-methoxy-dispiro[cyclohexane-1,2'-[1]benzofuran-3',2"-pyrrol]-5'-yl)-5-chlorobenzonitrile

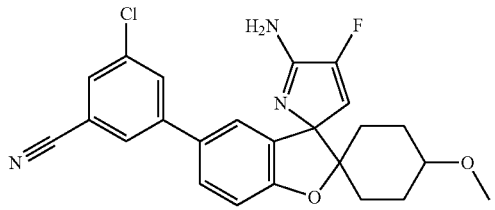 [SMILES: COC1CCC2(CC1)Oc1ccc(-c3cc(Cl)cc(C#N)c3)cc1C21C=C(F)C(N)=N1]

May be prepared with 3-Chloro-5-cyanophenylboronic acid by method (xiii)

Example 36: 4"-fluoro-4-methoxy-5'-phenyldispiro[cyclohexane-1,2'-[1]benzofuran-3',2"-pyrrol]-5"-amine

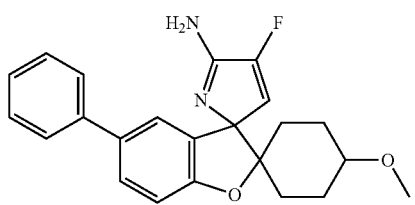 [SMILES: COC1CCC2(CC1)Oc1ccc(-c3ccccc3)cc1C21C=C(F)C(N)=N1]

May be prepared with Phenylboronic acid by method (xiii)

Example 37: 4"-fluoro-5'-[3-fluoro-5-(methoxymethyl)phenyl]-4-methoxydispiro[cyclohexane-1,2'-[1]benzofuran-3',2"-pyrrol]-5"-amine

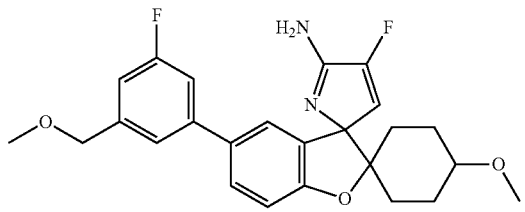

May be prepared with Intermediate 6 by method (xiii)

Example 38: 5'-[3-chloro-5-(methoxymethyl)phenyl]-4"-fluoro-4-methoxydispiro[cyclohexane-1,2'-[1]benzofuran-3',2"-pyrrol]-5"-amine

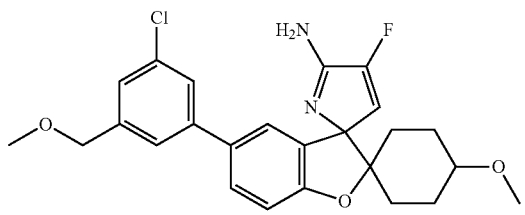

May be prepared with Intermediate 5 by method (xiii)

Example 39: 3-(5"-amino-4"-fluoro-4-methoxy-dispiro[cyclohexane-1,2'-[1]benzofuran-3',2"-pyrrol]-5'-yl)-5-(methoxymethyl)benzonitrile

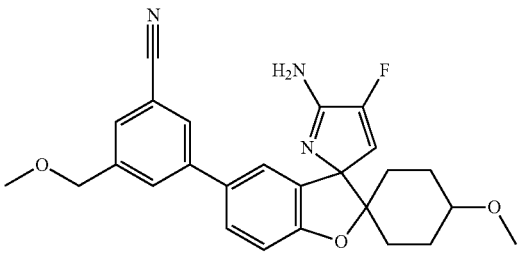

May be prepared with Intermediate 4 by method (xiii)

Example 40: 4"-fluoro-4-methoxy-5'-[5-(prop-1-yn-1-yl)pyridin-3-yl]dispiro[cyclohexane-1,2'-[1]benzofuran-3',2"-pyrrol]-5"-amine

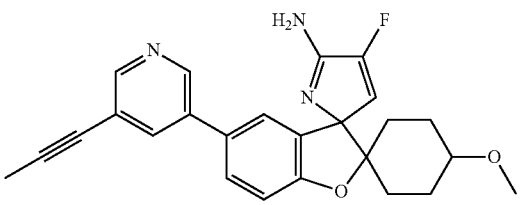 [SMILES: CC#Cc1cncc(-c2ccc3c(c2)C2(C=C(F)C(N)=N2)C2(CCC(OC)CC2)O3)c1]

May be prepared with 5-(Prop-1-ynyl)pyridin-3-ylboronic acid by method (xiii)

The following compound may be prepared using Intermediate 9 which can be converted to 6'-bromo-4"-fluoro-4-methoxy-4-methyl-3'H-dispiro[cyclohexane-1,2'-[1]benzofuran-3',2"-pyrrol]-5"-amine using methods described above. Additional reagents and methods are listed.

Example 41: 4"-fluoro-4-methoxy-4-methyl-5'-(pyrimidin-5-yl)dispiro[cyclohexane-1,2'-[1]benzofuran-3',2"-pyrrol]-5"-amine

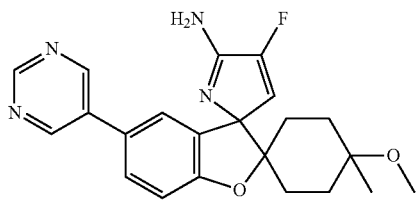 [SMILES: COC1(C)CCC2(CC1)Oc1ccc(-c3cncnc3)cc1C21C=C(F)C(N)=N1]

May be prepared with Pyrimidine-5-boronic acid by method (xiii)

The following compound may be prepared using Intermediate 10 which can be converted to 5'-bromo-4-(difluoromethoxy)-4"-fluorodispiro[cyclohexane-1,2'-[1]benzofuran-3',2"-pyrrol]-5"-amine using methods described above. Additional reagents and methods are listed.

Example 42: 4-(difluoromethoxy)-4''-fluoro-5'-(pyrimidin-5-yl)dispiro[cyclohexane-1,2'-[1]benzofuran-3',2''-pyrrol]-5''-amine

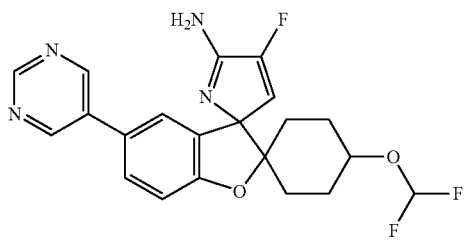 [SMILES: NC1=NC2(C=C1F)c1cc(-c3cncnc3)ccc1OC21CCC(OC(F)F)CC1]

May be prepared with Pyrimidine-5-boronic acid by method (xiii)

The biological of activity of compounds of examples 1-10 is presented in Table I, below, and that of other compounds according to the present invention may be measured using the following methods.

TR-FRET Assay

The β-secretase enzyme used in the TR-FRET is prepared as follows:

The cDNA for the soluble part of the human 13-Secretase (AA 1-AA 460) was cloned using the ASP2-Fc10-1-IRES-GFP-neoK mammalian expression vector. The gene was fused to the Fc domain of IgG1 (affinity tag) and stably cloned into HEK 293 cells. Purified sBACE-Fc was stored in −80° C. in Tris buffer, pH 9.2 and had a purity of 40%.

The enzyme (truncated form) was diluted to 6 μg/mL (stock 1.3 mg/mL) and the TruPoint BACE1 Substrate to 200 nM (stock 120 μM) in reaction buffer (NaAcetate, chaps, triton x-100, EDTA pH4.5). The robotic systems Biomek FX and Velocity 11 were used for all liquid handling and the enzyme and substrate solutions were kept on ice until they were placed in the robotic system. Enzyme (9 μL) was added to the plate then 1 μL of compound in dimethylsulphoxide was added, mixed and pre-incubated for 10 minutes. Substrate (10 μL) was then added, mixed and the reaction proceeded for 15 minutes at r.t. The reaction was stopped with the addition of Stop solution (7 μL, NaAcetate, pH 9). The fluorescence of the product was measured on a Victor II plate reader with an excitation wavelength of 340 nm and an emission wavelength of 615 nm. The assay was performed in a Costar 384 well round bottom, low volume, non-binding surface plate (Corning #3676). The final concentration of the enzyme was 2.7 μg/mL; the final concentration of substrate was 100 nM (Km of ~250 nM). The dimethylsulphoxide control, instead of test compound, defined the 100% activity level and 0% activity was defined by wells lacking enzyme (replaced with reaction buffer). A control inhibitor was also used in dose response assays and had an $IC_{50}$ of ~150 nM.

Diluted TR-FRET Assay

Compounds with a high affinity were further tested in a diluted TR-FRET assay, conditions as described above for the TR-FRET assay, but with 50 times less enzyme and a 6.5 h reaction time at r.t. in the dark.

sAPPβ Release Assay

SH-SY5Y cells were cultured in DMEM/F-12 with Glutamax, 10% FCS and 1% non-essential amino acids and cryopreserved and stored at −140° C. at a concentration of 7.5-9.5×10⁶ cells per vial. Thaw cells and seed at a conc. of around 10000 cells/well in DMEM/F-12 with Glutamax, 10% FCS and 1% non-essential amino acids to a 384-well tissue culture treated plate, 100 μL cell susp/well. The cell plates were then incubated for 7-24 h at 37° C., 5% $CO_2$. The cell medium was removed, followed by addition of 30 μL compound diluted in DMEM/F-12 with Glutamax, 10% FCS, 1% non-essential amino acids and 1% PeSt to a final conc. of 1% DMSO. The compounds were incubated with the cells for 17 h (overnight) at 37° C., 5% $CO_2$. Meso Scale Discovery (MSD) plates were used for the detection of sAPPβ release. MSD sAPPβ plates were blocked in 1% BSA in Tris wash buffer (40 μL/well) for 1 h on shake at r.t. and washed 1 time in Tris wash buffer (40 μL/well). 20 μL of medium was transferred to the pre-blocked and washed MSD sAPPβ microplates, and the cell plates were further used in an ATP assay to measure cytotoxicity. The MSD plates were incubated with shaking at r.t. for 2 h and the media discarded. 10 μL detection antibody was added (1 nM) per well followed by incubation with shaking at r.t. for 2 h and then discarded. 40 μL Read Buffer was added per well and the plates were read in a SECTOR Imager.

ATP Assay

As indicated in the sAPPβ release assay, after transferring 20 μL medium from the cell plates for sAPPβ detection, the plates were used to analyse cytotoxicity using the ViaLight™ Plus cell proliferation/cytotoxicity kit from Cambrex BioScience that measures total cellular ATP. The assay was performed according to the manufacture's protocol. Briefly, 10 μL cell lysis reagent was added per well. The plates were incubated at r.t. for 10 min. Two min after addition of 25 μL reconstituted ViaLight™ Plus ATP reagent, the luminescence was measured in a Wallac Victor2 1420 multilabel counter. Tox threshold is a signal below 75% of the control.

Results

Typical IC50 values for the compounds of the present invention are in the range of about 0.01 to about 100,000 nM. Biological data is given below in Table I.

TABLE I

| Example No. | $IC_{50}$ in TR-FRET assay (nM) | $IC_{50}$ in sAPPβ release assay (nM) | Example No. | $IC_{50}$ in TR-FRET assay (nM) | $IC_{50}$ in sAPPβ release assay (nM) |
|---|---|---|---|---|---|
| 1 | 22[a] | 1.1 | 2 | 1970 | 56 |
| 3 | 18 | 0.031 | 4 | 258 | 1.1 |
| 5 | 71 | 3.0 | 6 | 770 | 19 |
| 7 | 770 | 30 | 8 | 640 | 256 |
| 9 | 3790 | 168 | 10 | 37 | ND |
| 11 | 1220 | ND | | | |

[a]$IC_{50}$ from the diluted FRET assay.
ND is Not done

The invention claimed is:

1. A compound according to formula (I):

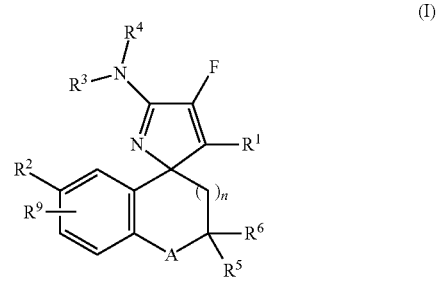

wherein:
A is —O—, —CH$_2$—, —CH$_2$CH$_2$—, —OCH$_2$—, —CH$_2$O—, or —CF$_2$—;
n is 0 or 1;
R$^1$ is H, C$_{1-6}$alkyl or C$_{0-6}$alkylC$_{3-6}$cycloalkyl;
R$^2$ is C$_{0-6}$alkylaryl, C$_{0-6}$alkylheteroaryl, C$_{2-6}$alkynyl, C$_{1-6}$alkyl, halogen, cyano, or OR$^8$, wherein said C$_{0-6}$alkylaryl, C$_{0-6}$alkylheteroaryl, C$_{2-6}$alkynyl, or C$_{1-6}$alkyl is optionally substituted with one to three R$^7$;
R$^3$ is H;
R$^4$ is H;
R$^5$ and R$^6$ is independently hydrogen, heterocyclyl, C$_{3-6}$cycloalkyl, aryl, heteroaryl or C$_{1-6}$alkyl, wherein said heterocyclyl, C$_{3-6}$cycloalkyl, aryl, heteroaryl or C$_{1-6}$alkyl is optionally substituted with one or two substituents independently selected from halogen, C$_{1-6}$alkyl, C$_{1-6}$haloalkyl, cyano, or OR$^8$; provided that R$^5$ and R$^6$ are not hydrogen at the same time;
or R$^5$ and R$^6$ together with the carbon to which they are attached, form a ring B, which is a 3-7 membered cycloalkyl or heterocyclyl monocyclic ring, or a 7-12 membered bicyclic cycloalkyl or heterocyclyl ring; and wherein ring B is optionally substituted by one or more substituents independently selected from oxo, halogen, C$_{1-6}$alkyl, C$_{1-6}$haloalkyl, cyano, or OR$^8$; and ring B is optionally fused with an aryl or heteroaryl to form a bi- or polycyclic system;
R$^7$ is independently C$_{1-6}$alkyl, halogen, cyano, C$_{0-6}$alkylaryl, C$_{0-6}$alkylheteroaryl, C$_{0-6}$alkylC$_{3-6}$cycloalkyl, OC$_{1-6}$alkyl, or C$_{2-6}$alkynyl, wherein said C$_{1-6}$alkyl, C$_{0-6}$alkylaryl, C$_{0-6}$alkylheteroaryl, C$_{0-6}$alkylC$_{3-6}$cycloalkyl, OC$_{1-6}$alkyl, or C$_{2-6}$alkynyl is optionally substituted with 1-3 substituents independently selected from halogen, cyano, C$_{1-6}$alkyl, C$_{0-6}$alkylC$_{3-6}$cycloalkyl, C$_{1-6}$haloalkyl, OC$_{1-6}$alkyl, and OC$_{1-6}$haloalkyl;
R$^8$ is independently hydrogen, C$_{1-6}$alkyl, C$_{0-6}$alkyl C$_{3-6}$cycloalkyl, C$_{2-6}$alkynyl, aryl or heteroaryl; wherein said C$_{1-6}$alkyl, aryl or heteroaryl is optionally substituted with one or more substituents independently selected from halogen, cyano, and C$_{1-6}$alkyl; and
R$^9$ is H, F, OH, CH$_3$, Cl or OCH$_3$;
R$^9$ is one or more substituents independently selected from H, F, OH, CH$_3$, Cl and OCH$_3$;
as a free base or a pharmaceutically acceptable salt thereof.

2. A compound according to claim 1, wherein A is —O—, —CH$_2$—, —OCH$_2$— or —CH$_2$O—.

3. A compound according to claim 1 or 2, wherein R$^5$ and R$^6$ together with the carbon to which they are attached, form a ring B, which is a 3-7 membered cycloalkyl or heterocyclyl monocyclic ring, or a 9-12 membered bicyclic cycloalkyl or heterocyclyl ring; and wherein ring B is optionally substituted by one or two substituents independently selected from oxo, halogen, C$_{1-6}$alkyl or OR$^8$; and ring B is optionally fused with an aryl or heteroaryl to form a bi- or polycyclic system.

4. A compound according to claim 1 or 2, wherein R$^9$ is H or F.

5. A compound according to claim 1, wherein
A is —O—, —CH$_2$—, —OCH$_2$— or —CH$_2$O—;
n is 0 or 1;
R$^2$ is aryl, heteroaryl or C$_{2-6}$alkynyl, wherein said aryl, heteroaryl or C$_{2-6}$alkynyl is optionally substituted with one to three R$^7$;
R$^5$ and R$^6$ is independently hydrogen or heterocyclyl, wherein said heterocyclyl is optionally substituted with two substituents independently selected from C$_{1-6}$alkyl; provided that R$^5$ and R$^6$ are not hydrogen at the same time;
or R$^5$ and R$^6$ together with the carbon to which they are attached, form a ring B, which is a 3-7 membered cycloalkyl or heterocyclyl monocyclic ring, or a 9-12 membered bicyclic cycloalkyl or heterocyclyl ring; and wherein ring B is optionally substituted by one or two substituents independently selected from oxo, halogen, C$_{1-6}$alkyl or OR$^8$; and ring B is optionally fused with an aryl or heteroaryl to form a bicyclic system;
R$^7$ is C$_{1-6}$alkyl, halogen, cyano, OC$_{1-6}$alkyl or C$_{2-6}$alkynyl, wherein said C$_{1-6}$alkyl, OC$_{1-6}$alkyl or C$_{2-6}$alkynyl is optionally substituted with 1-3 substituents independently selected from halogen, cyano, C$_{1-6}$alkyl, C$_{0-6}$alkylC$_{3-6}$cycloalkyl, C$_{1-6}$haloalkyl, OC$_{1-6}$alkyl and OC$_{1-6}$haloalkyl;
R$^8$ is independently C$_{1-6}$alkyl or C$_{2-6}$alkynyl, wherein said C$_{1-6}$alkyl is optionally substituted with one or more halogen; and
R$^9$ is H, F, OH, CH$_3$, Cl or OR$^8$.

6. A compound according to claim 1, wherein
A is —O—, —CH$_2$—, —OCH$_2$— or —CH$_2$O—;
n is 0;
R$^2$ is aryl, heteroaryl or C$_{2-6}$alkynyl, wherein said aryl, heteroaryl or C$_{2-6}$alkynyl is optionally substituted with one to three R$^7$;
R$^5$ and R$^6$ together with the carbon to which they are attached form a cyclohexyl ring, which is substituted with OR$^8$;
R$^7$ is C$_{1-3}$alkyl, halogen, cyano, OC$_{1-3}$alkyl or C$_{2-6}$alkynyl, wherein C$_{1-3}$alkyl is optionally substituted with OC$_{1-3}$alkyl;
R$^8$ is C$_{1-3}$alkyl;
R$^9$ is H or F.

7. A compound according to claim 1, wherein
A is —O—, —CH$_2$—, —OCH$_2$— or —CH$_2$O—;
n is 0;
R$^2$ is phenyl, pyridinyl or pyrimidinyl, wherein said phenyl, pyridinyl or pyrimidinyl is optionally substituted with one or two R$^7$;
R$^5$ and R$^6$ together with the carbon to which they are attached form a cyclohexyl ring, which is substituted with methoxy;
R$^7$ is chloro, fluoro, cyano, methoxy, methoxymethyl or prop-1-yn-1-yl; and
R$^9$ is H or F.

8. A compound according to claim 1, wherein
A is —O—, —CH$_2$—;
n is 0;
R$^2$ is phenyl, pyridinyl or pyrimidinyl, wherein said phenyl, pyridinyl or pyrimidinyl is optionally substituted with one or two R$^7$;
R$^5$ and R$^6$ together with the carbon to which they are attached form a cyclohexyl ring, which is substituted with methoxy;
R$^7$ is fluoro, cyano, or prop-1-yn-1-yl; and
R$^9$ is H or F.

9. A compound according to claim 1, selected from the group consisting of:
(1r,4r)-4"-fluoro-4-methoxy-6'-(pyrimidin-5-yl)-3'H-dispiro[cyclohexane-1,2'-indene-1',2"-pyrrol]-5"amine;
(1s,4s)-4"-Fluoro-4-methoxy-6'-(pyrimidin-5-yl)-3'H-dispiro[cyclohexane-1,2'-indene-1',2"-pyrrol]-5"amine;

(1r,4r)-4"-Fluoro-4-methoxy-6'[5-(prop-1-yn-1-yl)pyridin-3-yl]-3'H-dispiro[cyclohexane-1,2'-indene-1',2"-pyrrol]-5"amine;

(1 s,4s)-4"-Fluoro-4-methoxy-6'[5-(prop-1-yn-1-yl)pyridin-3-yl]-3'H-dispiro[cyclohexane-1,2'-indene-1',2"-pyrrol]-5"amine, and 3-[(1s,4s)-5"-Amino-4"-fluoro-4-methoxydispiro[cyclohexane-1,2'-[1]benzofuran-3',2"-pyrrol]-5'-yl]-5-fluorobenzonitrile;

as a free base or a pharmaceutically acceptable salt of any foregoing compound.

10. A compound according to claim 1, selected from the group consisting of:

4'-Fluoro-3,3-dimethyl-6-(pyrimidin-5-yl)spiro[chroman-4,2'-pyrrol]-5'-amine;

4'-Fluoro-6-(5-fluoropyridin-3-yl)-3,3-dimethylspiro[chroman-4,2'-pyrrol]-5'-amine;

6-(3,5-Difluorophenyl)-4'-fluoro-3,3-dimethylspiro[chroman-4,2'-pyrrol]-5'-amine;

4'-Fluoro-2,2-dimethyl-6-(pyrimidin-5-yl)-2,3-dihydrospiro[indene-1,2'-pyrrol]-5'-amine;

4"-Fluoro-6'-(3-fluoropropoxy)-4-[(2H3)methyloxy]-3'H-dispiro[cyclohexane-1,2'-indene-1',2"-pyrrol]-5"-amine, isomer 1, and 4"-Fluoro-6'-(3-fluoropropoxy)-4-[(2H3)methyloxy]-3'H-dispiro[cyclohexane-1,2'-indene-1',2"-pyrrol]-5"-amine, isomer 2;

4"-fluoro-4-methoxy-6'-(pyridin-3-yl)-3'H-dispiro[cyclohexane-1,2'-indene-1',2"-pyrrol]-5"-amine;

4"-fluoro-6'-(5-fluoropyridin-3-yl)-4-methoxy-3'H-dispiro[cyclohexane-1,2'-indene-1',2"-pyrrol]-5"-amine;

6'-(5-chloropyridin-3-yl)-4"-fluoro-4-methoxy-3'H-dispiro[cyclohexane-1,2'-indene-1',2"-pyrrol]-5"-amine;

6'-(5-chloro-6-methylpyridin-3-yl)-4"-fluoro-4-methoxy-3'H-dispiro[cyclohexane-1,2'-indene-1',2"-pyrrol]-5"-amine;

4"-fluoro-4-methoxy-6'-(5-methylpyridin-3-yl)-3'H-dispiro[cyclohexane-1,2'-indene-1',2"-pyrrol]-5"-amine;

4"-fluoro-4-methoxy-6'-(3-methoxyphenyl)-3'H-dispiro[cyclohexane-1,2'-indene-1',2"-pyrrol]-5"-amine;

6'-(3-chlorophenyl)-4"-fluoro-4-methoxy-3'H-dispiro[cyclohexane-1,2'-indene-1',2"-pyrrol]-5"-amine;

3-(5"-amino-4"-fluoro-4-methoxy-3'H-dispiro[cyclohexane-1,2'-indene-1',2"-pyrrol]-6'-yl)-5-fluorobenzonitrile;

3-(5"-amino-4"-fluoro-4-methoxy-3'H-dispiro[cyclohexane-1,2'-indene-1',2"-pyrrol]-6'-yl)-5-chlorobenzonitrile;

4"-fluoro-4-methoxy-6'-phenyl-3'H-dispiro[cyclohexane-1,2'-indene-1',2"-pyrrol]-5"-amine;

4"-fluoro-6-[3-fluoro-5-(methoxymethyl)phenyl]-4-methoxy-3'H-dispiro[cyclohexane-1,2'-indene-1',2"-pyrrol]-5"-amine;

6'-[3-chloro-5-(methoxymethyl)phenyl]-4"-fluoro-4-methoxy-3'H-dispiro[cyclohexane-1,2'-indene-1',2"-pyrrol]-5"-amine;

3-(5"-amino-4"-fluoro-4-methoxy-3'H-dispiro[cyclohexane-1,2'-indene-1',2"-pyrrol]-6'-yl)-5-(methoxymethyl)benzonitrile;

4"-fluoro-4-methoxy-4-methyl-6'-(pyrimidin-5-yl)-3'H-dispiro[cyclohexane-1,2'-indene-1',2"-pyrrol]-5"-amine;

4-(difluoromethoxy)-4"-fluoro-6'-(pyrimidin-5-yl)-3'H-dispiro[cyclohexane-1,2'-indene-1',2"-pyrrol]-5"-amine 4"-fluoro-4-methoxy-5'-(pyrimidin-5-yl)dispiro[cyclohexane-1,2'-[1]benzofuran-3',2"-pyrrol]-5"-amine;

4"-fluoro-4-methoxy-5'-(pyridin-3-yl)dispiro[cyclohexane-1,2'-[1]benzofuran-3',2"-pyrrol]-5"-amine;

4"-fluoro-5'-(5-fluoropyridin-3-yl)-4-methoxydispiro[cyclohexane-1,2'-[1]benzofuran-3',2"-pyrrol]-5"-amine;

5'-(5-chloropyridin-3-yl)-4"-fluoro-4-methoxydispiro[cyclohexane-1,2'-[1]benzofuran-3',2"-pyrrol]-5"-amine;

5'-(5-chloro-6-methylpyridin-3-yl)-4"-fluoro-4-methoxydispiro[cyclohexane-1,2'-[1]benzofuran-3',2"-pyrrol]-5"-amine;

4"-fluoro-4-methoxy-5'-(5-methylpyridin-3-yl)dispiro[cyclohexane-1,2'-[1]benzofuran-3',2"-pyrrol]-5"-amine;

4"-fluoro-4-methoxy-5'-(3-methoxyphenyl)dispiro[cyclohexane-1,2'-[1]benzofuran-3',2"-pyrrol]-5"-amine;

5'-(3-chlorophenyl)-4"-fluoro-4-methoxydispiro[cyclohexane-1,2'-[1]benzofuran-3',2"-pyrrol]-5"-amine;

3-(5"-amino-4"-fluoro-4-methoxydispiro[cyclohexane-1,2'-[1]benzofuran-3',2"-pyrrol]-5'-yl)-5-chlorobenzonitrile;

4"-fluoro-4-methoxy-5'-phenyldispiro[cyclohexane-1,2'-[1]benzofuran-3',2"-pyrrol]-5"-amine;

4"-fluoro-5'-[3-fluoro-5-(methoxymethyl)phenyl]-4-methoxydispiro[cyclohexane-1,2'-[1]benzofuran-3',2"-pyrrol]-5"-amine;

5'-[3-chloro-5-(methoxymethyl)phenyl]-4"-fluoro-4-methoxydispiro[cyclohexane-1,2'-[1]benzofuran-3',2"-pyrrol]-5"-amine;

3-(5"-amino-4"-fluoro-4-methoxydispiro[cyclohexane-1,2'-[1]benzofuran-3',2"-pyrrol]-5'-yl)-5-(methoxymethyl)benzonitrile;

4"-fluoro-4-methoxy-5'-[5-(prop-1-yn-1-yl)pyridin-3-yl]dispiro[cyclohexane-1,2'-[1]benzofuran-3',2"-pyrrol]-5"-amine;

4"-fluoro-4-methoxy-4-methyl-5'-(pyrimidin-5-yl)dispiro[cyclohexane-1,2'-[1]benzofuran-3',2"-pyrrol]-5"-amine; and 4-(difluoromethoxy)-4"-fluoro-5'-(pyrimidin-5-yl)dispiro[cyclohexane-1,2'-[1]benzofuran-3',2"-pyrrol]-5"-amine, as a free base or a pharmaceutically acceptable salt of any foregoing compound.

11. A pharmaceutical composition comprising as active ingredient a therapeutically effective amount of a compound according to claim 1, or a pharmaceutically acceptable salt thereof, in association with pharmaceutically acceptable excipients, carriers or diluents.

12. A method of treating or preventing an Aβ-related pathology in a patient in need thereof, comprising administering to said patient a therapeutically effective amount of a compound of claim 1 or a pharmaceutically acceptable salt thereof.

13. The method of claim 12, wherein said Aβ-related pathology is Down's syndrome, a β-amyloid angiopathy, cerebral amyloid angiopathy, hereditary cerebral hemorrhage, a disorder associated with cognitive impairment, MCI ("mild cognitive impairment"), Alzheimer's disease, memory loss, attention deficit symptoms associated with Alzheimer's disease, neurodegeneration associated with Alzheimer's disease, dementia of mixed vascular origin, dementia of degenerative origin, pre-senile dementia, senile dementia, dementia associated with Parkinson's disease, progressive supranuclear palsy or cortical basal degeneration.

14. A method of treating or preventing Alzheimer's Disease in a patient in need thereof, comprising administering to said patient a therapeutically effective amount of a compound of claim 1, or a pharmaceutically acceptable salt thereof.

15. A method of treating or preventing an Aβ-related pathology in a patient in need thereof, comprising administering to said patient a therapeutically effective amount of a compound of claim 1, or a pharmaceutically acceptable salt thereof, and at least one cognitive enhancing agent, memory enhancing agent, or choline esterase inhibitor.

16. A compound according to claim 3, wherein $R^9$ is H or F.

* * * * *